United States Patent
Hayakawa et al.

(10) Patent No.: US 9,693,705 B2
(45) Date of Patent: Jul. 4, 2017

(54) BIOSIGNAL MEASUREMENT DEVICE

(75) Inventors: Tomohiro Hayakawa, Saitama (JP); Haruhiko Soma, Tokyo (JP); Seiji Wada, Kanagawa (JP); Fan Wang, Tokyo (JP); Natsuki Kimura, Tokyo (JP); Mitsuhiro Nakamura, Kanagawa (JP); Shiko Yamashita, Tokyo (JP); Yusaku Nakashima, Tokyo (JP); Takuro Yamamoto, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 1000 days.

(21) Appl. No.: 13/380,424

(22) PCT Filed: Jun. 28, 2010

(86) PCT No.: PCT/JP2010/061362
§ 371 (c)(1),
(2), (4) Date: Apr. 11, 2012

(87) PCT Pub. No.: WO2011/002093
PCT Pub. Date: Jan. 6, 2011

(65) Prior Publication Data
US 2012/0190959 A1    Jul. 26, 2012

(30) Foreign Application Priority Data

Jun. 29, 2009 (JP) .................................. 2009-153985
Oct. 23, 2009 (JP) .................................. 2009-244875
Jun. 21, 2010 (JP) .................................. 2010-140711

(51) Int. Cl.
*A61B 5/0478* (2006.01)
*A61B 5/00* (2006.01)
*A61B 5/0496* (2006.01)

(52) U.S. Cl.
CPC .......... *A61B 5/0478* (2013.01); *A61B 5/4815* (2013.01); *A61B 5/6814* (2013.01); *A61B 5/0496* (2013.01); *A61B 5/6887* (2013.01)

(58) Field of Classification Search
CPC ................ A61B 5/0476; A61B 5/0478; A61B 5/0482–5/04847; A61B 5/4058;
(Continued)

(56) References Cited

U.S. PATENT DOCUMENTS 3,896,790 A * 7/1975 Dikmen ......................... 600/383
4,189,788 A * 2/1980 Schenke et al. .................. 2/209
(Continued)

FOREIGN PATENT DOCUMENTS

CN    1909828         2/2007
JP    03-016905       2/1991
(Continued)

OTHER PUBLICATIONS

Grozea et al. "Bristle-Sensors—Low-Cost FLexible Passive Dry EEG Electrodes for Neurofeedback and BCI Applications" J. Neural Eng. 8(2) 025008 (2011).*
(Continued)

*Primary Examiner* — Lee S Cohen
*Assistant Examiner* — Erin M Cardinal
(74) *Attorney, Agent, or Firm* — Chip Law Group

(57) ABSTRACT

A biosignal measurement device is proposed which can improve measurement accuracy without forcing an excessive burden on subjects.

A biosignal measurement device used for measurement of a biosignal in a head includes a support that can support the head, and an electrode provided to the support. The electrode has a plurality of teeth each including an annular portion in which a pair of linear members having conductivity are formed in an annular shape, and a rod-like portion in which
(Continued)

the pair of linear members are wound in opposite directions and formed in a rod-like shape. The rod-like portion in each of the plurality of teeth is directly or indirectly fixed at one end to the support.

13 Claims, 50 Drawing Sheets

(58) Field of Classification Search
CPC ... A61B 5/4064; A61B 5/4076–5/4094; A61B 5/4806–5/4821; A61B 5/6801; A61B 5/6803; A61B 5/6814; A61B 5/6831; A61B 5/6839; A61B 2560/04; A61B 2560/0406; A61B 2560/0468; A61B 2562/0209; A61B 2562/14
USPC ............... 600/372, 382, 383, 390, 544–545; 381/379
See application file for complete search history.

(56) References Cited

U.S. PATENT DOCUMENTS

| | | | | |
|---|---|---|---|---|
| 4,706,679 | A * | 11/1987 | Schmidt | A61B 5/0478 600/383 |
| 4,995,392 | A * | 2/1991 | Sherwin et al. | 600/396 |
| 5,299,572 | A * | 4/1994 | Chen et al. | 600/395 |
| 5,331,959 | A * | 7/1994 | Imran | 600/383 |
| 6,032,064 | A * | 2/2000 | Devlin | A61B 5/04004 600/372 |
| 6,154,669 | A * | 11/2000 | Hunter | A61B 5/0478 600/383 |
| 2007/0106170 | A1* | 5/2007 | Dunseath | A61B 5/0478 600/544 |
| 2007/0167850 | A1 | 7/2007 | Russell et al. | |
| 2007/0225585 | A1* | 9/2007 | Washbon | A61B 5/0478 600/393 |
| 2008/0027345 | A1* | 1/2008 | Kumada et al. | 600/544 |
| 2009/0024017 | A1* | 1/2009 | Ruffini et al. | 600/395 |
| 2010/0106259 | A1* | 4/2010 | Llinas et al. | 623/25 |
| 2010/0198042 | A1* | 8/2010 | Popescu et al. | 600/383 |
| 2010/0274152 | A1* | 10/2010 | McPeck et al. | 600/544 |
| 2011/0098593 | A1* | 4/2011 | Low | A61B 5/0006 600/544 |
| 2012/0226127 | A1* | 9/2012 | Asjes et al. | 600/383 |

FOREIGN PATENT DOCUMENTS

| | | |
|---|---|---|
| JP | 05-261076 | 10/1993 |
| JP | 2001-340312 | 12/2001 |
| JP | 2002-301038 | 10/2002 |
| JP | 2005-152415 | 6/2005 |
| JP | 2006-06666 | 1/2006 |
| JP | 2006-094979 | 4/2006 |
| JP | 2009-078139 | 4/2009 |
| JP | 2010-051356 | 3/2010 |
| WO | 00/45701 | 8/2000 |
| WO | 2004/112604 | 12/2004 |
| WO | 2007/109745 | 9/2007 |
| WO | 2008/098346 | 8/2008 |

OTHER PUBLICATIONS

Japanese Patent Office, Notification of Reason(s) for Refusal issued in connection with Japanese Patent Application No. 2010-140711, dated Apr. 1, 2014. (7 pages).
Japanese Patent Office, Notification of Reason(s) for Refusal issued in connection with Japanese Patent Application No. 2010-140712, dated Apr. 1, 2014. (7 pages).
State Intellectual Property Office of PRC, Notification of the First Office Action issued in connection with PRC application No. 201080027985.7, dated Apr. 3, 2014. (13 pages).
State Intellectual Property Office of People's Republic of China, Notification of the First Office Action issued in connection with application No. 201080027987.6, dated Jul. 18, 2013. (14 pages).

* cited by examiner

FIG. 39
(C)
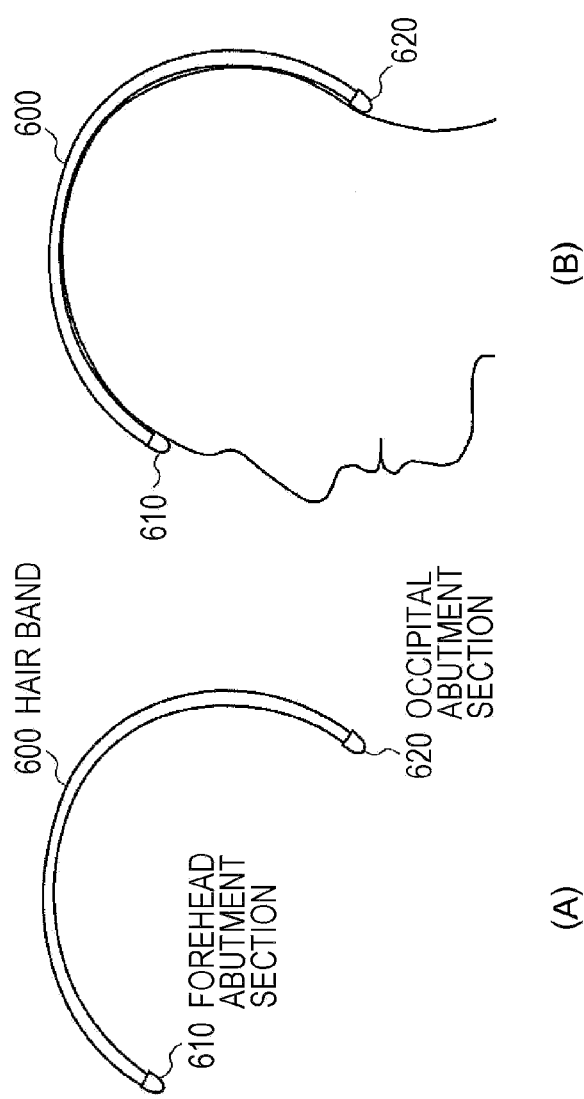
600 HAIR BAND
620 OCCIPITAL ABUTMENT SECTION
610 FOREHEAD ABUTMENT SECTION
(B)
(A)

FIG. 45
(A) 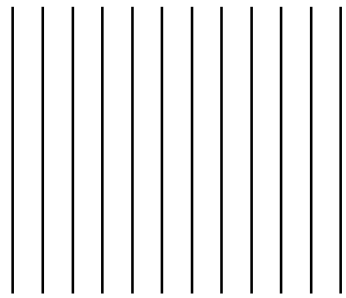
(B) 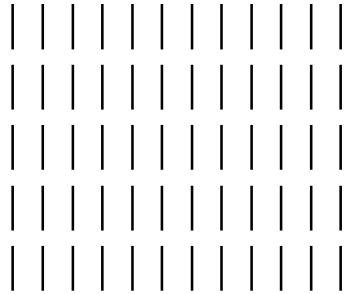
(C) 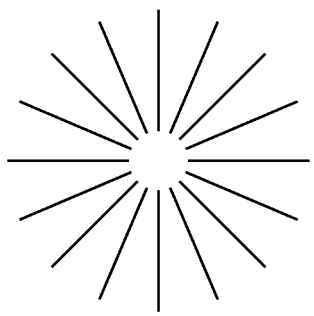

FIG. 54
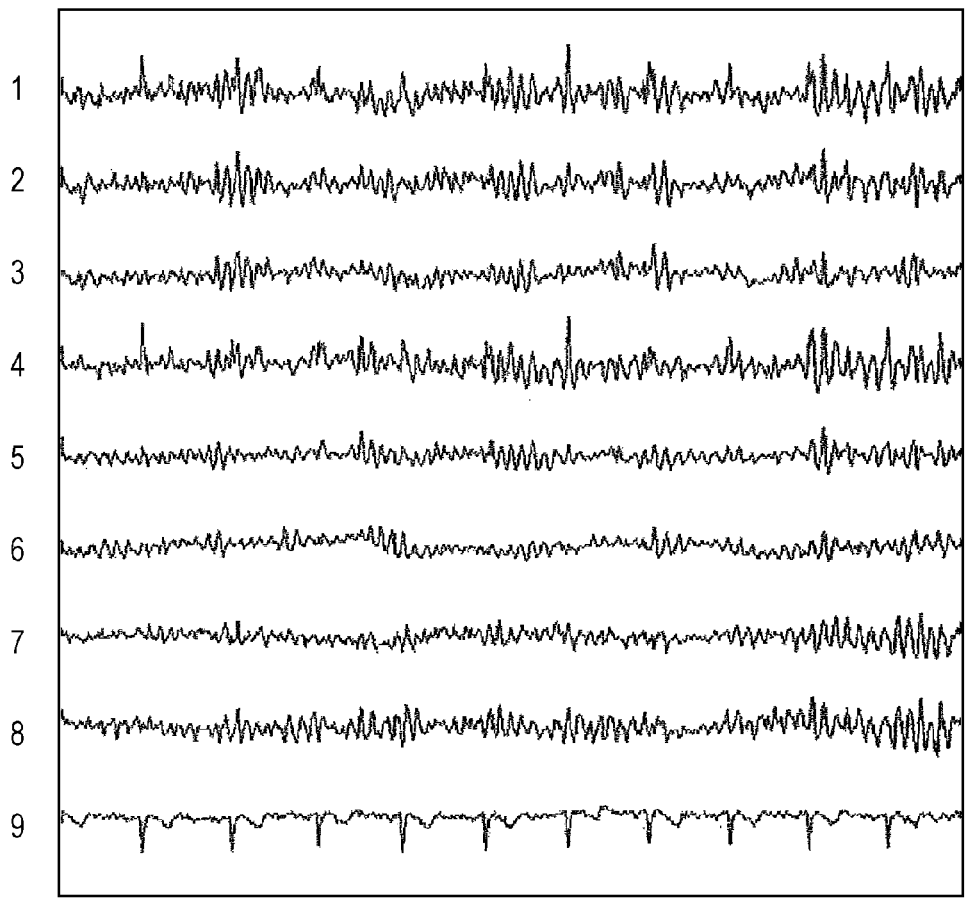
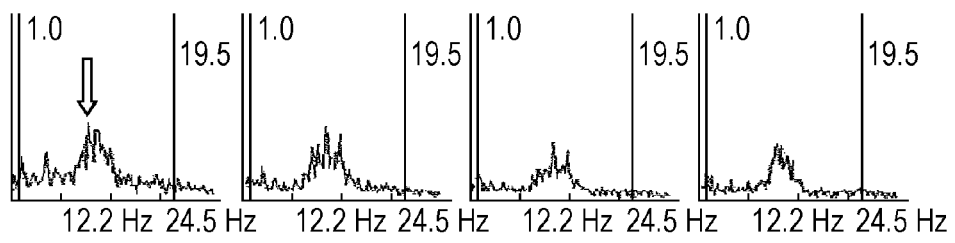
α-WAVES AROUND 10 Hz ARE DOMINANT

FIG. 55
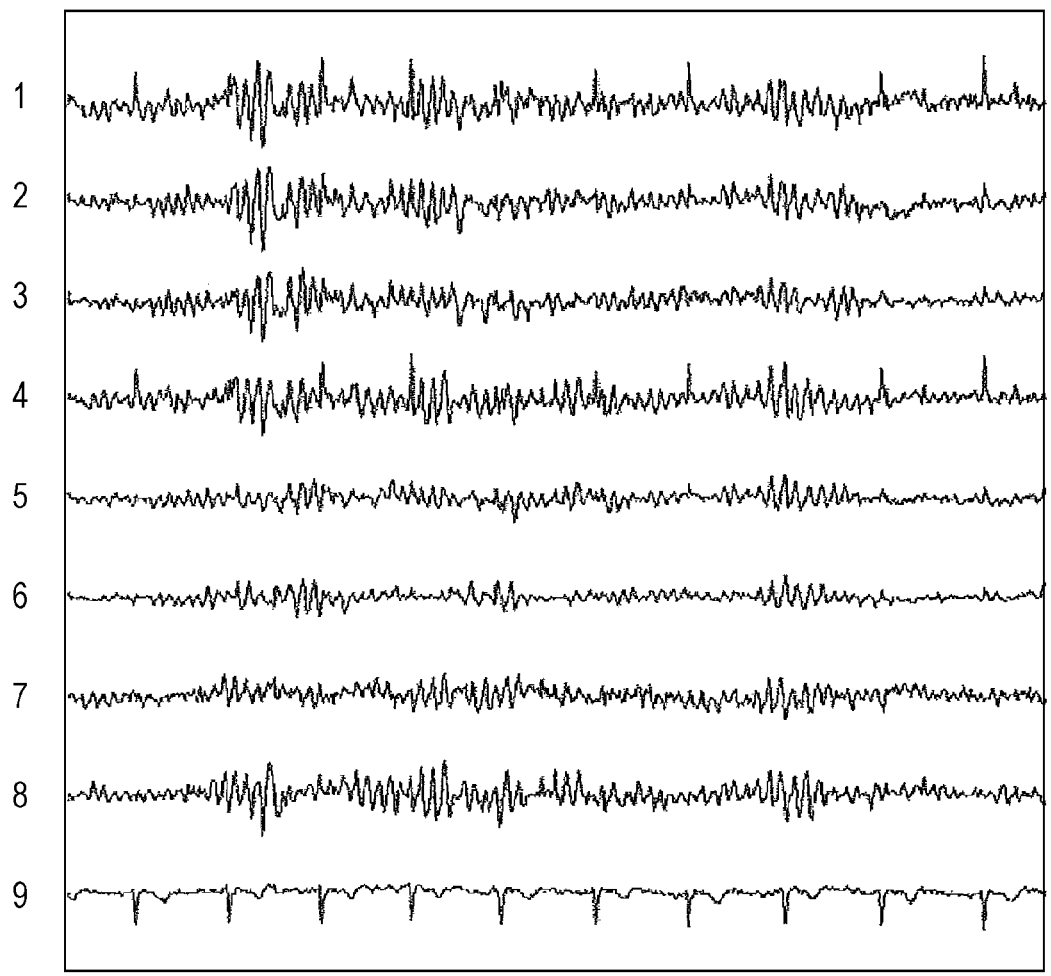
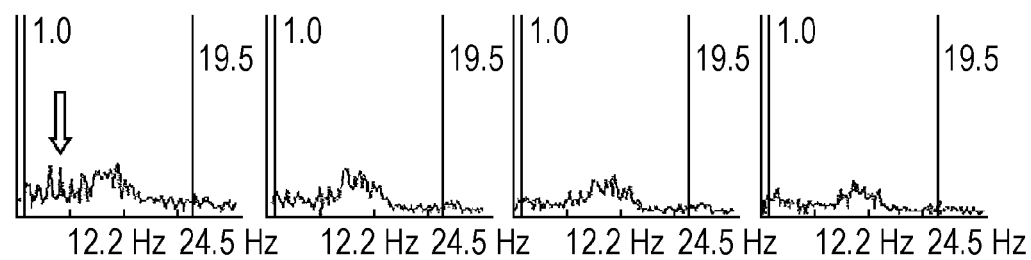
α-WAVES BECOME INTERMITTENT,
AND LOW FREQUENCY COMPONENTS INCREASE (A)

| Ch No | ITEM | G1 | G2 |
|---|---|---|---|
| 1 | P3-N1 | 1 | 7 |
| 2 | Pz-Nz | 2 | R |
| 3 | P4-N2 | 3 | 8 |
| 4 | O1-N1 | 4 | 7 |
| 5 | Oz-Nz | 5 | 8 |
| 6 | O2-N2 | 6 | R |
| 7 | P3-P4 | 1 | 3 |
| 8 | O1-O2 | 4 | 6 |
| 9 | N1-N2 | 7 | 8 |

(B)

BIOSIGNAL MEASUREMENT DEVICE

CROSS REFERENCE TO RELATED APPLICATIONS

The present application is a National Stage of International Application No. PCT/JP2010/061362 filed on Jun. 28, 2010, which claims priority to Japanese Patent Application No. 2010-140711, filed in the Japanese Patent Office on Jun. 21, 2010; Japanese Patent Application No. 2009-244875, filed in the Japanese Patent Office on Oct. 23, 2009; Japanese Patent Application No. 2009-1153985, filed in the Japanese Patent Office on Jun. 29, 2009, the entire contents of which are being incorporated herein by reference.

BACKGROUND

The present invention relates to a biosignal measurement device, and is suitable for the technical field of acquiring waves produced and propagated in a living body as electrical signals, or the like.

It is becoming clear that a decrease in the quality or amount (time) of sleep increases the risk of various lifestyle-related diseases, including circulatory diseases such as myocardial infarction and cerebral infarction, or endocrine diseases such as diabetes. Also, extension of or a decrease in the density of REM (Rapid Eye Movement) sleep is being strongly suspected as a cause of depression. Since sleep is thus related to many diseases and social problems modern human beings suffer from, assessing the quality of sleep will continue to grow in importance in the coming years.

Incidentally, polysomnography is known as a method of assessing sleep. Also, there has been proposed an apparatus that measures parameters required for assessing sleep cycle and the quality of sleep from heartbeat, without measuring brain waves (see, for example, PTL 1).

CITATION LIST

Patent Literature

PTL 1: Japanese Unexamined Patent Application Publication No. 2009-078139

However, polysomnography has a problem of forcing an excessive burden on subjects, because the subjects are confined to test facilities such as hospitals for a long period of time, and also there are a large number of attachments to the subjects.

On the other hand, although the illustrated patent literature reduces burden on subjects in comparison to polysomnography, the parameters required for assessing the quality of sleep are only indirect estimates. Therefore, it is difficult to grasp the depth of non-REM sleep, the duration and density of REM sleep, and so on that are important in assessing the quality of sleep, which poses a problem of poor measurement accuracy.

The present invention has been made in view of the above-mentioned points, and proposes a biosignal measurement device that can improve measurement accuracy without forcing an excessive burden on subjects.

To solve the problems, the present invention relates to a biosignal measurement device used for measurement of a biosignal in a head, including a support that can support the head, and an electrode provided to the support.

An electrode according to the first invention has a plurality of teeth each including an annular portion in which a pair of linear members having conductivity are formed in an annular shape, and a rod-like portion in which the pair of linear members are wound in opposite directions and formed in a rod-like shape, and the rod-like portion in each of the plurality of teeth are directly or indirectly fixed at one end to the support.

An electrode according to the second invention has a plurality of linear members, the plurality of linear members are fixed at one end to a surface of the support facing a scalp, at regular intervals in a row direction and a column direction, a root portion from the one end to a bending position between the one end and the other end stands upright orthogonally to the surface, and a portion from the bending position to the other end is bent obliquely to the root portion.

An electrode according to the third invention includes a plurality of conductive fibers, and the plurality of conductive fibers are fixed at one end to a surface of the support facing a scalp, at predetermined intervals so as to be orthogonal to the surface.

In the present invention, since the electrode is formed by conductive linear members or conductive fibers, the electrode is smoothly inserted in the roots of head hair for improved adherence to the scalp.

Also, since this electrode is fixed at a single point with its one end as a fixed end, the electrode is able to uniformly move around isotropically about the fixed end as the center. Thus, no matter from which direction a force is applied due to tossing and turning in bed or the like, flexible adaptation to the force is possible while maintaining a certain degree of adherence to the scalp. As a result, transient detachment of the electrode from the scalp can be reduced.

Therefore, since the prevent invention can maintain a certain degree of adherence of the electrode to the scalp, even without sticking the electrode to the scalp with a paste, biosignals that are important for accurately determining the state of sleep can be acquired with a certain sensitivity.

In this way, a biosignal measurement device that can improve measurement accuracy without forcing an excessive burden on subjects can be realized.

Additional features and advantages of the present invention are described herein, and will be apparent from, the following Detailed Description and Figures.

BRIEF DESCRIPTION OF THE FIGSURES

FIG. 39 is a diagram schematically showing a hair band according to another embodiment, and its attached state.

FIG. 45 is a diagram schematically showing electrode placements according to another embodiment.

FIG. 54 is a graph showing experimental results.

FIG. 55 is a graph showing experimental results.

DETAILED DESCRIPTION

Hereinbelow, modes for carrying out the present invention will be described. It should be noted that the description will be given in the following order.
<1. First Embodiment>
[1-1. Configuration of Biosignal Measurement Device]
[1-2. Attachment Procedure]
[1-3. Configuration of Measurement Section]
<2. Second Embodiment>
[2-1. Configuration of Biosignal Measurement Device]
[2-2. Attachment Procedure]
<3. Third Embodiment>
[3-1. Configuration of Biosignal Measurement Device]
[3-2. Attachment Procedure]
[3-3. Configuration of Measurement Section]
<4. Other Embodiments>
<1. First Embodiment>
[1-1. Configuration of Biosignal Measurement Device]

Figure 1:
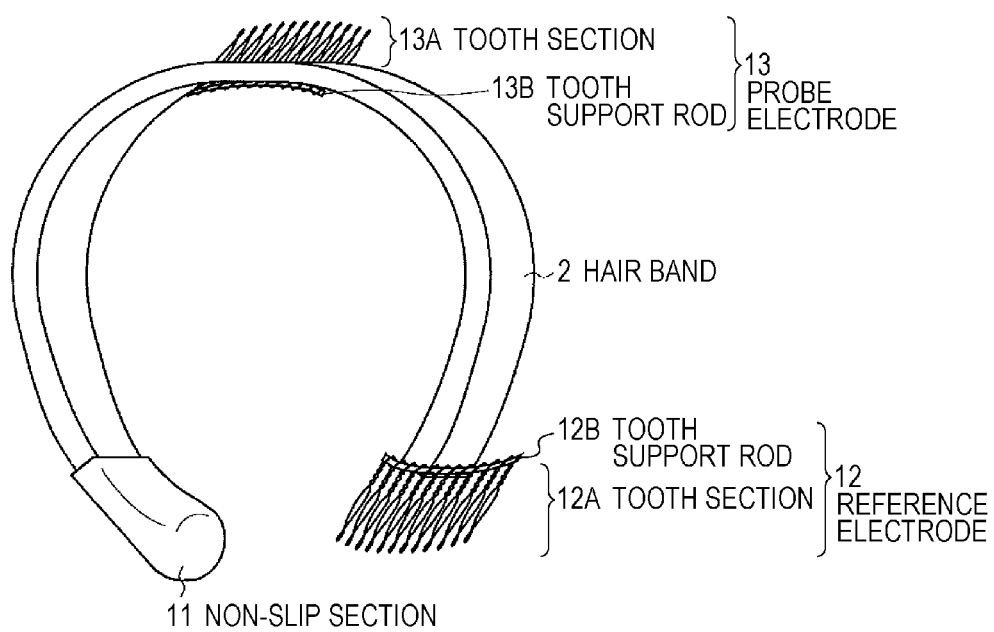
FIG. 1 is a diagram schematically showing the configuration of a biosignal measurement device according to a first embodiment.

FIG. 1 shows the configuration of a biosignal measurement device 1. The biosignal measurement device 1 has a support (hereafter, this will be also referred to as hair band) 2 that can be supported on the head. The hair band 2 is made of a plate-like plastic material or metallic material having elasticity, and is formed in a C-shape.

A non-slip section 11 made of a material such as rubber is provided at one end of the hair band 2. The non-slip section 11 is curved at its distal end, making it possible to prevent biting into the head.

Figure 2:
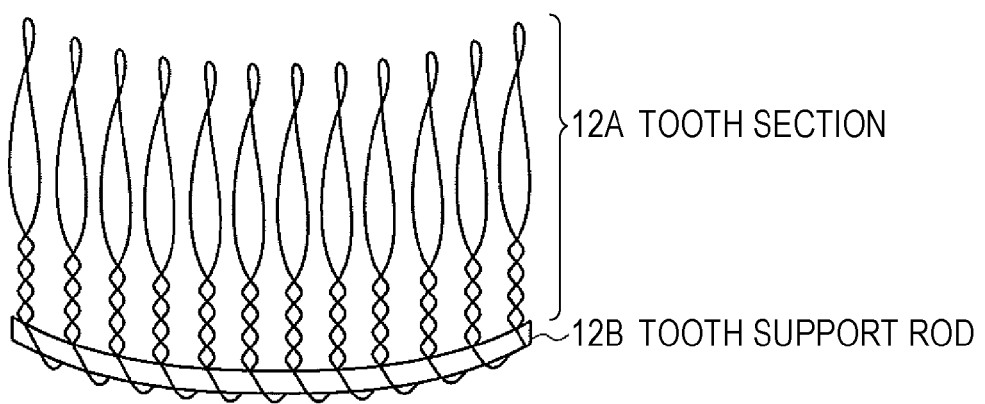
FIG. 2 is a diagram schematically showing the configuration of a reference electrode.

On the other hand, a reference electrode 12 is provided at the other end of the hair band 2. As shown in FIG. 2, the reference electrode 12 includes a section (hereinafter, this will be also referred to as a tooth section) 12A in which a plurality of teeth each made of a conductor are arranged in a line, and a rod-like section (hereinafter, this will be also referred to as a tooth support rod) 12B that supports the tooth section 12A.

The teeth of the tooth section 12A are made of conductive linear members, which are formed in an annular shape on the tooth tip side from a predetermined position between their middle and roots, and on the root side from the predetermined position, are wound in opposite directions in a mutually contacting state into a rod-like shape and fixed to the tooth support rod 12B while keeping regular intervals between adjacent teeth.

The tooth support rod 12B is made of a non-flexible conductor that is thicker than the linear members in the tooth section 12A. The tooth support rod 12B is attached at the other end of the hair band 2, with the tips of the teeth of the tooth section 12A pointing in the same direction as the direction pointing from the middle of the hair band 2 toward the distal end. Also, the tooth support rod 12B is curved to the non-slip section 11 side of the hair band 2 to an extent that conforms to the shape on the head side.

On the other hand, a probe electrode 13 is provided in the middle of the hair band 2. The probe electrode 13 includes a tooth section 13A and a tooth support rod 13B that are of the same structure as the reference electrode 12. The tooth support rod 13B is attached in the middle portion of the hair band 2, with the tips of the teeth of the tooth section 13A pointing in the plane of the top portion of the curve of the hair band 2 and in a direction orthogonal to the direction pointing from the middle toward the distal end.

[1-2. Attachment Procedure]

Next, an attachment procedure for the biosignal measurement device 1 will be described. In a first step, the hair band 2 is put over until its back surface comes into contact with the area between the vertex and the forehead. The hair band 2 is formed in a C-shape having elasticity (see FIG. 1), and thus can clamp the head with a predetermined force applied in a direction in which its both ends approach each other. Therefore, displacement of the hair band 2 itself with respect to the head can be reduced.

On the one hand, the reference electrode 12 provided at the other end of the hair band 2 is attached with the tips of the teeth of the tooth section 12A pointing in the same direction as the direction pointing from the middle of the hair band 2 toward the distal end, and the structure of the tooth section 12A is such that a plurality of teeth are arranged in a line (see FIG. 1). Thus, when the hair band 2 is put over the head, the teeth can be smoothly inserted in the roots of head hair.

On the other hand, the tooth tip side of the tooth section 12A from a predetermined position between the middle and roots of the teeth is formed in an annular shape by linear members (see FIG. 2). Thus, the teeth in the hair band 2 are twisted around the roots of head hair, which can improve adherence of the teeth to the scalp and also reduce displacement in comparison to point contact. In addition, pain caused to the subject can be lessened for improved attachment comfort.

In a second step, the hair band 2 in contact with the area between the vertex and the forehead is slid to the vertex position. The probe electrode 13 provided in the middle of the hair band 2 is attached with the tips of the teeth of the tooth section 13A pointing in the plane of the top portion of the curve of the hair band 2 and in a direction orthogonal to the direction pointing from the middle toward the distal end (see FIG. 1). Thus, when the hair band 2 is slid to the vertex position, the teeth can be smoothly inserted in the roots of head hair.

Also, the tooth tip side of the tooth section 13A from a predetermined position between the middle and roots of the teeth is formed in an annular shape by linear members (see FIG. 2). Thus, the teeth in the hair band 2 are twisted around the roots of head hair, which can improve adherence to the scalp and also reduce displacement in comparison to point contact.

Figure 3:
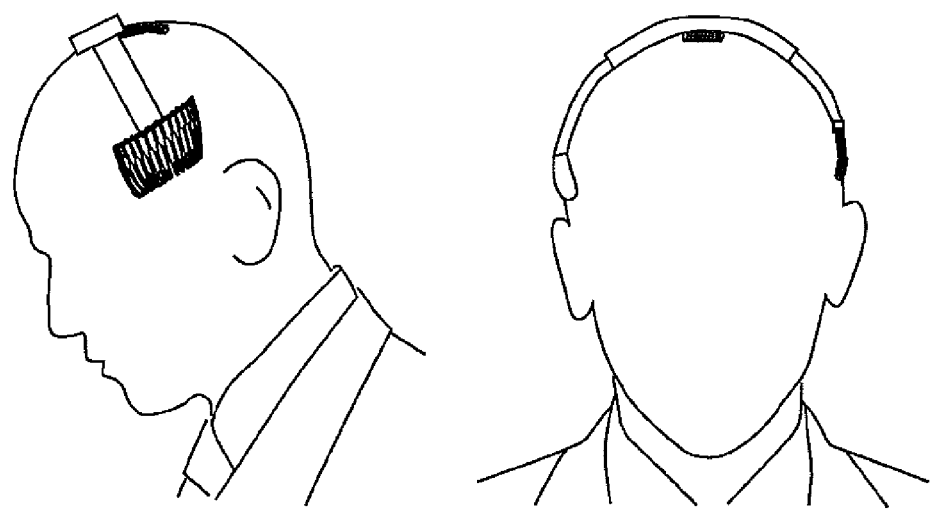
FIG. 3 is a diagram schematically showing the attached state of a biosignal measurement device.

Through the above attachment procedure, for example, as shown in FIG. 3, the biosignal measurement device 1 is attached to the head, and the reference electrode 12 and the probe electrode 13 are fixed to the scalp.

Because the reference electrode 12 is formed by arranging a plurality of linear teeth arranged in a line, the reference electrode 12 is extremely thin. Therefore, even when the reference electrode 12 is positioned between the pillow and the subject, the feeling of discomfort caused by the presence of the reference electrode 12 can be reduced. On the other hand, the vertex where the probe electrode 13 is positioned is a part that makes hardly any contact with the pillow even when the subject tosses and turns in bed during normal sleep, the feeling of discomfort caused by the presence of the probe electrode 13 can be reduced.

Also, the portions of the tooth sections 12A and 13A in the reference electrode 12 and the probe electrode 13 which are located on the root side from a predetermined position between their middle and roots are wound in opposite directions in a mutually contacting state into a rod-like shape and fixed to the tooth support rods 12B and 13B (see FIG. 2). That is, since the linear teeth are fixed to the tooth support rod 12B at a single point, the teeth can uniformly move around isotropically about the fixed point as the center. This ensures flexible adaptation no matter from which direction a force is applied due to tossing and turning in bed or the like, and enables a quick return to the original state once the force disappears.

Therefore, the biosignal measurement device 1 can significantly reduce sleep impairment for the subject. Also, as compared with polysomnography that involves a large number of attachments to a subject, burden on the subject can be lessened without compromising attachment comfort for the subject.

Incidentally, the electrodes 12 and 13 in the biosignal measurement device 1 are supported by the hair band 2. Therefore, the biosignal measurement device 1 can prevent, for example, dropping of the electrodes during attachment and detachment, and also allows the wiring connected to the electrodes 12 and 13 to be placed inside the hair band 2. As a result, the biosignal measurement device 1 can avoid, for example, loss of electrodes during attachment and detachment, or entanglement with cords, thereby improving usability.

It should be noted that the attachment sequence described above is only an example, and this attachment sequence is not limitative.

[1-3. Configuration of Measurement Section]

Figure 4:
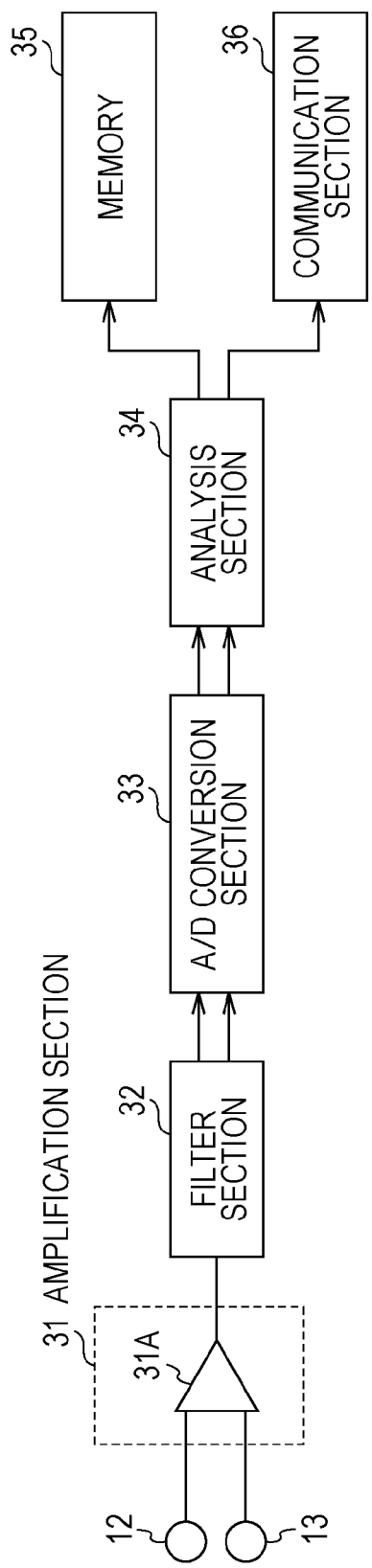
FIG. 4 is a diagram schematically showing the circuit configuration of a measurement section.

FIG. 4 shows the configuration of a measurement section that measures a biosignal sensed by each of the reference electrode 12 and the probe electrode 13. A circuit board and the like in the measurement section are provided in the surface or in the inside of the hair band 2, for example.

This measurement section 30 includes an amplification section 31, a filter section 32, an A(Analog)/D(Digital) conversion section 33, an analysis section 34, a memory 35, and a communication section 36.

The measurement section 30 is configured to supply source voltage from a battery or the like to each of these sections 31 to 36 upon receiving a measurement start command from an operating section provided in the surface of the hair band 2, for example, and to shut off the supply of source voltage upon receiving a measurement stop command from the operating section.

The amplification section 31 has a differential amplifier 31A. The differential amplifier 31A amplifies the potential difference between the reference electrode 12 and the probe electrode 13 as a signal (hereinafter, this will be also referred to as bio-waveform signal), and outputs the amplified bio-signal to the filter section 32. Since the probe electrode 13 is an electrode placed at the vertex position, the bio-waveform signal outputted from the differential amplifier 31A is a signal that mainly reflects brain waves.

As described above, the structure of the reference electrode 12 and probe electrode 13 are such that reduces displacement while improving adherence of the tooth sections 12A and 13A to the scalp. Thus, even without sticking the electrodes to the scalp with a paste, the amplification section 31 can accurately amplify potential difference within the living body, and sensitivity in the measurement section is improved as a result.

Furthermore, the head-side position where the reference electrode 12 is positioned, and the vertex position where the probe electrode 13 is positioned are both positions on the skull. Therefore, the bio-waveform signal obtained from each of the reference electrode 12 and the probe electrode 13 accommodates reduced myoelectric components, thereby improving sensitivity to brain waves.

Frequency bands corresponding to brain waves are set in the filter section 32. The filter section 32 filters out signal components other than the frequency bands being set, from a bio-waveform signal, and supplies the filtered bio-waveform signal to the A/D conversion section 33.

Incidentally, brain waves include delta wave (1 to 3 [Hz]), theta wave (4 to 7 [Hz]), alpha wave (8 to 13 [Hz]), beta wave (14 to 30 [Hz]), gamma wave (31 to 64 [Hz]), rho wave (129 to 512 [Hz]), and sigma wave (513 to 1024 [Hz]). Some or all of these are set so as to be variable with a predetermined operating section, as frequency bands corresponding to brain waves.

The A/D conversion section 33 converts the bio-waveform signal into digital data (hereinafter, this will be also referred to as bio-waveform data), and supplies the bio-waveform data to the analysis section 34.

The analysis section 34 includes a CPU, a ROM, a RAM serving as the work memory for the CPU, a speaker, and a clock (clocking section). In this ROM, a program for causing an analysis process to be executed, data indicating the level below which an electrode should be regarded as being not in contact with the surface of the human body (hereinafter, this will be also referred to as non-contact level threshold), and the like are stored.

Upon receiving a measurement start command, the analysis section 34 expands a program stored in the ROM to the RAM, and in accordance with the program, executes a process of analyzing whether or not an electrode is in contact (hereinafter, this will be also referred to as electrode contact detection process), and a waveform analysis process.

An example of specific details of this electrode contact detection process will be described. The analysis section 34 compares the average level of bio-waveform data for each specified period, with the non-contact level threshold that is set for this average.

If this level average is below the non-contact level threshold, the analysis section 34 discontinues processing by regarding that an electrode is not in contact with the human body surface, and notifies via a speaker that the electrode should be attached again.

In contrast, if the level average is above the non-contact level threshold, the analysis section 34 regards the electrode as being in contact with the human body surface, and stores the bio-waveform data for the corresponding specified period into the memory 35.

The electrode contact detection process is executed in this way. It should be noted, however, that the illustrated process is only an example.

Next, an example of specific details of the waveform analysis process will be described. That is, as a first stage, the analysis section 34 recognizes electroencephalogram waveform, electro-oculogram waveform, and electromyogram waveform components from bio-waveform data.

As described above, since the head-side position where the reference electrode 12 is positioned, and the vertex position where the probe electrode 13 is positioned are both positions on the skull, the bio-waveform signal accommodates reduced myoelectric components. Also, generally speaking, the waveform level of the bio-waveform signal becomes small in cases where a paste is used so that the electrode does not stick onto the scalp. However, it has been confirmed that electroencephalogram waveform, electro-oculogram waveform, and electromyogram waveform components can be obtained from the spectrum of bio-waveform data.

As a second stage, the analysis section 34 determines sleep-onset time by using the electroencephalogram waveform and the electro-oculogram waveform. Specifically, the sleep-onset time is determined as the point in time when conditions including disappearance of α-waves and occurrence of SEM (Slow Eye Movement) are satisfied.

As a third step, the analysis section 34 makes various kinds of determinations related to sleep by using the electroencephalogram waveform, the electro-oculogram waveform, and the electromyogram waveform. In this embodiment, the analysis section 34 makes a determination as to the depth and quality of non-REM sleep, and a determination as to the start time, end time, and quality of REM sleep.

The depth and quality of non-REM sleep are determined by using the number of occurrences of δ-waves per unit time (occurrence density), and the amplitude value of the δ-waves.

On the one hand, the start time of REM sleep is determined as the point in time when conditions including disappearance of δ-waves, occurrence of REM, and disappearance of myoelectric potential are satisfied, and the end time of REM sleep is determined as the point in time when conditions including disappearance of REM and occurrence of myoelectric potential are satisfied.

On the other hand, the quality of REM sleep is determined by using the number of occurrences (occurrence density) of REM per unit time from the start time to the end time of REM sleep.

As a fourth stage, the analysis section 34 determines awakening time by using the electroencephalogram waveform and the electromyogram waveform. Specifically, the awakening time is determined as the point in time when conditions including occurrence of β-waves and occurrence of myoelectric potential are satisfied.

As a fifth stage, the analysis section 34 determines cycle pattern by using the numbers of occurrences, proportions, occurrence cycles, etc. of non-REM sleep and REM sleep.

As a sixth stage, the analysis section 34 generates the determination results in the respective steps, and parameters (determination elements) used for the determinations as data (hereinafter, this will be also referred to as determination result data), and stores the data into the memory 35 in association with the bio-waveform data.

The waveform analysis process is executed in this way. It should be noted, however, that the illustrated process is only an example.

The memory 35 is configured to execute a write process or a readout process in accordance with a command supplied from the analysis section 34 or the communication section 36. It should be noted that the memory 35 is not limited to one that is built in the measurement section 30, but a removable memory such as a USB memory, an SD card memory, or a CF card memory can be employed.

When a transmit command is given from the operating section, the communication section 36 is configured to transmit various kinds of data stored in the memory 35 to predetermined external equipment by, for example, radio communication.

<2. Second Embodiment>

[2-1. Configuration of Biosignal Measurement Device]

Figure 5:
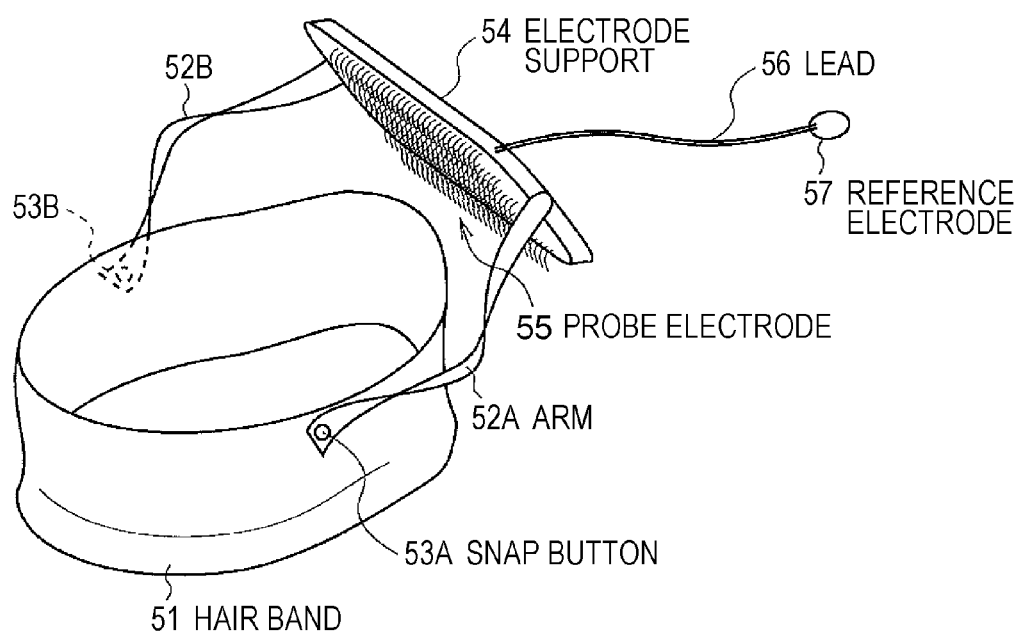
FIG. 5 is a diagram schematically showing the configuration of a biosignal measurement device according to a second embodiment.

FIG. 5 shows the configuration of a biosignal measurement device 50. The biosignal measurement device 50 has a support (hereafter, this will be also referred to as hair band) 51 that can be supported on the head. The hair band 51 is made of a cloth material or rubber material, and formed in a belt shape or annular shape.

A plate-like or linear arm 52 (52A, 52B) made of a material having flexibility such as rubber is attached at a position facing the hair band 51, by a coupling member that is detachable from the arm 52. A plate-like electrode support 54 is coupled to the distal end of the arm 52.

For example, a snap button 53 (53A, 53B) is employed as the coupling member in this embodiment. The length of the arm 52 is set shorter than the linear distance between the position of the snap button 53 where the hair band 51 is to be attached, and the position where the electrode support 54 is to be attached.

A probe electrode 55 is provided on one surface of the electrode support 54. Also, at a predetermined position on the surface of the electrode support 54, a lead 56 is extended from inside the electrode support 54. A reference electrode 57 is provided at the distal end of the lead 56.

Figure 6:
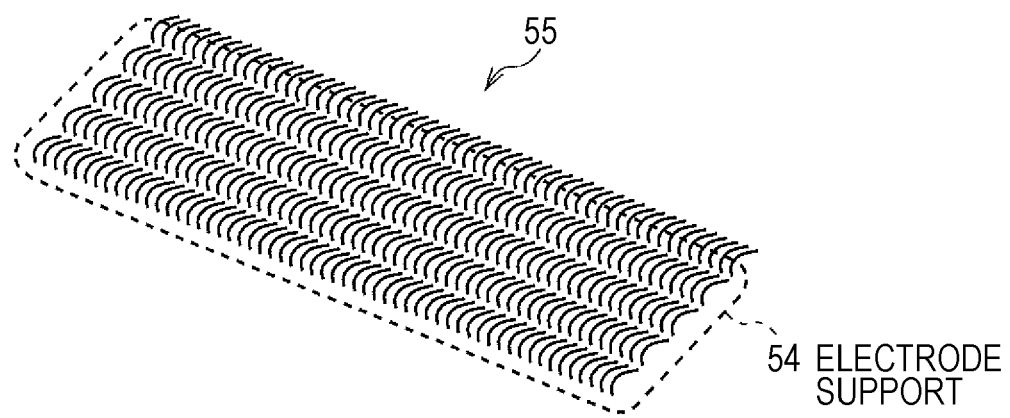
FIG. 6 is a diagram schematically showing the configuration of a probe electrode.

As shown in FIG. 6, the structure of the probe electrode 55 is such that a plurality of teeth each made of a conductive linear member are arranged at regular intervals in the row direction and the column direction. These teeth are each bent at a predetermined position between its root and distal end, and the distal end has a rounded shape. The bending angle is set approximately to the sum of 90[°] and several degrees so that the tooth portion from the tooth tip to the bending position becomes oblique to the tooth portion from the tooth root to the bending position.

Figure 7:
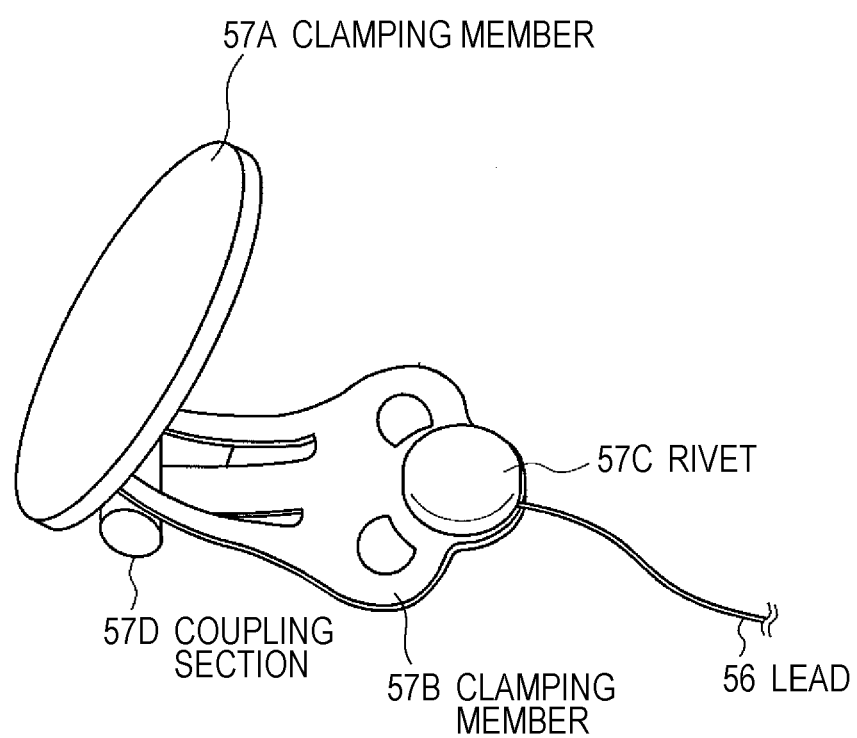
FIG. 7 is a diagram schematically showing the configuration of a reference electrode.

As shown in FIG. 7, the reference electrode 57 includes a coin-shaped clamping member 57A having approximately the same surface area as the earlobe, a clamping member 57B coupled to the clamping member 57A, and a river 57C provided on the surface of the clamping member 57B facing the clamping member 57A.

At a coupling section 57D of the clamping member 57A and the clamping member 57B, the clamping member 57A and the clamping member 57B are coupled so as to be movable away from or toward each other with the connecting section 57D as an axis. The distal end of the lead 56 is electrically and mechanically fixed in place between the rivet 57C and the clamping member 57B.

[2-2. Attachment Procedure]

Next, an attachment procedure for the biosignal measurement device 50 will be described. In a first step, the hair band 51 is attached around the head.

In a second step, the electrode support 54 coupled to the hair band 51 via the arm 52 is attached to the vertex. Specifically, the electrode support 54 is placed at the vertex position with its surface having the probe electrode 55 facing the head, and is thereafter slid in the same direction as the direction of the tooth tip in the probe electrode 55.

The arm 52 is made of a material having flexibility such as rubber, and the length of the arm is set shorter than the linear distance between the position of the snap button 53 at a position where the hair band 51 is to be attached, and the distance where the electrode support 54 is to be attached. Therefore, when the electrode support 54 is attached to the vertex, the force exerted as the arm 52 tries to return to the original arm length acts on the electrode support 54 as a force that presses the electrode support 54 against the vertex, thereby adhering the probe electrode 55 provided on the electrode support 54 to the scalp.

Also, the plurality of linear teeth forming the probe electrode 55 are each bent at a predetermined position between its root and distal end, and the distal end has a rounded shape (see FIG. 6). Therefore, when sliding the electrode support 54, the teeth can be smoothly inserted in the roots of head hair, without the teeth scratching the scalp. In addition, as the electrode support 54 is slid, the teeth of the probe electrode 55 are twisted around the roots of head hair. Thus, in comparison to the case of adopting teeth that are not bent, adherence of the probe electrode 55 to the scalp can be improved, and also its displacement can be reduced.

On the other hand, since the vertex where the probe electrode 55 is positioned is a part that makes hardly any contact with the pillow even when the subject tosses and turns in bed during normal sleep, the feeling of discomfort caused by the presence of the probe electrode 55 can be reduced, and also displacement of the probe electrode 55 due to the tossing and turning in bed can be avoided.

Therefore, the biosignal measurement device 50 can significantly reduce sleep impairment for the subject. Also, as compared with polysomnography that involves a large number of attachments to the subject, burden on the subject can be lessened without compromising attachment comfort for the subject.

In a third step, the reference electrode 57 is attached to the earlobe. Specifically, the earlobe is clamped by the coin-shaped clamping member 57A, and the rivet 57C (see FIG. 7) provided on the clamping member 57B. Since the earlobe is clamped by the clamping member 57A and the rivet 57C that are rounded portions, pain caused to the subject can be mitigated, thereby making it possible to significantly reduce sleep impairment for the subject as a result.

Figure 8:
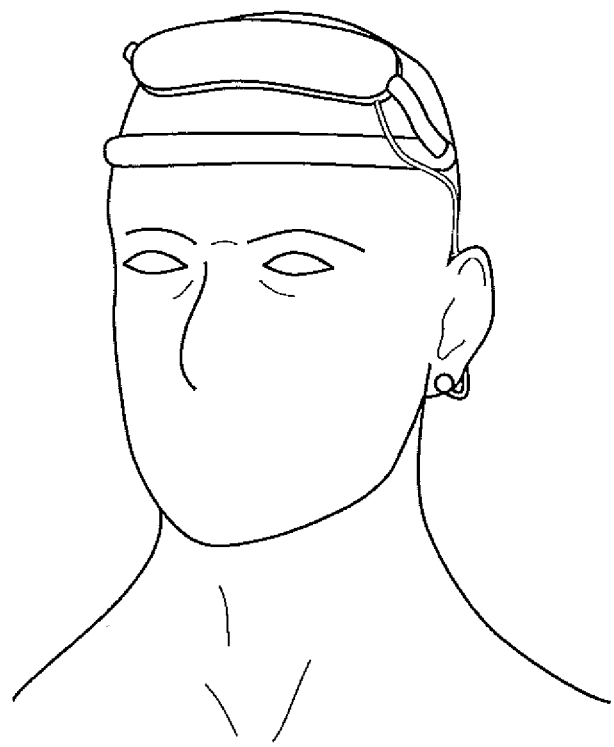
FIG. 8 is a diagram schematically showing the attached state of a biosignal measurement device.

Through the above attachment procedure, for example, as shown in FIG. 8, the biosignal measurement device 50 is attached to the head, with the probe electrode 55 and the reference electrode 57 fixed to the scalp and the earlobe, respectively. It should be noted, however, that the attachment sequence described above is only an example, and this attachment sequence is not limitative.

Incidentally, a measurement section in the biosignal measurement device 50 is provided in the surface or in the inside of the electrode support 54, for example. Since the configuration of this measurement section is the same as that of the measurement section in the biosignal measurement device 1, description thereof is omitted here.

It should be noted that the structure of the probe electrode 55 is such that reduces displacement while improving adherence of the teeth to the scalp. Thus, even without sticking the electrode to the scalp with a paste, the measurement section can accurately amplify potential difference within the living body, and sensitivity in the measurement section is improved as a result.

Also, the vertex position where the probe electrode 55 is positioned is a position on the skull. On the other hand, the reference electrode 57 is positioned on the earlobe having no muscle. Therefore, myoelectric components are reduced in the phase difference obtained from the probe electrode 55 and the reference electrode 57, thereby improving sensitivity to brain waves.

Further, the earlobe on which the reference electrode 57 is positioned is located relatively far from the head. Thus, the behavior of the brain between the earlobe position and the vertex position where the probe electrode 55 is positioned can be directly grasped as the potential difference between the probe electrode 55 and the reference electrode 57.

It should be noted that the probe electrode 55 and the reference electrode 57 are supported to the hair band 51 via the arm 52 and the electrode support 54. Therefore, the biosignal measurement device 50 can prevent, for example, dropping of the electrodes during attachment and detachment, and also allows the wiring connected to the electrodes 55 and 57 to be placed inside the hair band 51. As a result, the biosignal measurement device 50 can avoid, for example, loss of electrodes during attachment and detachment, or entanglement with cords, thereby improving usability.

Also, the arm 52 and the electrode support 54 can be removed via the snap button 53. Therefore, the biosignal measurement device 50 allows the hair band 51 to be cleaned, or to be simply used as a hair clip or a protection against cold.

<3. Third Embodiment>
[3-1. Configuration of Biosignal Measurement Device]

A biosignal measurement device according to a third embodiment includes a head device 300 (FIGS. 9 to 16), and a chin device 500 (FIGS. 19 to 22).

The head device 300 has a support (hair band) 310 that can be supported on the head. The hair band 310 is made of a plate material having bendability and rigidity such as plastic or metal, and is formed in a C-shape. Therefore, the hair band 310 can flexibly fit any head shape, and retain that state.

To allow visual recognition that one end is the forehead side and the other end is the occipital side, the hair band 310 is formed with the one end (hereinafter, this will be also referred to as front end) positioned higher than the other end (hereinafter, rear end) (see FIG. 10 and FIG. 11).

That is, the cross-section of the hair band 310 is asymmetrical from front to back about a perpendicular passing the center in the lengthwise direction and widthwise direction of the hair band 310 as the boundary, and the length of the hair band 310 from the center to the front end is shorter than the length of the hair band 310 from the center to the rear end.

Also, the width of the hair band 310 is set smaller than the distance between a straight line connecting "F3" and "P3" in the international 10-20 system, and a straight line connecting "F4" and "P4". Specifically, the width is preferably not larger than 25 [mm]. Therefore, the hair band 310 can flexibly fit the contour portion passing the median plane, while leaving the lateral portion of the head open.

Figure 9:
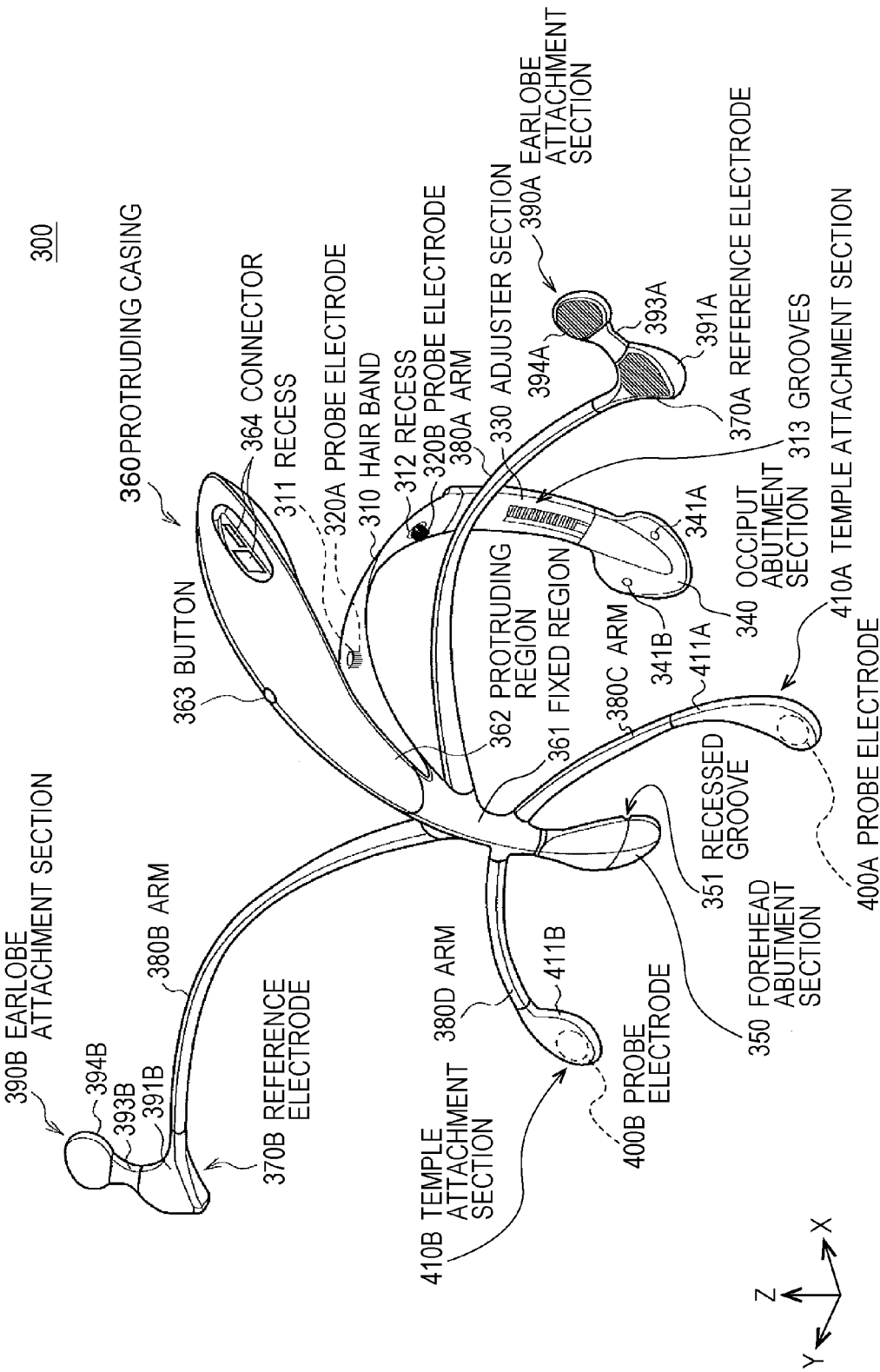
FIG. 9 is a diagram schematically showing a head device (perspective).

In the inner surface of the hair band 310, recesses (depressions) 311 and 312 are provided in the middle position of the hair band 310 at a predetermined interval from each other (see FIG. 9). This interval is set as, for example, the average distance between the median central (Cz in the international 10-20 system) and the median parietal (Pz in the international 10-20 system) in an adult, with the front end taken as a reference.

Figure 10:
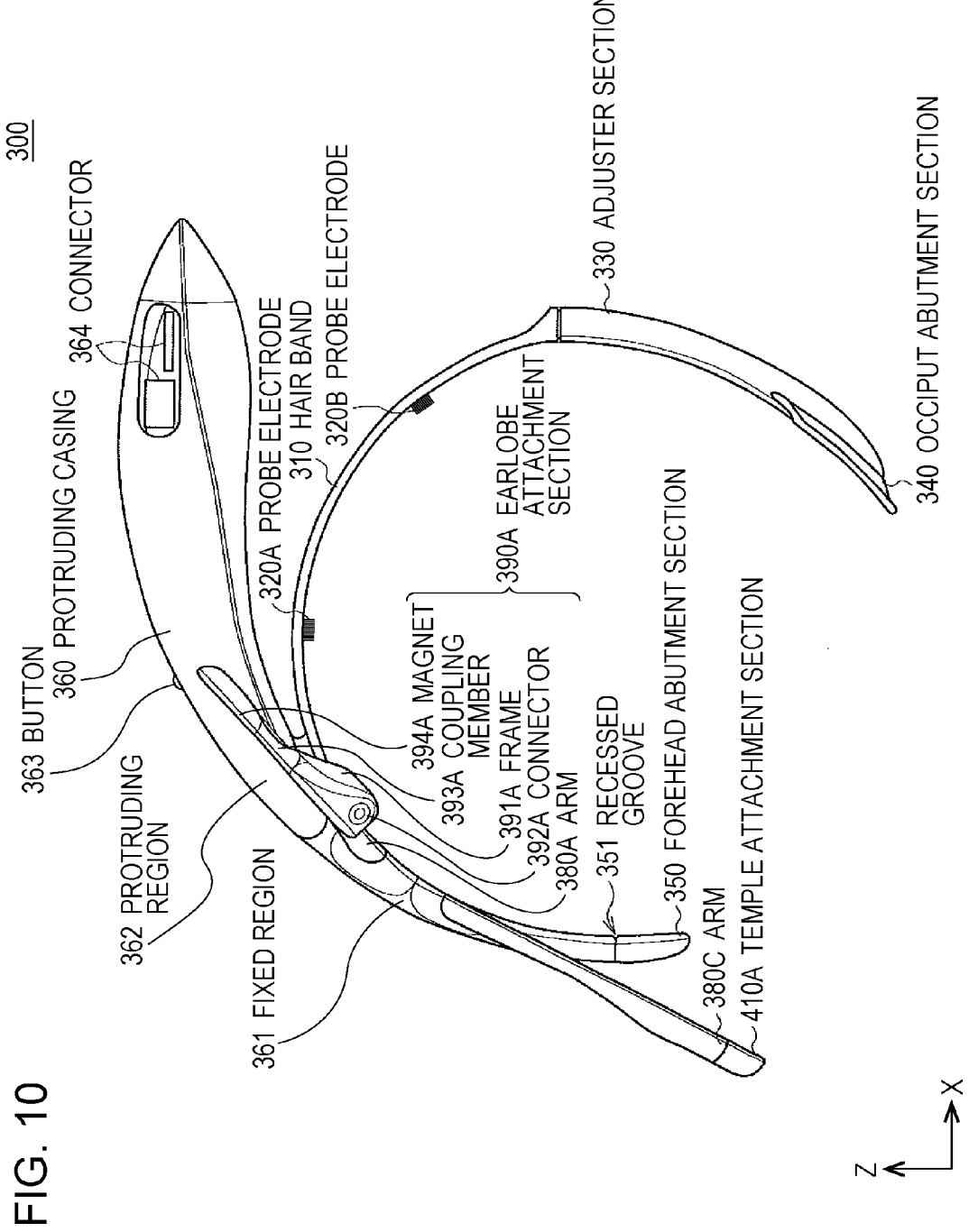
FIG. 10 is a diagram schematically showing a head device (left side).
Figure 11:
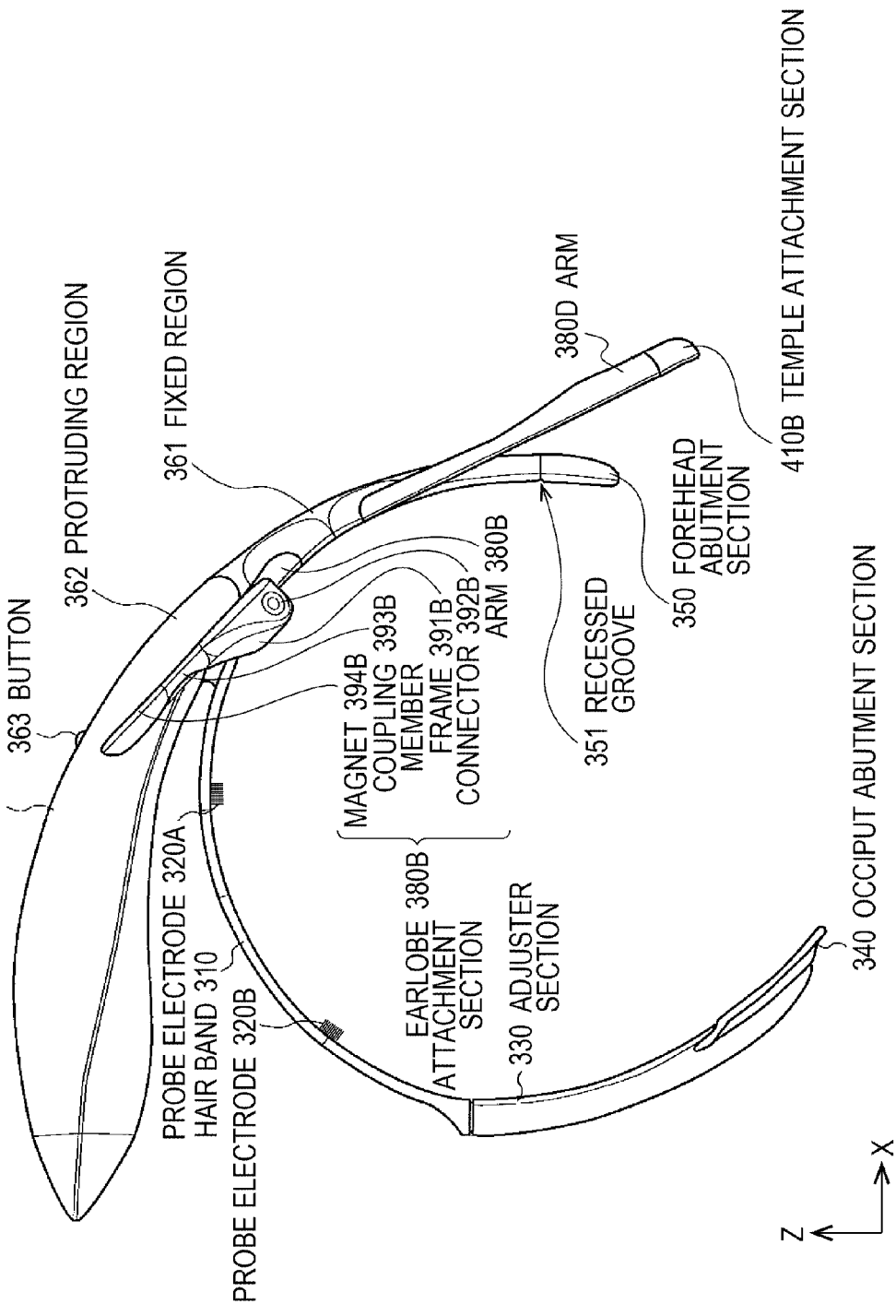
FIG. 11 is a diagram schematically showing a head device (right side).
Figure 12:
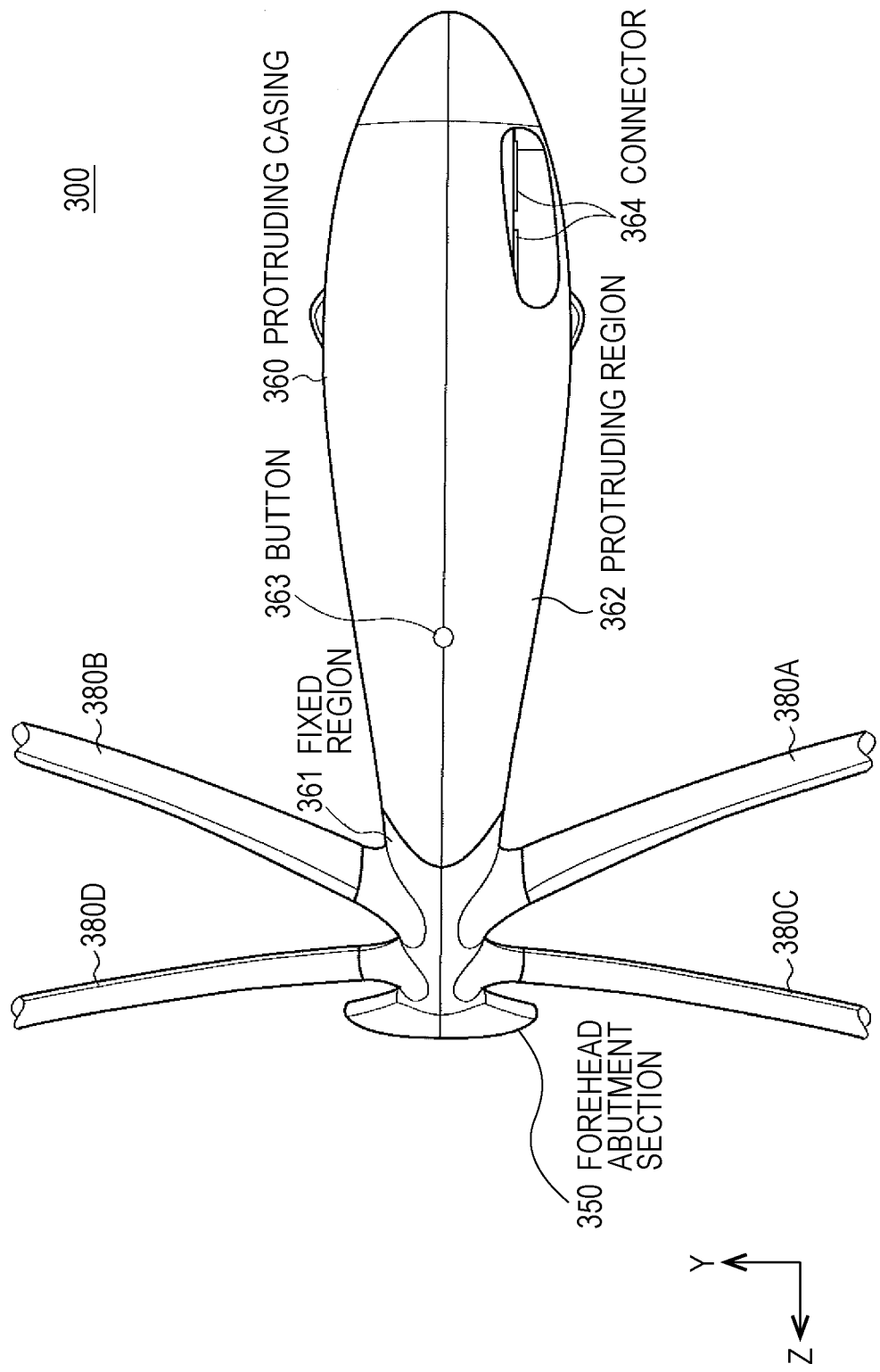
FIG. 12 is a diagram schematically showing a head device (top).
Figure 13:
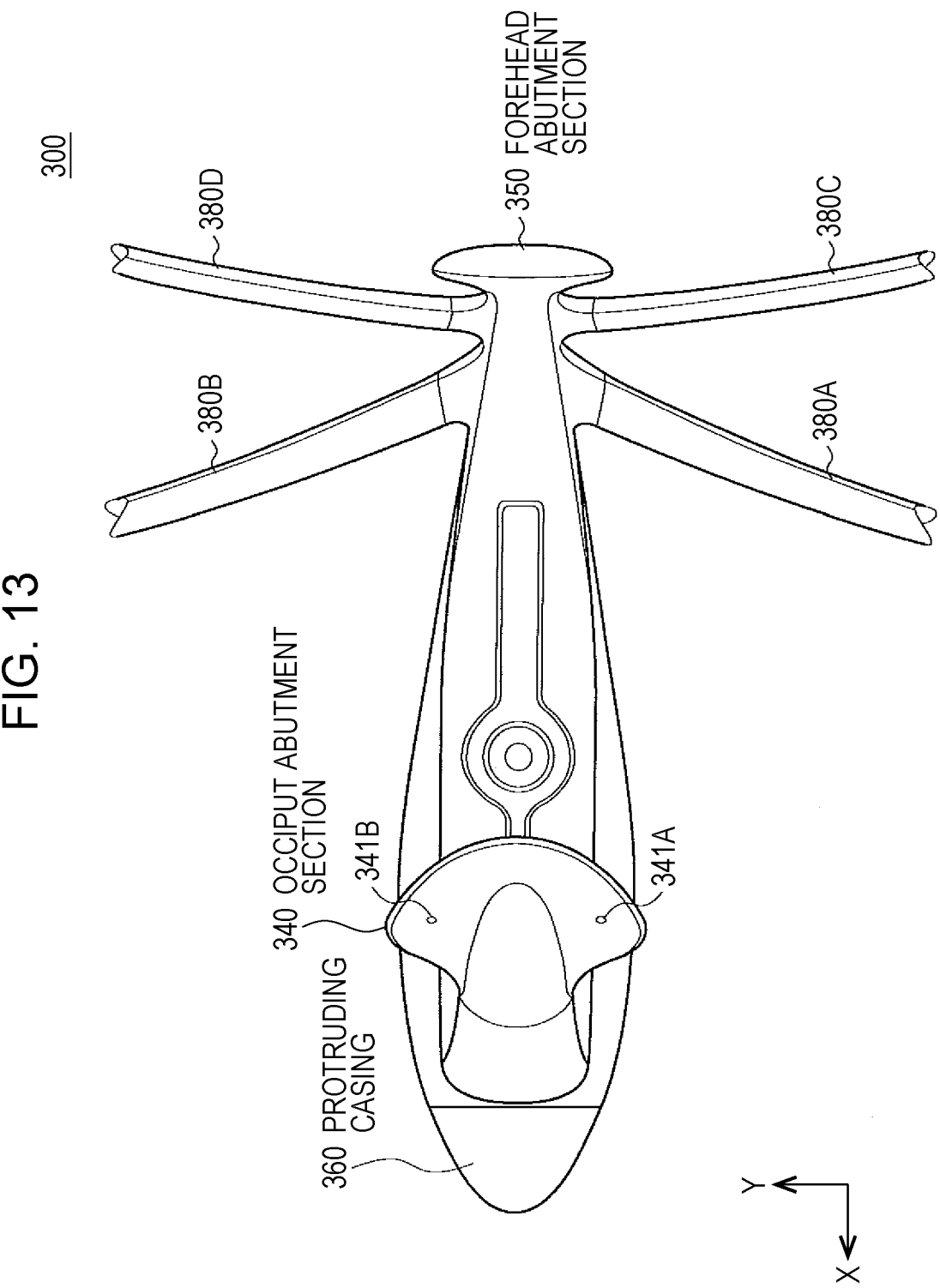
FIG. 13 is a diagram schematically showing a head device (bottom).
Figure 14:
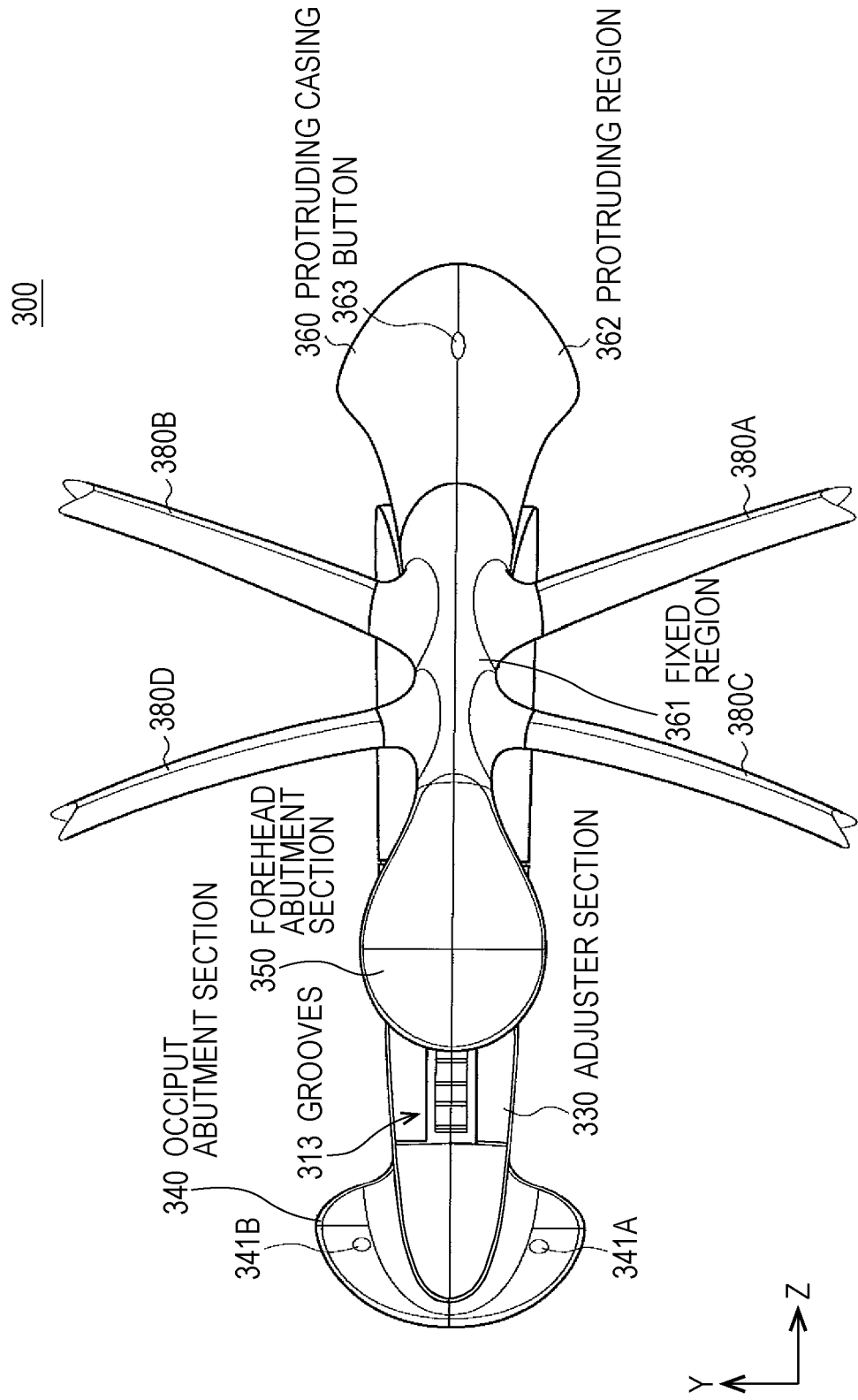
FIG. 14 is a diagram schematically showing a head device (front).
Figure 15:
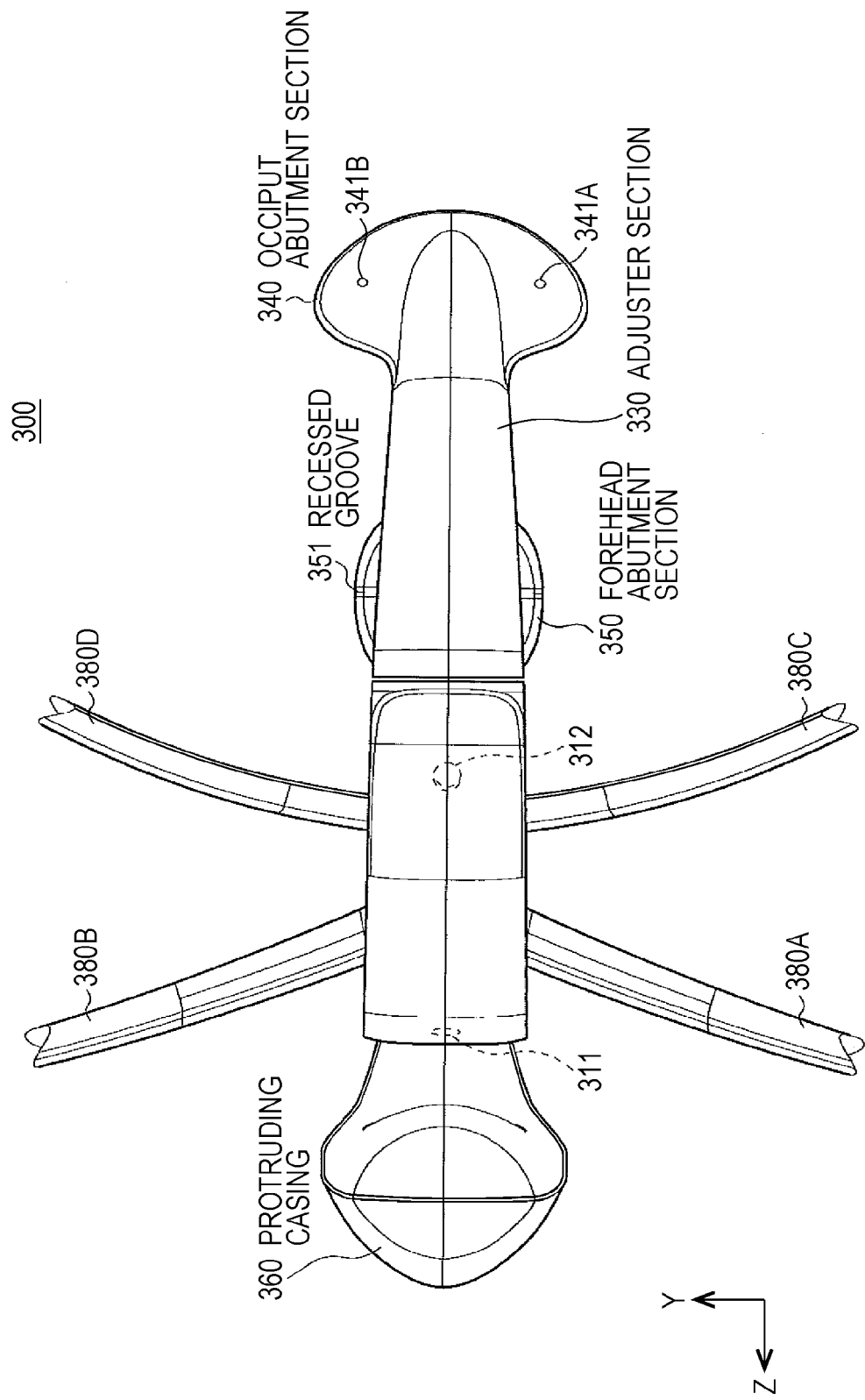
FIG. 15 is a diagram schematically showing a head device (rear).
Figure 16:
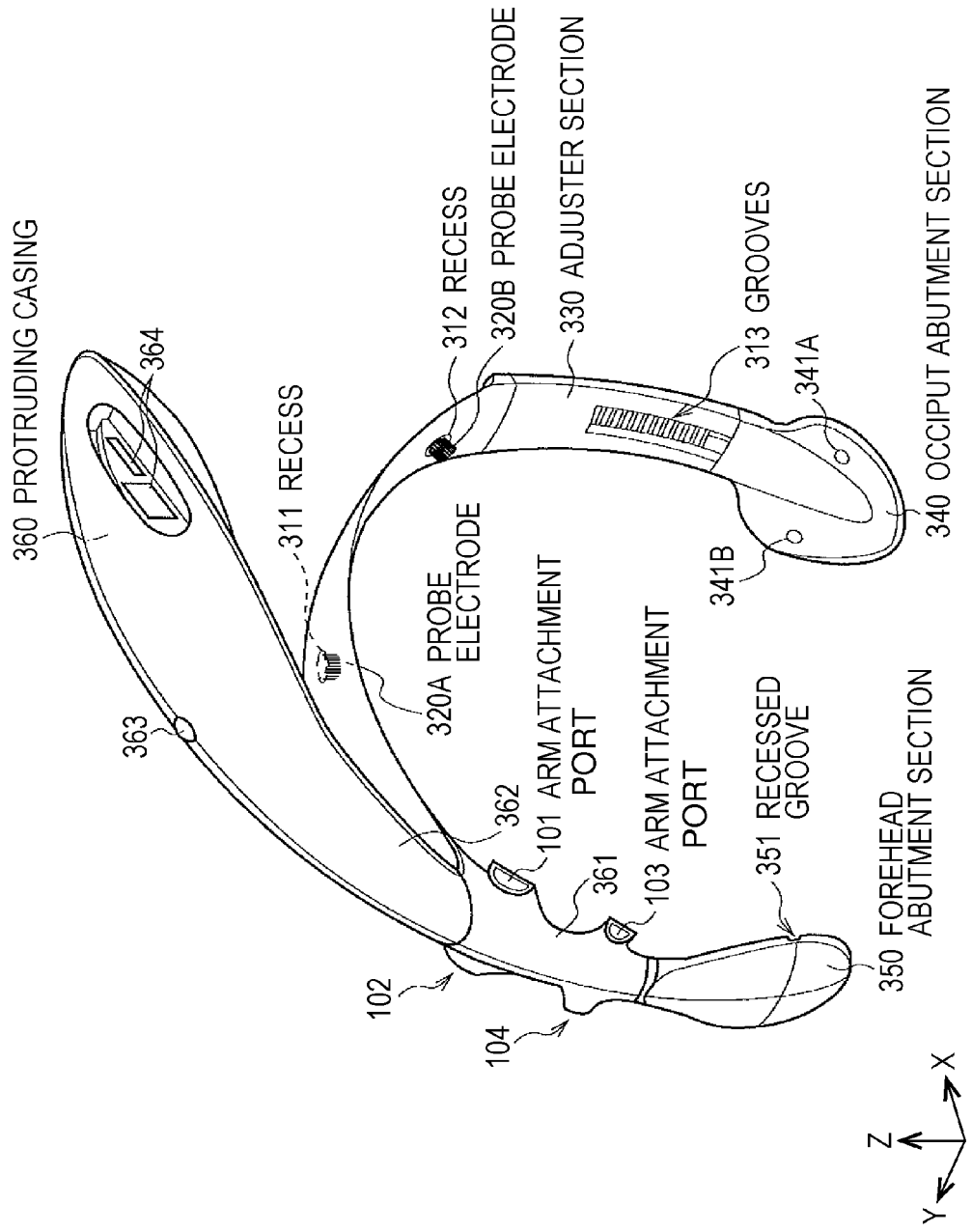
FIG. 16 is a diagram schematically showing a head device with arms detached.
Figure 17:
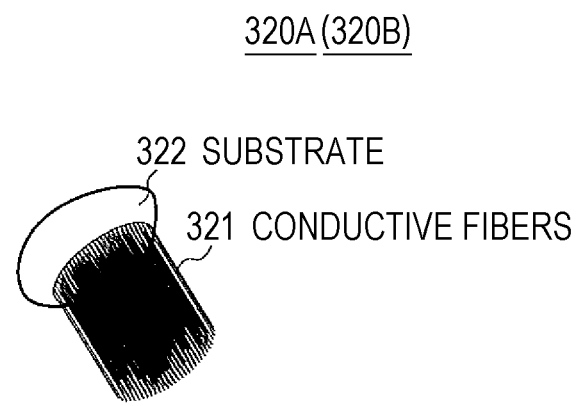
FIG. 17 is a diagram schematically showing the configuration of a probe electrode.

Probe electrodes 320A and 320B are provided in the recesses 311 and 312 (see FIG. 9 to FIG. 11). As shown in FIG. 17, the probe electrodes 320A and 320B are of a brush structure having a plurality of conductive fibers 321 implanted upright at predetermined intervals on a substrate 322 in the horizontal direction and the vertical direction.

The material of the conductive fibers 321 is, for example, carbon, amorphous carbon, stainless steel, or Thunderon® (copper sulfide chemically bonded to acrylic fibers and nylon fibers). The thickness (fiber thickness) or length of the conductive fibers 321 is such that the conductive fibers 321 have flexible rigidity without causing pain to the subject. In this embodiment, the thickness of the conductive fibers 321 is set to 25 [μm], and the length of the conductive fibers 321 is set to 10 [mm].

The substrate 322 is fixed to the bottom of the recesses 311 and 312. It should be noted that the implantation area of the conductive fibers 321, and the surface area of the recesses 311 and 312 are each set so as not to impair the mobility of the conductive fibers 321. Also, the length of the conductive fibers 321 and the depth of the recesses 311 and 312 are each set so that the distal ends of the conductive fibers 321 project from the inner surface of the hair band 310 to an extent that does not impair the fitting of the hair band 310 to the head.

Between the recess 312 and the rear end of the hair band 310, a plurality of grooves 313 are formed at predetermined intervals in the lengthwise direction of the hair band 310 (see FIG. 9). In the portion where the grooves 313 are formed, there is provided an adjuster section 330 that can slide in the lengthwise direction of the hair band 310 with this portion as a core (see FIG. 9 to FIG. 11, and FIG. 14 to FIG. 16).

The portion of the inner surface of the adjuster section 330 facing the grooves 313 of the hair band 310 is provided with a claw (not shown) that can be fitted in each of the grooves 313, allowing stepwise adjustment of the hair band 310 along its full length. Therefore, the attachment of the hair band 310 is improved in conformity to the dimensions and shape of the head.

The difference between the full length of the hair band 310 when the claw is fitted in a groove 313A (FIG. 18) of the grooves 313 which is closest to the front end, and the full length of the hair band 310 when the claw is fitted in a groove 313B (FIG. 18) that is farthest away is set to 30 [mm] in this embodiment.

Also, in this embodiment, with a groove 313C (FIG. 18) in the middle of the grooves 313 taken as a reference, the length of the adjuster section 330 with respect to the groove 313C in the middle is set to such a length that the open end of the adjuster section 330 when the claw is fitted in the groove 313C in the middle is located directly above the midline occipital (Oz in the international 10-20 system).

Therefore, since the open end of the adjuster section 330 can be so placed as to avoid contact of the distal end portion of the adjuster section 330 with the projecting portion of the head, pain caused to the subject during sleep is mitigated, thereby making it possible to significantly reduce sleep impairment for the subject as a result.

Figure 18:
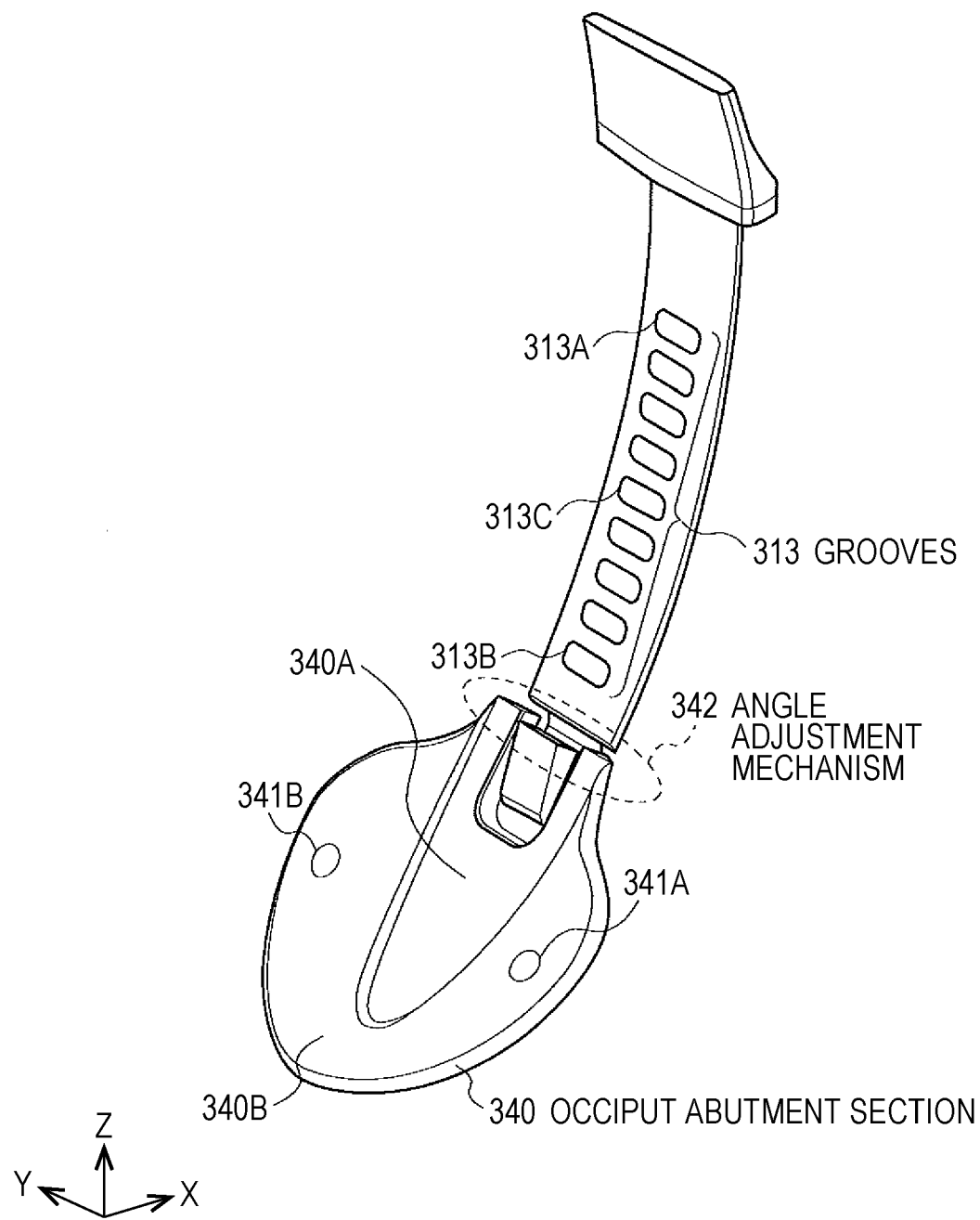
FIG. 18 is a diagram showing details of the rear end of a hairband.
Figure 19:
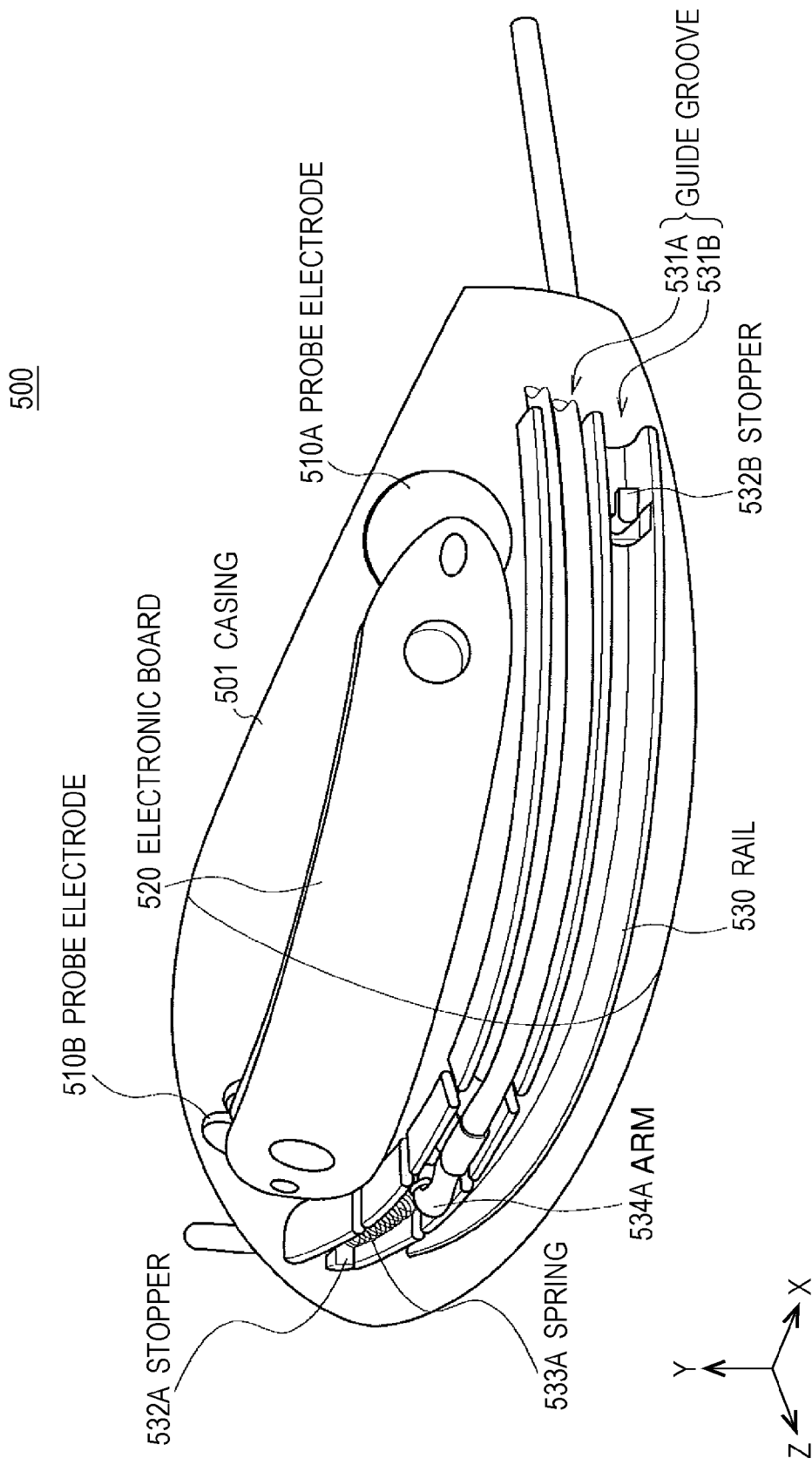
FIG. 19 is a diagram schematically showing a chin device (perspective).
Figure 20:
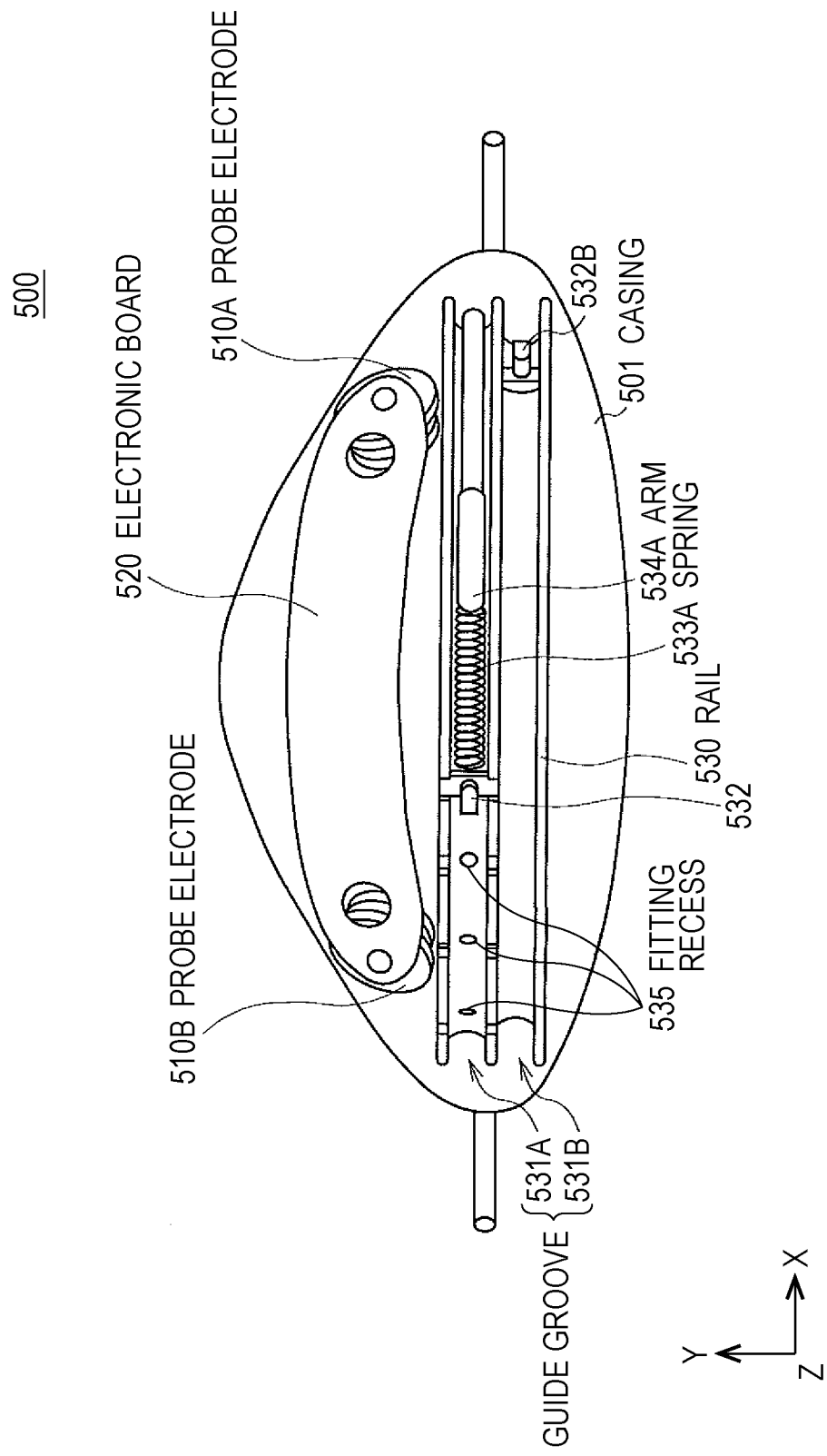
FIG. 20 is a diagram schematically showing a chin device (front).
Figure 21:
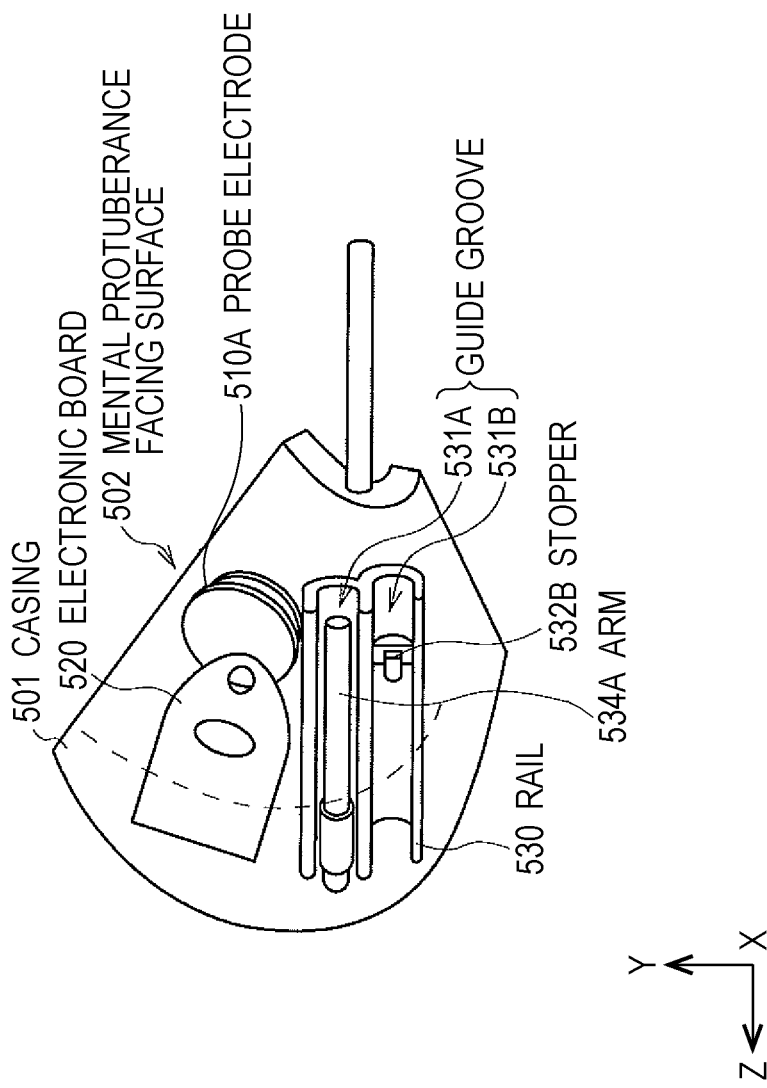
FIG. 21 is a diagram schematically showing a chin device (side).
Figure 22:
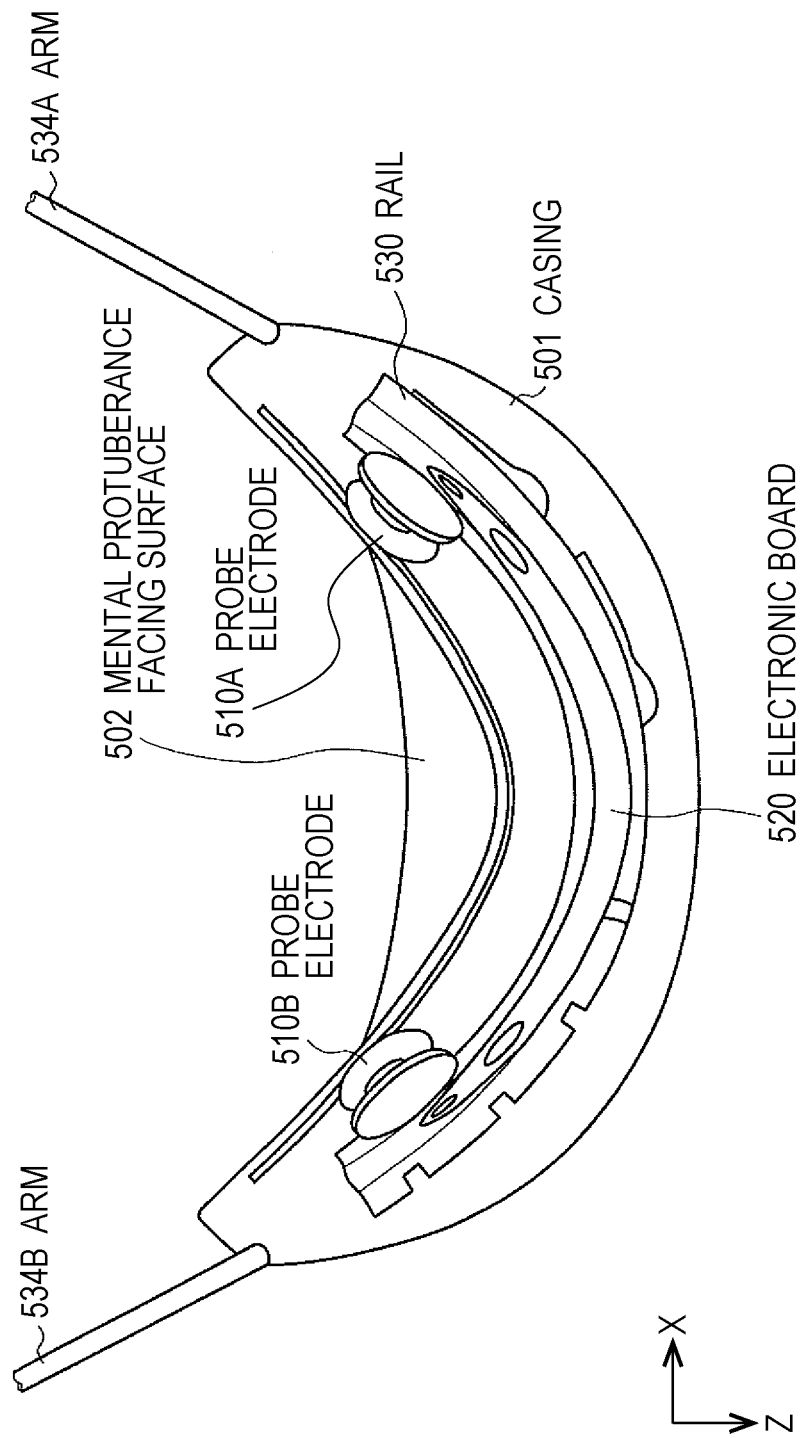
FIG. 22 is a diagram schematically showing a chin device (top).

It should be noted that the portion extending to the rear end from a position separated from the recess 312 by a predetermined interval toward the rear end is formed narrower than the portion extending from this position to the front end (see FIG. 18). The stepped portion at this position serves as a stopper for the adjuster section 330. Therefore, the number of parts is reduced as compared with the case of separately providing a stopper, which enables a corresponding reduction in size.

A section (hereinafter, this will be also referred to as occiput abutment section) abutted against the occiput is attached at the rear end of the hair band 310 (open end of the adjuster section 330) (see FIG. 9 to FIG. 11, and FIG. 13 to FIG. 16). The occiput abutment section 340 has an acuminate fin shape or spade shape that is narrow at the coupling portion, becomes gradually wider, and then becomes narrower toward the distal end from a midway position. The occiput abutment section 340 has a wider area than the section to be abutted against the forehead (forehead abutment section 350 described later) which is attached at the front end of the hair band 310. Therefore, stability with respect to the head is enhanced.

A core region 340A at the center of the occiput abutment section 340 and in its vicinity is made of a hard material, and a peripheral region 340B other than the core region 340A is made of a soft material such as silicone or urethane (see FIG. 18). Therefore, adherence to the head is enhanced, and also biting into the head is prevented.

A hair clip (not shown) or sucking disc (not shown) is detachably attached to the inner side of the core region 340A via bored holes 341A and 341B. Therefore, stability with respect to the head is further enhanced irrespective of the presence of hair.

It should be noted that the core region 340A is depressed in comparison to the peripheral region 340B to an extent approximately equivalent to the height of the hair clip or sucking disc. Therefore, a situation where the occiput abutment section 340 lifts up from the head due to the attachment of the hair clip or sucking disc is prevented from occurring.

In the connecting portion between the core region 340A and the adjuster section 330, there is provided an angle adjustment mechanism 342 that makes the angle of the inner surface of the occiput abutment section 340 variable with respect to the inner surface of the hair band 310. Therefore, the angle of the inner surface of the occiput abutment section 340 with respect to the contacting portion with the head can be adjusted. As a result, stability with respect to the head is further enhanced.

The section (hereinafter, this will be also referred to as forehead abutment section) 350 to be abutted against the forehead is attached at the front end of the hair band 310 (see FIG. 9 to FIG. 16). The forehead abutment section 350 has a teardrop shape, and is made of a soft material such as silicone or urethane. Therefore, adherence to the forehead is enhanced, and also biting into the forehead is prevented.

In the inner surface of the forehead abutment section 350, there is formed a recessed groove 351 that divides the inner surface into an upper region and a lower region (see FIG. 9 to FIG. 11, FIG. 15, and FIG. 16). The flexibility of the forehead abutment section 350 is improved by the recessed groove 351. As a result, adherence of the forehead abutment section 350 to the forehead is further enhanced.

The outer surface of the hair band 310 is provided with a casing (hereinafter, this will be also referred to as protruding casing) 360 in the form of a protrusion that accommodates electronic equipment (see FIG. 9 to FIG. 16). The protruding casing 360 includes a fixed region 361 and a protruding region 362 (see FIG. 9 to FIG. 12, FIG. 14, and FIG. 16). The fixed region 361 is fixed to the outer surface of the hair band 310 situated directly above the forehead abutment section 350. Pairs of arm attachment ports 101 and 102, and 103 and 104 are respectively provided in the upper section and lower section of the side surface of the fixed region 361 (see FIG. 16).

The protruding region 362 is separated from the hair band 310, and protruded upward at a predetermined distance away from the outer surface at the top of the hair band 310. Therefore, the board is spaced apart by taking ease of attachment to the head into consideration. That is, the hair band 310 can be smoothly attached without hindering changes in the curved state of the hair band 310 at the time of attachment.

The protruding region 362 has a flat profile that is more gently curved than the hair band 310. Therefore, as compared with cases where electronic equipment is accommodated inside the hair band 310, the range of circuit board choices can be extended, and also influence due to bending of the hair band 310 is avoided.

The upper surface of the protruding region 362 is provided with a long-press button 363 that turns power on or off when pressed for several seconds (see FIG. 9, FIG. 10, FIG. 12, and FIG. 16). Therefore, accidental power on or off upon hitting a nearby object when going to sleep or standing up is prevented.

The side surface of the protruding region 362 is provided with a plurality of kinds of connectors 364 (see FIG. 9 to FIG. 12, FIG. 14, and FIG. 16) for removable media such as an SD (Secure Digital) card and a USB (Universal Serial Bus) memory, for example.

Arms 380A and 380B that support a pair of reference electrodes 370A and 370B are detachably attached to the arm attachment ports 101 and 102 in the upper part (see FIG. 9 to FIG. 11). The length of the arms 380A and 380B is such that the arms 380A and 380B each reach the earlobe via the back of the ear by extending along the surface of the head. Sections (hereinafter, these will be also referred to as earlobe attachment sections) 390A and 390B for attaching the reference electrodes 370A and 370B to the earlobes are provided at the distal ends of the arms 380A and 380B (see FIG. 9 to FIG. 11).

Arms 380C and 380D that support a pair of probe electrodes 400A and 400B are detachably attached to the arm attachment ports 103 and 104 in the lower part (see FIG. 9 to FIG. 11). The length of the arms 380C and 380D is such that the arms 380C and 380D each reach the depression (hereinafter, this will be also referred to as temple) surrounded by the frontal bone, the zygomatic arch, and the zygomatic orbital process. Sections (hereinafter, these will be also referred to as temple attachment section) 410A and 410B for attaching the probe electrodes 400A and 400B to the temples are provided at the distal ends of the arms 380C and 380D (see FIG. 9 to FIG. 11).

Each arm 380 is made of a soft material such as PBT or PP, and is formed in a cylindrical shape. A rigid linear member (not shown) such as a piano string or a wire is placed inside each arm 380. Therefore, the shape of the arm 380 can be flexibly adjusted, and also the adjusted state can be retained.

The earlobe attachment sections 390A and 390B (FIG. 9 to FIG. 11) have frames 391A and 391B that are coupled to the distal ends of the arms 380A and 380B. Jack-type connectors 392A and 392B are provided at the lower ends of the frames 391A and 391B.

The frames 391A and 391B are structured so that the reference electrodes 370A and 370B bearing magnetism are exposed over the entire planar regions of the frames 391A and 391B or their center regions excluding peripheral edges. Also, disc-shaped magnets 394A and 394B are attached to the frames 391A and 391B via plate-like coupling members 393A and 393B having flexibility.

Therefore, the earlobe attachment sections 390A and 390B are configured such that the coupling members 393A and 393B can be folded over to clamp the earlobes between the earlobe attachment sections 390A and 390B and the reference electrodes 370A and 370B, and fixe the reference electrodes 370A and 370B to the earlobes by magnetic force.

The temple attachment sections 410A and 410B (FIG. 9) have frames 411A and 411B that are coupled to the distal ends of the arms 380C and 380D, with the probe electrodes 400A and 400B being exposed over the entire planar regions of the frames 411A and 411B or their center regions excluding peripheral edges. A sheet having adhesiveness to the skin like a solid gel or the like is attached to the peripheral edge of each of the frames 411A and 411B. Therefore, stability and adherence of the probe electrodes 400A and 400B with respect to the temples are secured.

It should be noted that the frames 391A, 391B, 411A and 411B are each assigned a different shape so as to allow visual recognition of "upper right", "upper left", "lower right", and "lower left".

A lead (not shown) is connected to each reference electrode 370 and each probe electrode 400. The lead is extended to the interior of the fixed region 361 of the protruding casing 360, along a linear member (not shown) placed in the inner hollow of the corresponding arm 380. Also, a lead (not shown) is connected to each probe electrode 320 attached to the hair band 310 as well. The lead is extended to the interior of the fixed region 361 of the protruding casing 360 via the inside of the hair band 310.

In the interior of the fixed region 361, amplifiers (not shown) assigned to the respective electrodes 320, 370, and 400 are connected, and the ground lines of these amplifiers are each connected to a single ground point. This is an earthing technique called star earthing.

The fixed region 361 is arranged at such a position that each of the electrodes 320, 370, and 400 is at the shortest distance to this position. Thus, interference noise superimposed on the leads to the electrodes 320, 370, and 400 is significantly reduced. Also, since the ground lines of the amplifiers assigned to the respective electrodes 320, 370, and 400 are gathered at a single point inside the fixed region 361, loop due to the ground point is reduced.

It should be noted that in the fixed region 361, other than the amplifiers, analog electron devices that are highly susceptible to the influence of noise are preferentially provided. In contrast, in the protruding region 362, digital electron devices that are not very susceptible to the influence of noise are preferentially provided.

The chin device 500 has a casing 501 formed by combination of a material having flexibility and a material having rigidity. A surface (hereinafter, this will be also referred to as mental protuberance facing surface) 502 corresponding to the shape of the mental protuberance of the lower jaw is formed in the casing 501. A sheet having adhesiveness such as a solid gel is attached to the mental protuberance facing surface 502.

Therefore, the shape of the mental protuberance facing surface 502 ensures an easy fit by groping for the mental protuberance even without looking at a mirror or the like, and the fitting state can be stabilized.

Probe electrodes 510A and 510B, an electronic board 520, and a rail 530 are installed in the interior of the casing 501.

The probe electrodes 510A and 510B are disk-shaped, and each positioned on the perpendicular to the mental tubercle, for example.

The electronic board 520 is formed as a flexible board, and is placed between one probe electrode 510A and the other probe electrode 510B while being curved along the mental protuberance facing surface 502. An amplifier (not shown) for amplifying a biosignal sensed by each of the probe electrodes 510A and 510B is placed on the electronic board 520.

The rail 530 is made of a material having high slidability such as POM, and is placed horizontally while being curved along the mental protuberance facing surface 502. An upper guide groove 531A and a lower guide groove 531B are formed in the rail 530.

A post-like stopper 532A is fixed at one end of the upper guide groove 531A. One end of a spring 533A that expands and contracts along the track of the upper guide groove 531A is fixed to the stopper 532A. One end of an arm 534A inserted through the upper guide groove 531A is fixed to the other end of the spring 533A. At the other end of the arm 534A, a pin-type connector (not shown) corresponding to the connector 392A of the earlobe attachment section 390A is provided, which is attached to and detached from the connector 392A.

A post-like stopper 532B is fixed at one end of the lower guide groove 531B. This one end is located on the side opposite to the one end at which the stopper 532A is provided in the upper guide groove 531A.

As in the case of the upper guide groove 531A, one end of a spring (not shown) is fixed to the stopper 532B, and one end of an arm 534B is fixed to the other end of the spring (not shown). At the other end of the arm, a pin-type connector (not shown) corresponding to the connector 392B of the earlobe attachment section 390B is provided, which is attached to and detached from the connector 392B.

Therefore, the springs 533A makes it possible to adjust the arms 534A and 534B to a length corresponding to the distance between the chin device 500 and the earlobe attachment sections 390A and 390B, and also prevent displacement of the chin device 500 by applying pressing forces that act against each other.

It should be noted that the arms 534A and 534B are made of a soft material such as silicone, PBT, or PP, and formed in a cylindrical shape. A rigid linear member (not shown) such as a piano string or a wire is placed inside each of the arms 534A and 534B. Therefore, the arms 534A and 534B can be placed along the surface of the face above the corner portion of the lower jaw, and the adjusted state can be retained.

Also, the fixing positions of the stoppers 532A and 532B can be adjusted by changing the recesses to fit the stoppers 532A and 532B in, among a plurality of fitting recesses 535 (see FIG. 20) formed at predetermined intervals in the direction of the track of the upper and lower guide grooves 531A and 531B.

[3-2. Attachment Procedure]

Next, an attachment procedure for the biosignal measurement device will be described. In a first step, the hair band 310 is put over the head from front to back.

Since the front end of the hair band 310 is formed at a position higher than the rear end (see FIG. 10 and FIG. 11), the subject can intuitively grasp which directions are front and back of the head device 300. Also, the hair band 310 is made of a plate material having bendability and rigidity such as plastic or metal, and its width is set to a value smaller than the distance between a straight line connecting "F3" and "P3" in the international 10-20 system, and a straight line connecting "F4" and "P4".

Thus, the hair band 310 can flexibly fit the contour portion, passing the median plane while leaving the lateral portion of the head open, thereby significantly mitigating migraine or discomfort caused when the subject lies down.

Also, since the hair band 310 is so structured as to clamp the head from front to back via the contour portion passing the median plane, the self weight of the hair band 310 acts to compress the contour portion passing the median plane.

Figure 23:
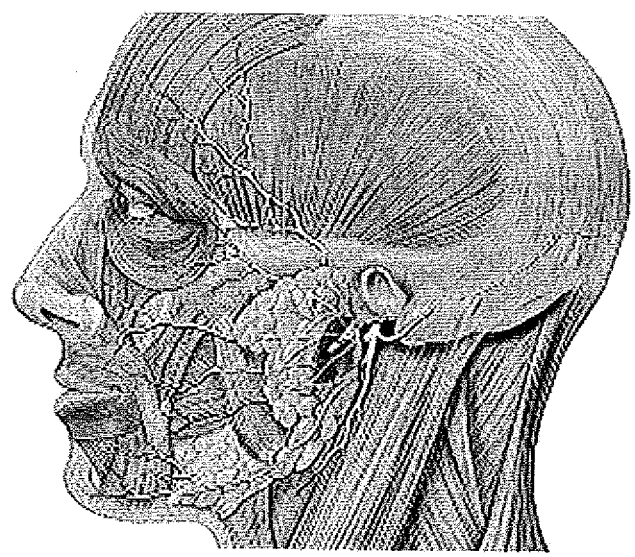
FIG. 23 is a diagram showing the nervous system running from the face surface to the head.
Figure 24:
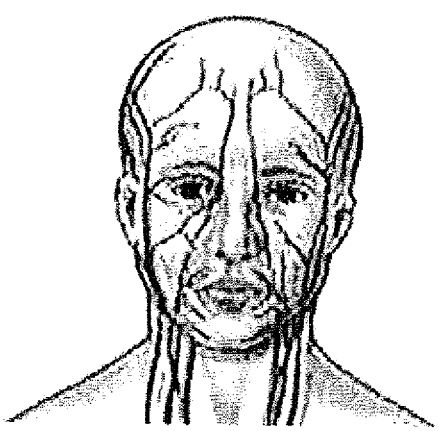
FIG. 24 is a diagram showing the vascular system running from the face surface to the head.
Figure 25:
FIG. 25 is a diagram showing the lymphatic system running from the face surface to the head.
Figure 26:
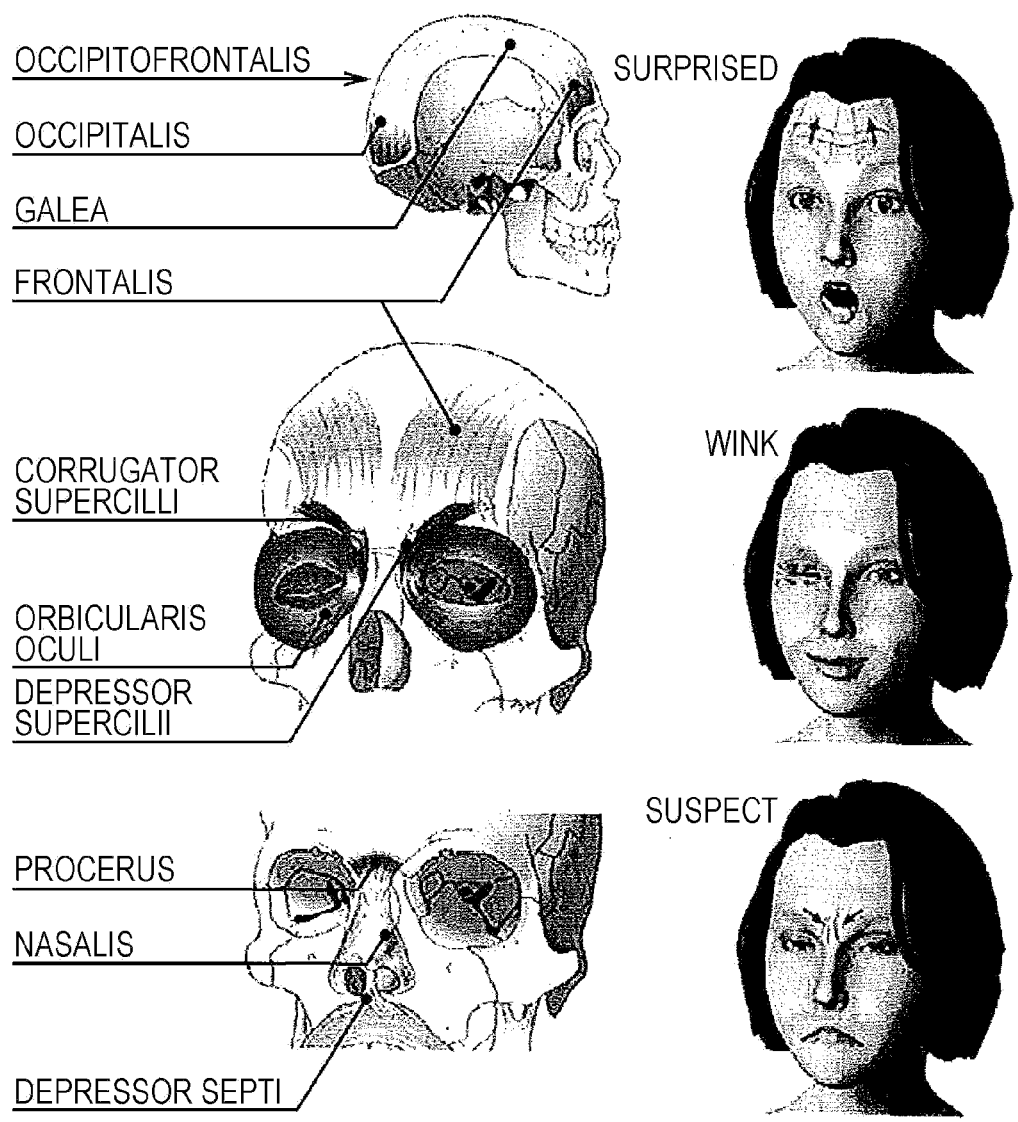
FIG. 26 is a diagram showing the relationship between muscles running from the face surface to the head and facial expressions.
Figure 27:
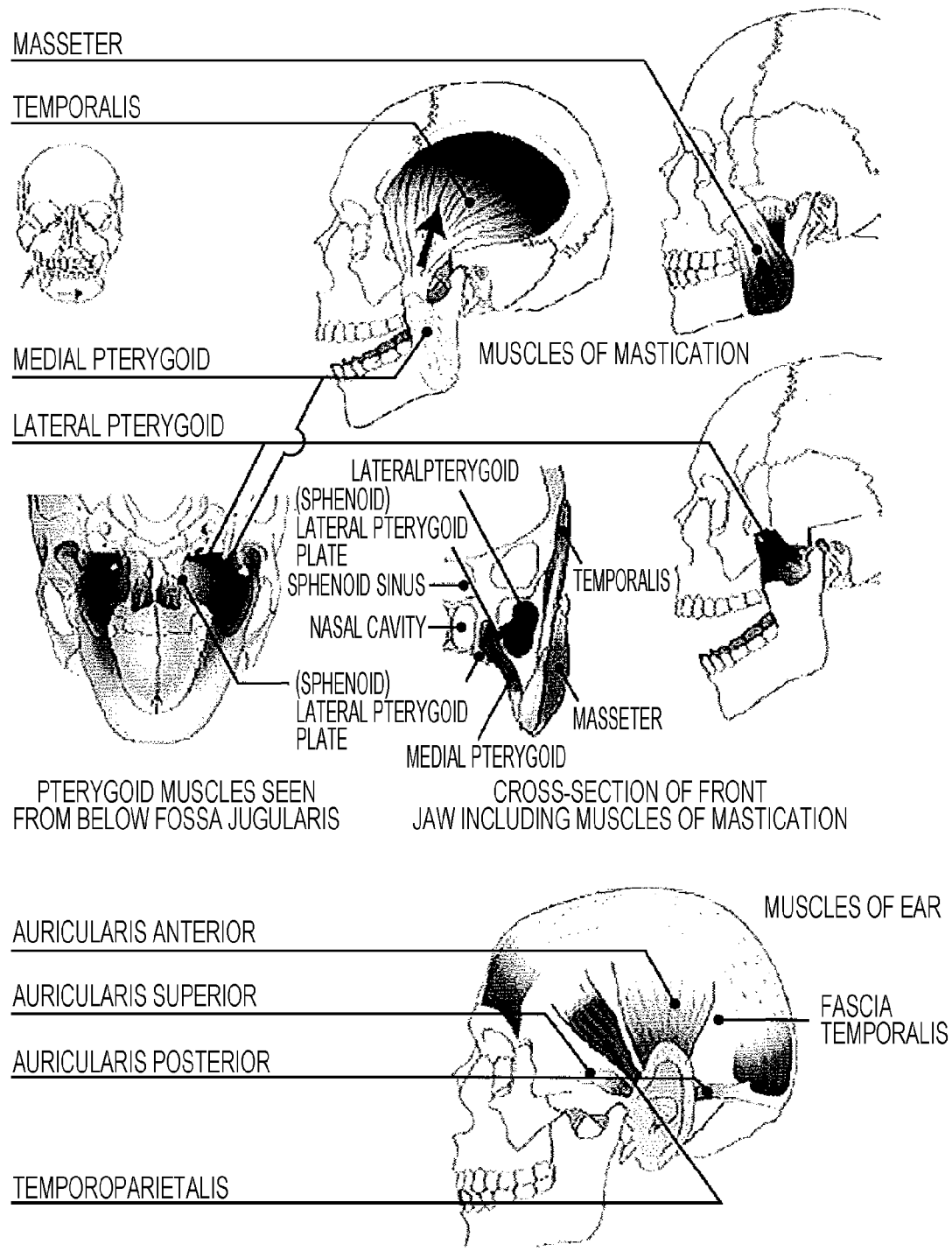
FIG. 27 is a diagram showing the muscles of mastication, and eye/ear muscles.

However, as shown in FIG. 23 to FIG. 25, the nerves, blood vessels, lymphatics running from the face to the head do not lie in the portion that contacts the inner surface of the hair band 310 (the contour portion passing the median plane). Also, as shown in FIG. 26 and FIG. 27, the muscles running from the face surface to the head do not lie in the portion that contacts the inner surface of the hair band 310 (the contour portion passing the median plane), either.

Therefore, as compared with the case of the structure that clamps the head without going through the contour portion passing the median plane as in the first embodiment, for example, the amount of, compression applied by the hair band 310 to the nervous system, the vascular system, the lymphatic system, and the muscular system can be minimized. As a result, migraine or discomfort caused by attachment can be significantly reduced.

It should be noted that FIG. 23 is illustrated [online], "Facial nerve", Wikipedia, the free encyclopedia, [searched on May 27, 2010]. On the other hand, FIG. 24 and FIG. 25 are illustrated in F. H. Martini, "*Human Anatomy*", Nishimura Co., Ltd., 2003, page 8. On the other hand, FIG. 26 and FIG. 27 are illustrated in Yoshinori Kawai, ed., "*Nikutan*", NTS Inc., Jun. 8, 2007, 26th ed., pages 7-8.

On the other hand, from the inner surface of the hair band 310, the distal ends of the probe electrodes 320A and 320B (conductive fibers 321) project to an extent that does not impair fitting of the hair band 310 to the head, thereby improving adherence of the conductive fibers 321 to the head.

Generally speaking, since the scalp secretes more sebum and has faster metabolism than does the skin with a relatively small amount of hair such as the face surface, a horny layer tends to easily form. Therefore, it is necessary to clean the scalp prior to electrode attachment in conventional electroencephalography.

However, since the structure of the probe electrodes 320A and 320B is such that the plurality of conductive fibers 321 are implanted upright on the substrate 322, all or some of the conductive fibers 321 penetrate the sebum and horny layer into contact with the scalp while avoiding head hair. Therefore, electroencephalography can be performed even when cleaning of the scalp at the electrode location is omitted. As a result, burden on the subject is reduced without substantially compromising measurement accuracy, thus enabling electroencephalography to be performed for a long duration of time.

Also, when attaching electrodes in conventional electroencephalography, it is necessary to apply a paste to keep the electrode in contact with the scalp.

However, in the probe electrodes 320A and 320B, the conductive fibers 321 are each fixed to the substrate 322 at a single point. Thus, the conductive fibers 321 can each move around isotropically about the fixed point as the center.

For this reason, the conductive fibers 321 are kept in contact with the scalp irrespective of the shape of the head, even when application of a paste is omitted. Further, no matter from which direction a force is applied due to tossing and turning in bed or the like, the conductive fibers 321 adapt to the applied force while keeping their contact, and once the force disappears, the conductive fibers 321 return to the original state while keeping their contact.

Figure 28:
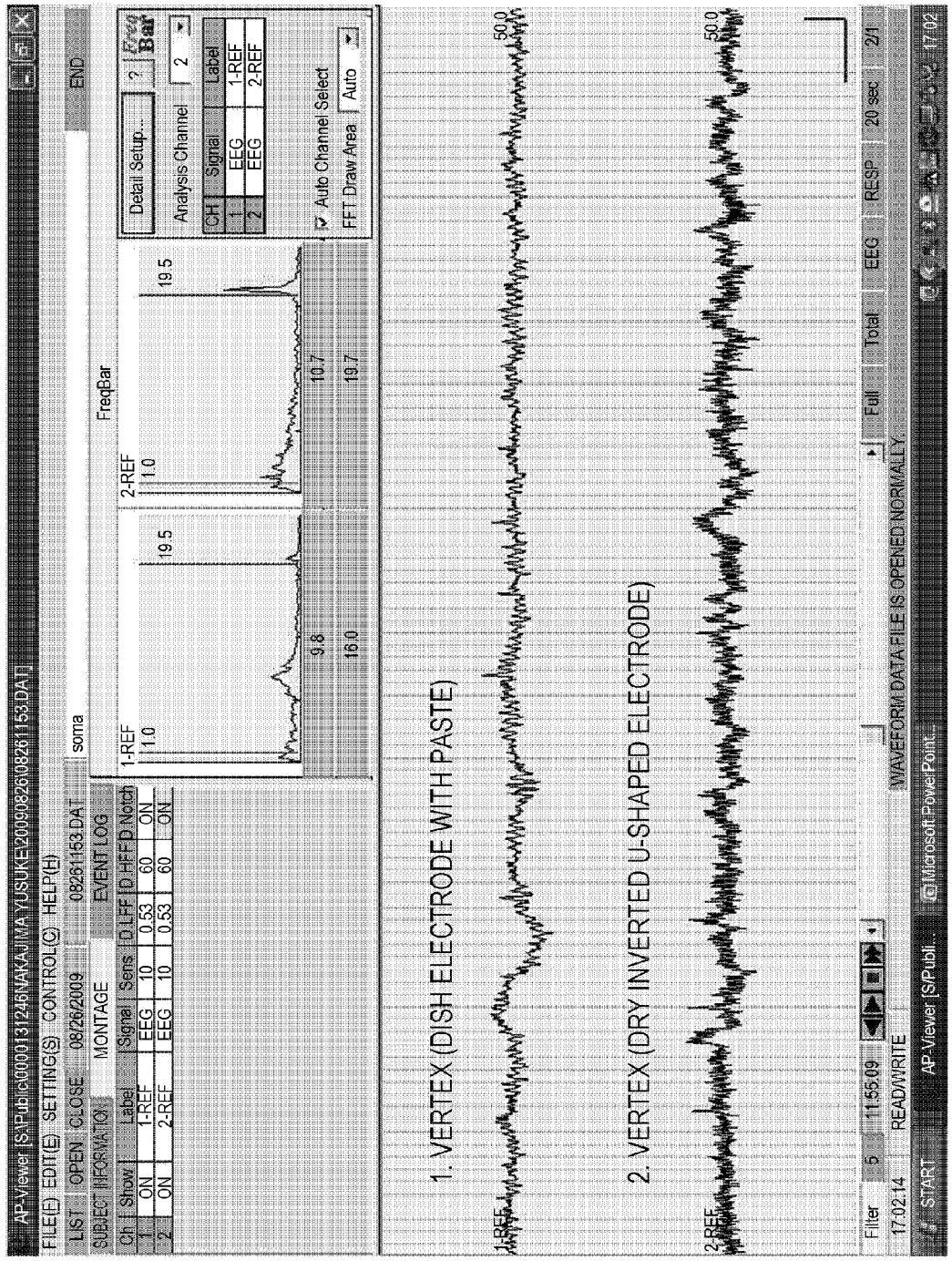
FIG. 28 is a graph showing experimental results.
Figure 29:
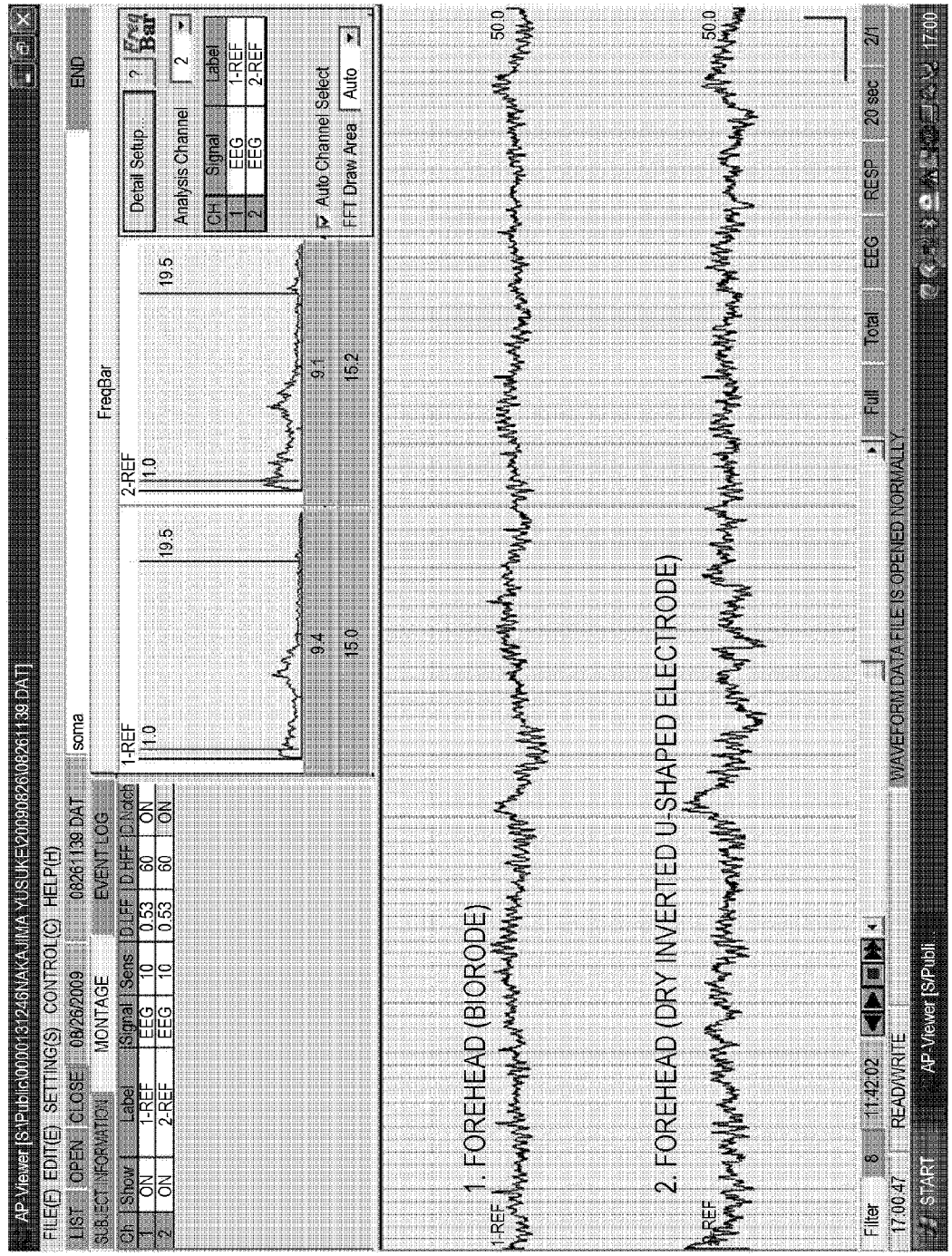
FIG. 29 is a graph showing experimental results.
Figure 30:
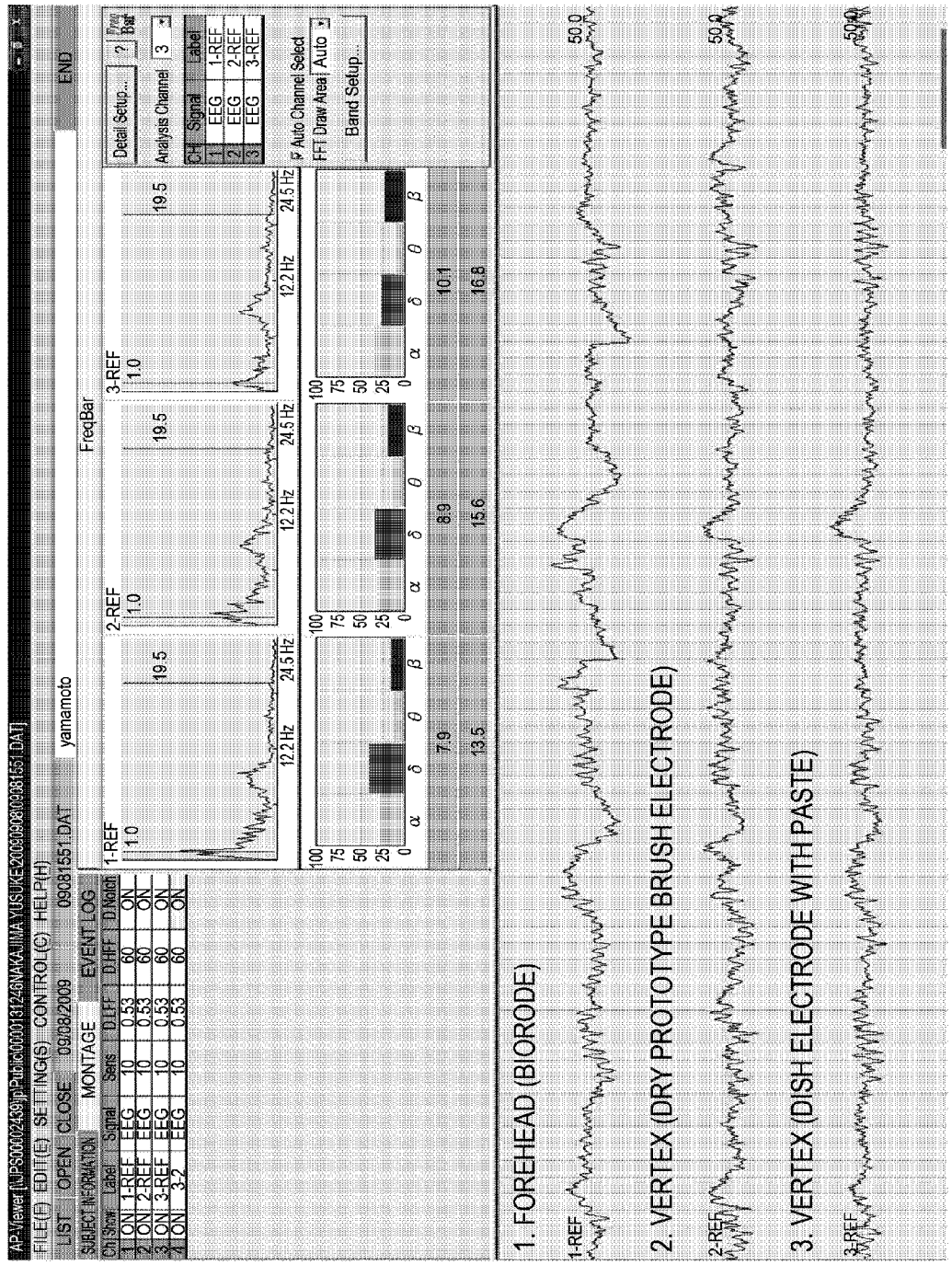
FIG. 30 is a graph showing experimental results.

Here, experimental results are shown in FIG. 28 to FIG. 30. FIG. 28 shows biosignal sensing results in the case when a dish-shaped electrode is placed with a paste, and when an inverted U-shaped electrode is placed without a paste, on the vertex (central median).

FIG. 29 shows biosignal sensing results in the case when a Biorode is placed, and when an inverted U-shaped electrode is placed without a paste, on the forehead. FIG. 30 shows biosignal sensing results in the case when a Biorode is placed, when an electrode of a brush structure (prototype of the probe electrode 320) is placed without a paste, and when an inverted U-shaped electrode is placed without a paste, on the vertex (central median).

As can be appreciated from these experimental results, for the electrode of a brush structure (prototype of the probe electrode 320) provides the same results as the related art which performs sensing using a conventional dish electrode applied with a paste, even through application of a paste is omitted.

In a second step, the position of the occiput abutment section 340 with respect to the head is finely adjusted. That is, the length of the hair band 310 is adjusted with the adjuster section 330 so that the occiput abutment section 340 is located directly above the midline occipital (Oz in the international 10-20 system). Since the occiput abutment section 340 is placed so as to avoid contact with the projecting part of the head, pain caused to the subject can be mitigated, thereby making it possible to significantly reduce sleep impairment for the subject as a result.

Also, the angle of the occiput abutment section 340 is adjusted by the angle adjustment mechanism 342 (FIG. 18) so that the inner surface of the occiput abutment section 340 becomes substantially parallel to the contact surface with the head. Therefore, stability with respect to the head is enhanced.

In a third step, a hair clip (not shown) or sucking disc (not shown) detachably attached to the occiput abutment section 340 is attached to the hair or scalp. Therefore, stability with respect to the head is further enhanced irrespective of the presence of hair.

In a fourth step, the shapes of the arms 380A and 380B are changed as appropriate so that their distal ends are positioned at the earlobes via the back of the ears along the surface of the head, and the shapes of the arms 380C and 380D are changed as appropriate so that their distal ends are positioned at the temples along the surface of the face.

Since each arm 380 is formed in a cylindrical shape from a soft material, and a rigid linear member (not shown) is placed in the inside, the shape of the arm 380 can be flexibly adjusted for the subject, and also the adjusted state can be retained.

In a fifth step, the earlobe attachment sections 390A and 390B provided at the distal ends of the arms 380A and 380B are attached to the earlobes, and the temple attachment sections 410A and 410B provided at the distal ends of the arms 380C and 380D are attached to the temples.

Since the earlobe attachment sections 390A and 390B are so structured as to clamp the earlobes between the magnets 394A and 394B, and the reference electrodes 370A and 370B, stability and adherence of the reference electrodes 370A and 370B with respect to the earlobes can be ensured. Also, it is possible to quickly fix the reference electrodes 370A and 370B to the subject.

Since a sheet having adhesiveness to the skin is attached to each of the peripheral edges of the frames 411A and 411B of the temple attachment sections 410A and 410B, stability and adherence of the probe electrodes 400A and 400B with respect to the earlobes can be ensured. Also, it is possible to quickly fix the probe electrodes 400A and 400B to the subject.

In a sixth step, the casing 501 is put over the chin. The surface (mental protuberance facing surface) 502 corresponding to the shape of the mental protuberance of the lower jaw is formed in the casing 501. Thus, the shape of the mental protuberance facing surface 502 allows for a quick fit to the mental protuberance by groping for the mental protuberance without having the subject look at a mirror or the like, and the fitting state can be stabilized.

In a seventh step, the arms 534A and 534B are extended, and the shapes of the arms 534A and 534B are changed as appropriate so as to conform to the face surface above the corner portion of the lower jaw. Since the arms 534A and 534B are each formed in a cylindrical shape from a soft material, and a rigid linear member (not shown) is placed in the inside, the shape of each arm 534 can be flexibly adjusted for the subject, and also the adjusted state can be retained.

In an eighth step, the pin-type connectors at the distal ends of the arms 534A and 534B are inserted into the jack-type connectors of the earlobe attachment sections 390A and 390B. The arm 534 is coupled via the spring 533 to the stopper 532 fixed on the side that is opposite to the arm 534 from left to right in the guide groove 531 of the rail 530.

Therefore, by the spring 533, the arm 534 is adjusted to a length corresponding to the distance between the chin device 500 and the earlobe attachment section 390, and also the pressing forces acting against each other which are exerted by the spring 533 prevent displacement of the chin device 500 to ensure stability.

Figure 31:
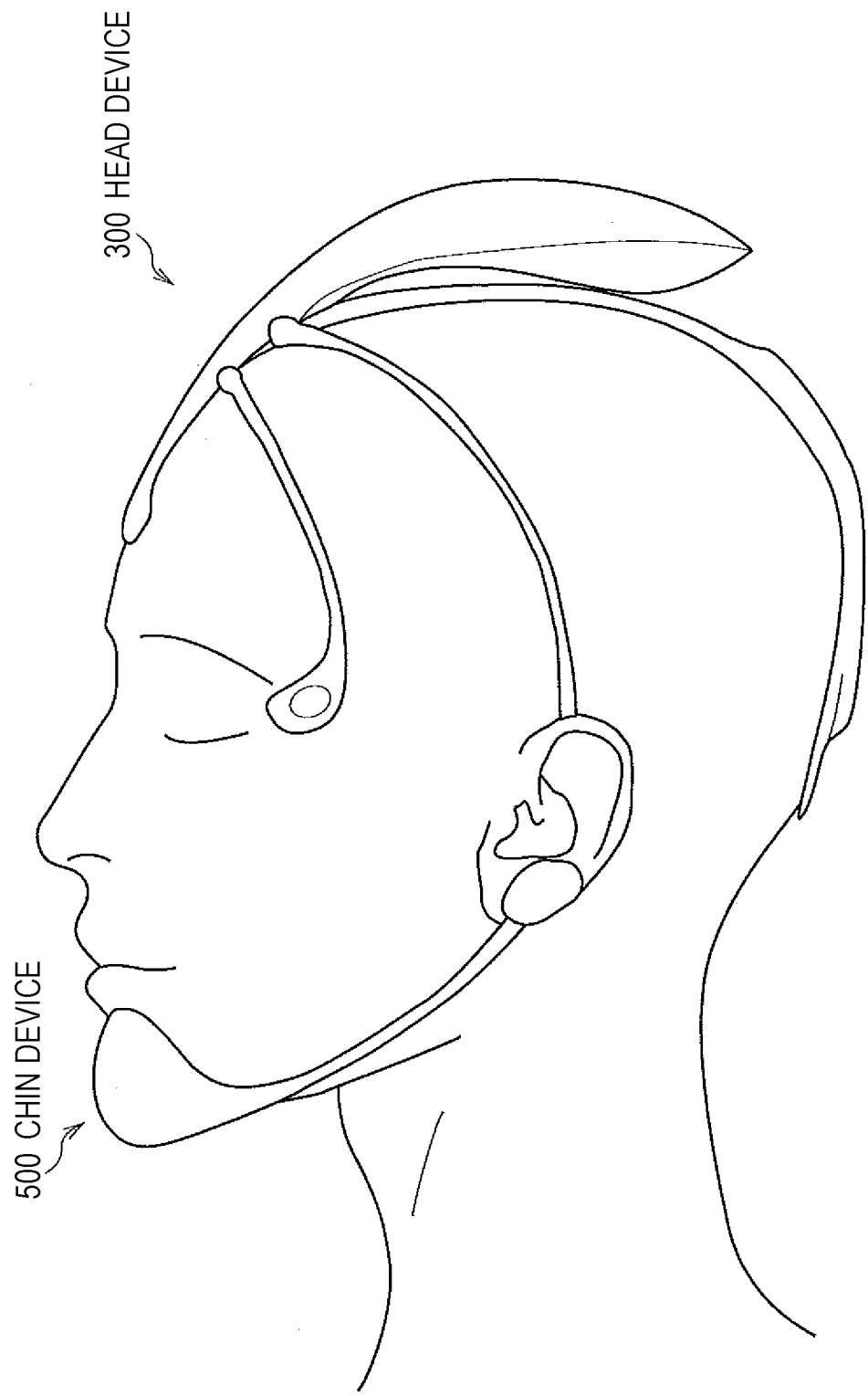
FIG. 31 is a diagram schematically showing the attached state of a biosignal measurement device.

Through the above attachment procedure, as shown in FIG. 31, for example, the head device 300 and the chin device 500 are attached to the head and the chin. As a result, the probe electrodes 320A and 320B, the probe electrodes 400A and 400B, the reference electrodes 370A and 370B, and the probe electrodes 510A and 510B are fixed to the scalp, the temples, the earlobes, and the mental protuberance, respectively. It should be noted, however, that the attachment sequence described above is only an example, and this attachment sequence is not limitative.

[3-3. Configuration of Measurement Section]

Figure 32:
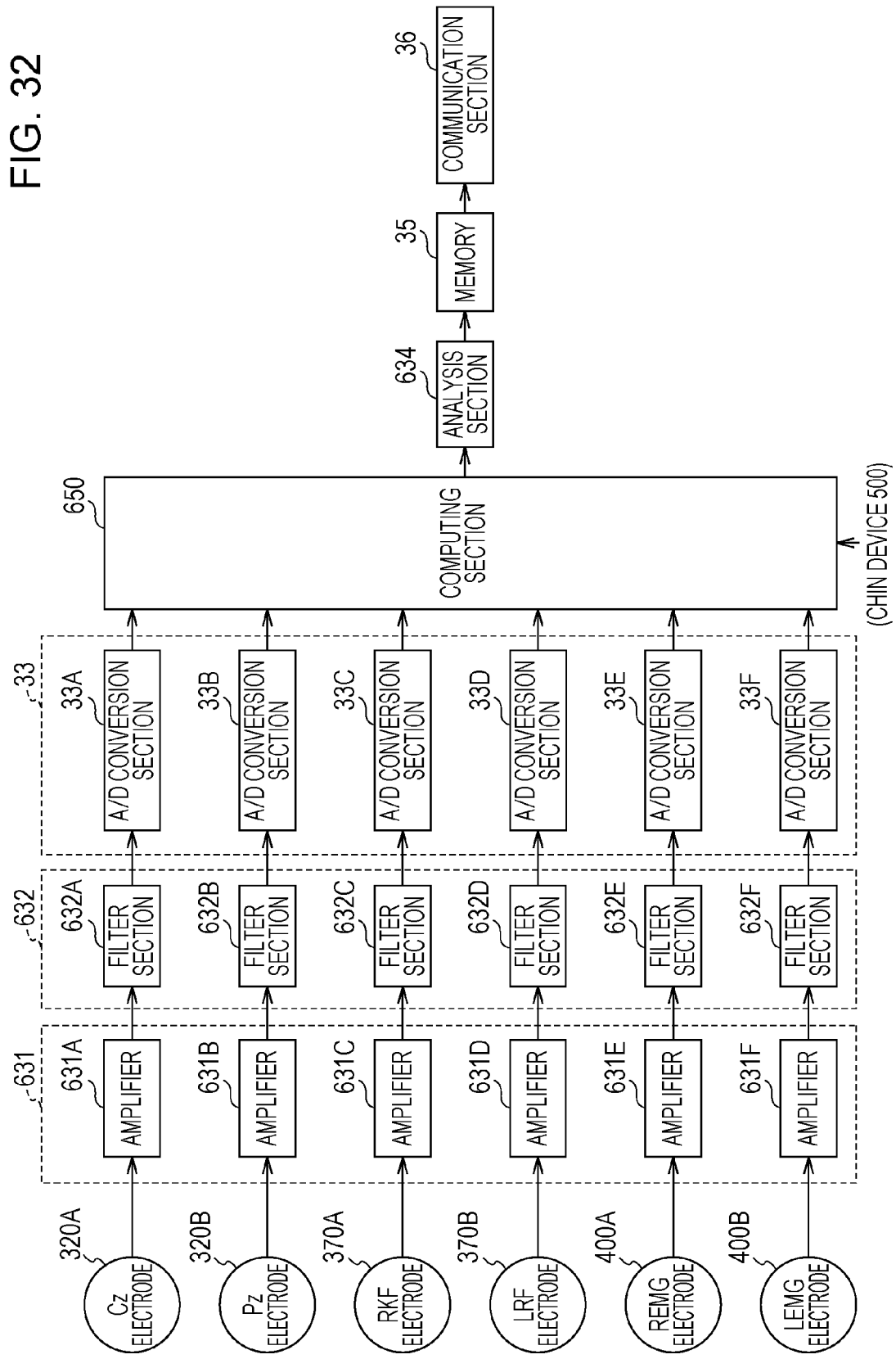
FIG. 32 is a diagram schematically showing the circuit configuration of a measurement section.

The configuration of a measurement section 600 is shown in FIG. 32 in which portions corresponding to those in FIG. 4 are denoted by the same symbols. The measurement section 600 includes an amplification section 631, an A/D conversion section 33, a filter section 632, a computing section 650, an analysis section 634, a memory 35, and a communication section 36.

The amplification section 631 has amplifiers 631A to 631F assigned to the respective electrodes 320, 370, and 400, and amplifies the difference between each of the electrodes 320, 370, and 400, and a reference potential (ground point).

The filter section 632 does not differ from the filter section 32 that is an analog filter, except in that the filter section 632 is a digital filter. The filter section 632 has filter sections 632A to 632F assigned to the respective electrodes 320, 370, and 400, and after signal components other than set frequency bands are removed, conversion results are obtained in the corresponding A/D conversion sections 33A to 33F.

Specifically, a band-pass filter that selects a frequency band of brain waves, a notch filter that removes AC noise, or a combination of those or the like is preferred.

Incidentally, in polysomnography, the measurement apparatus is placed in a room different from where the instrument attached to the subject is present. Therefore, in conventional polysomnography, it is essential to provide a shielded room to avoid the influence of interference noise or the like superimposed on the connecting line between the instrument and the measurement apparatus.

However, the position where the fixed region 361 is placed in the protruding casing 360 is a position such that each of the electrodes 320, 370, and 400 is at the shortest distance to this position, and the ground lines of the amplifiers assigned to the respective electrodes 320, 370, and 400 are gathered at a single point inside the fixed region 361. Thus, even without a shielded room, the influence of noise is significantly reduced, thereby allowing electroencephalography to be performed in ordinary households as well.

Incidentally, if electroencephalography can be performed in ordinary households, various kinds of interference noise are present. Noise caused by a socket is a representative example. For example, the frequency band of noise caused by a socket differs from region to region such as Tokyo and the Kansai region, which means that the frequency band to be removed by the filter section 632 differs.

However, with the analog filter shown in FIG. 4, it is difficult to switch frequency bands to be removed by a single filter, so a number of filters equal to the number of frequency bands to be removed are required. In contrast, since the filter section 632 in the measurement section 600 is a digital filter, the computing section 650 can be included, and by using a single DSP capable of pipeline processing, switching of frequency bands to be removed or the like can be executed by programming.

Therefore, even if it becomes possible to perform electroencephalography in ordinary households, the filter section 632 can accurately remove frequency bands regarded as interference noise with a minimum number of filter sections. As a result, measurement accuracy can be improved.

Figure 33:
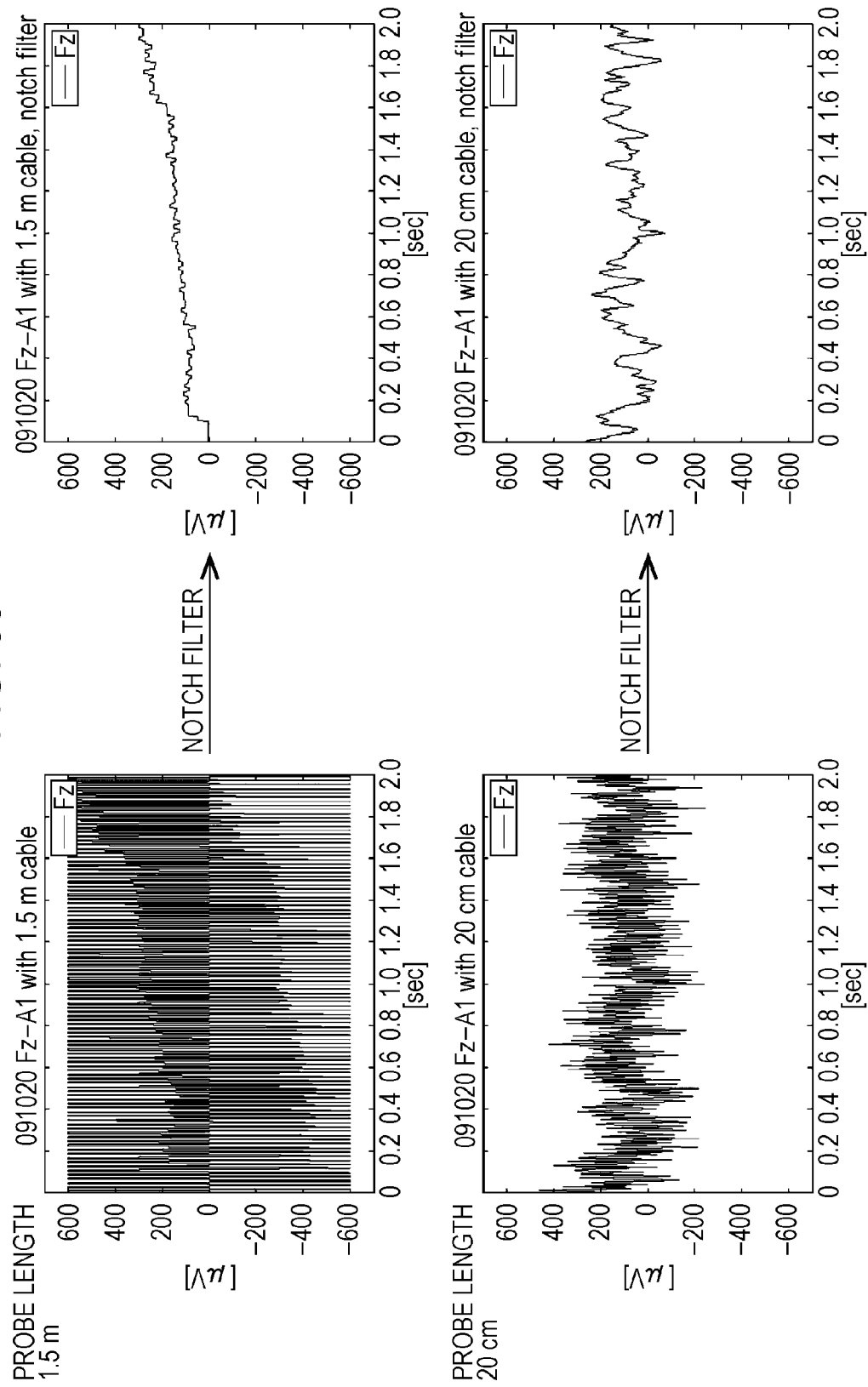
FIG. 33 is a graph showing experimental results.

Here, experimental results are shown in FIG. 33. The upper panel of FIG. 33 shows measurements performed in a location other than a shielded room by using a cord with a cable length (1.5 [m]) equivalent to the cable length in conventional electroencephalography. In this case, the biosignal is saturated due to AC noise, and the biosignal is buried in noise even when a notch filter is applied.

On the other hand, the lower panel of FIG. 33 shows measurements performed in a location other than a shielded room by using a cord with a cable length (0.2 [m]) equivalent to the cable length in the chin device 300. In this case, AC noise has substantially the same amplitude as the biosignal, so the biosignal appears after a notch filter is applied.

It should be noted that since the probe electrodes 510A and 510B in the chin device 500 are at a longer distance from the fixed region 361 than the other electrodes 320, 370, and 400, the probe electrodes 510A and 510B are each connected to an amplifier located inside the chin device 500 separately from the fixed region 361. Therefore, there is substantially no influence of noise on the biosignal sensed by each of the probe electrodes 510A and 510B.

The computing section 650 takes the difference between the output of the filter section 632A or 632B assigned to the probe electrode 320, and the output of the filter section 632C or 632D assigned to the reference electrode 370, and outputs the result to the subsequent stage.

Also, the computing section 650 takes the difference between the output of the filter section 632E or 632F assigned to the probe electrode 400, and the output of the filter section 632C or 632D assigned to the reference electrode 370, and outputs the result to the subsequent stage.

It should be noted that the result obtained by amplifying and then filtering the difference between the probe electrode 510A or 510B and a reference potential (ground point) in the electronic board 520 placed inside the casing 501 of the chin device 500 is sequentially inputted to the computing section 650 via the arm 534A or 534B and the connector 392A or 392B.

The computing section 650 takes the difference between an input from the connector 392A or 392B corresponding to the probe electrode 510A or 510B, and the output of the filter section 632C or 632D assigned to the reference electrode 370, and outputs the result to the subsequent stage.

In this way, the computing section 650 is configured to take the difference between an output corresponding to the probe electrode 320, 400, or 510, and an output corresponding to the reference electrode 370. This is because the amplification section 631 amplifies not the potential difference between the reference electrode and the probe electrode but the difference between each of the electrodes 320, 370, and 400, and a reference point that should be common.

The analysis section 634 determines the start time, end time, and quality of REM sleep by using the myoelectric potential of the jaw sensed by the probe electrodes 510A and 510B, in addition to the myoelectric potential of the eyes sensed by the probe electrodes 400A and 400B.

Generally, it is known that the muscular force of the jaw weakens during REM sleep in comparison to periods other than the REM sleep. Therefore, as compared with the analysis section 34 that determines the start time, end time, and quality of REM sleep solely by the myoelectric potential of the eyes sensed by the probe electrodes 400A and 400B, the accuracy of the determination is further improved.

<4. Other Embodiments>

In the first embodiment mentioned above, the hair band 2 is attached so as to clamp the left and right side sections of the head. However, the attachment method is not limited to this. For example, it is also attach the hair band 2 so as to clamp the front and back side sections of the head.

In the first embodiment mentioned above, the hair band 2, the reference electrode 12, and the probe electrode 13 are employed as the components of the biosignal measurement device 1. However, the components of the biosignal measurement device 1 are not limited to the shapes, structures, and the like illustrated in the above-described embodiment.

Figure 34:
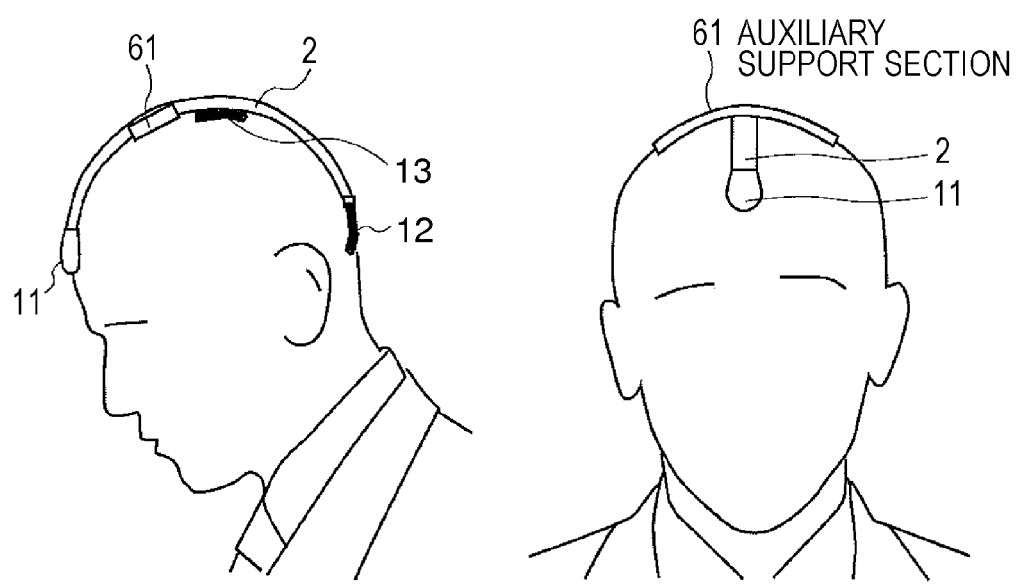
FIG. 34 is a diagram schematically showing the attached state of a biosignal measurement device according to another embodiment.

For example, as shown in FIG. 34, it is possible to employ a biosignal measurement device 60 in which an auxiliary support section 61 that has a more gentle curve than the curve of the hair band 2 and is shorter than the full length of the hair band 2 is coupled to the top of the curve of the hair band 2 in a direction orthogonal to the hair band 2.

Like the hair band 310 of the head device 300, the hair band 2 of the biosignal measurement device 60 clamps the front and back side sections of the head, and thus its structure is similar to but differs from the hair band 2 of the biosignal measurement device 1 that clamps the left and right side sections of the head.

Specifically, the hair band 2 of the biosignal measurement device 1 is symmetrical (left-right symmetrical) with reference to the position to be abutted against the vertex where the radius of curvature is largest, and the lengths from this position to the ends are roughly the same. Also, the height positions of the both ends of the hair band 2 when attached are substantially the same.

In contrast, like the hair band 310 of the head device 300, the hair band 2 of the biosignal measurement device 60 is asymmetrical (front-back asymmetrical) with reference to the position to be abutted against the vertex where the radius of curvature is largest, and the length from this position to the front end is shorter than the length from this position to the rear end. Also, the positional relation between the height positions of the both ends of the hair band 2 when attached is such that the reference electrode 12 at the occiput abutment section is positioned lower than the non-slip section 11 at the forehead abutment section.

The length of the auxiliary support section 61 is set to such a length that the ends of the auxiliary support section 61 are located at the "C3" and "C4" sites in the international 10-20 system.

In the case where the biosignal measurement device 60 is employed, it is possible to support the head while clamping the head from front to back at four points on the head, including the two points at the forehead and the occipital section, and the two points at "C3" and "C4" in the international 10-20 system, thereby reducing displacement of the electrodes 12 and 13 with respect to the scalp in comparison to the biosignal measurement device 1.

Also, the width of the hair band 2 of the biosignal measurement device 60 is smaller in length than the distance between "C3" and "C4" in the international 10-20 system, and the length of the auxiliary support section 61 is approximately equal to this distance. Therefore, with the biosignal measurement device 60, migraine or discomfort caused when the subject lies down is significantly mitigated, and also the amount of compression applied to the nervous system, the vascular system, the lymphatic system, and the muscular system can be minimized, thereby significantly mitigating migraine or discomfort caused by attachment as well.

It should be noted that the shape of each of the hair band 2 and auxiliary support section 61 of the biosignal measurement device 60 is not limited to a plate-like shape. For example, the shape may be a tubular shape whose cross-section is a circle or ellipse that is hollow or solid, or may be a shape other than such shapes.

Incidentally, in the case of adopting a tubular shape whose cross-section is an ellipse, from the viewpoint of mitigating migraine or discomfort, for example, it is more advantageous to set the surface along the longitudinal diameter direction as the surface to be abutted against the head surface. Also, the probe electrode 13 may be provided at one or either end of the auxiliary support section 61.

Figure 35:
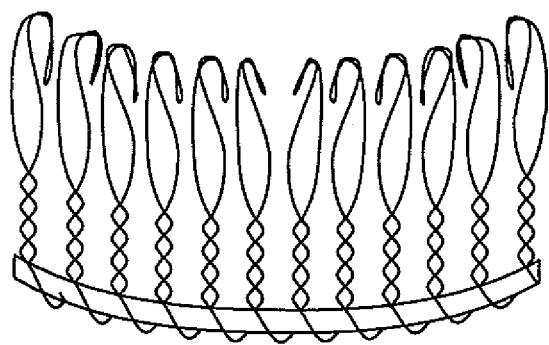
FIG. 35 is a diagram schematically showing the configuration of an electrode according to another embodiment.

As another example, instead of the reference electrode 12 or the probe electrode 13, as shown in FIG. 35, it is possible to employ a reference electrode or a probe electrode whose tooth tip is folded back. Employing this electrode increases twisting of the teeth around the roots of head hair in comparison to the reference electrode 12 or the probe electrode 13, thereby further improving adherence of the teeth to the scalp while further reducing displacement.

As another example, the tooth support rods 12B and 13B in the reference electrode 12 and the probe electrode 13 may be omitted, and the tooth sections 12A and 13B in the reference electrode 12 and the probe electrode 13 may be directly fixed to the inner surface of the hair band 2.

Aside from the above illustrated examples, the components of the biosignal measurement device 1 are not limited to the shapes, structures, and the like illustrated in the above embodiment, and modifications are possible without departing from the scope of the present invention.

In the second embodiment mentioned above, the reference electrode 57 is attached to the earlobe. However, the attaching position of the reference electrode 57 is not limited to this embodiment. For example, the attaching position may be the upper part of the auricle or the temple position.

In the second embodiment mentioned above, the hair band 51, the arm 52, the snap button 53, the electrode support 54, the reference electrode 55, and the probe electrode 57 are employed as the components of the biosignal measurement device 50. However, the components of the biosignal measurement device 50 are not limited to the shapes, structures, and the like illustrated in the above-described embodiment.

Figure 36:
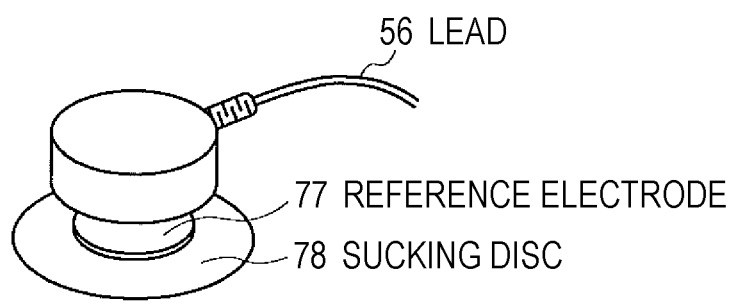
FIG. 36 is a diagram schematically showing an electrode structure according to another embodiment.

For example, instead of the reference electrode 57, as shown in FIG. 36, an electrode structure can be employed which has a sucking disc 78 surrounding a reference electrode 77 formed as a recessed portion. Also, like the electrode used for an electrocardiogram, it is possible to employ an electrode structure in which a tube is attached to a cup-shaped electrode. Of course, an electrode structure other than a sucking disc structure may be employed as well.

As another example, it is possible to employ a mode that omits one of the arms 52A and 52B and the snap buttons 53A and 53B.

Aside from the above illustrated examples, the components of the biosignal measurement device 50 are not limited to the shapes, structures, and the like illustrated in the above embodiment, and modifications are possible without departing from the scope of the present invention.

It should be noted that it is also possible to employ a mode that combines the components of the biosignal measurement device 1 according to the first embodiment mentioned above, and the components of the biosignal measurement device 50 according to the second embodiment as appropriate.

Figure 37:
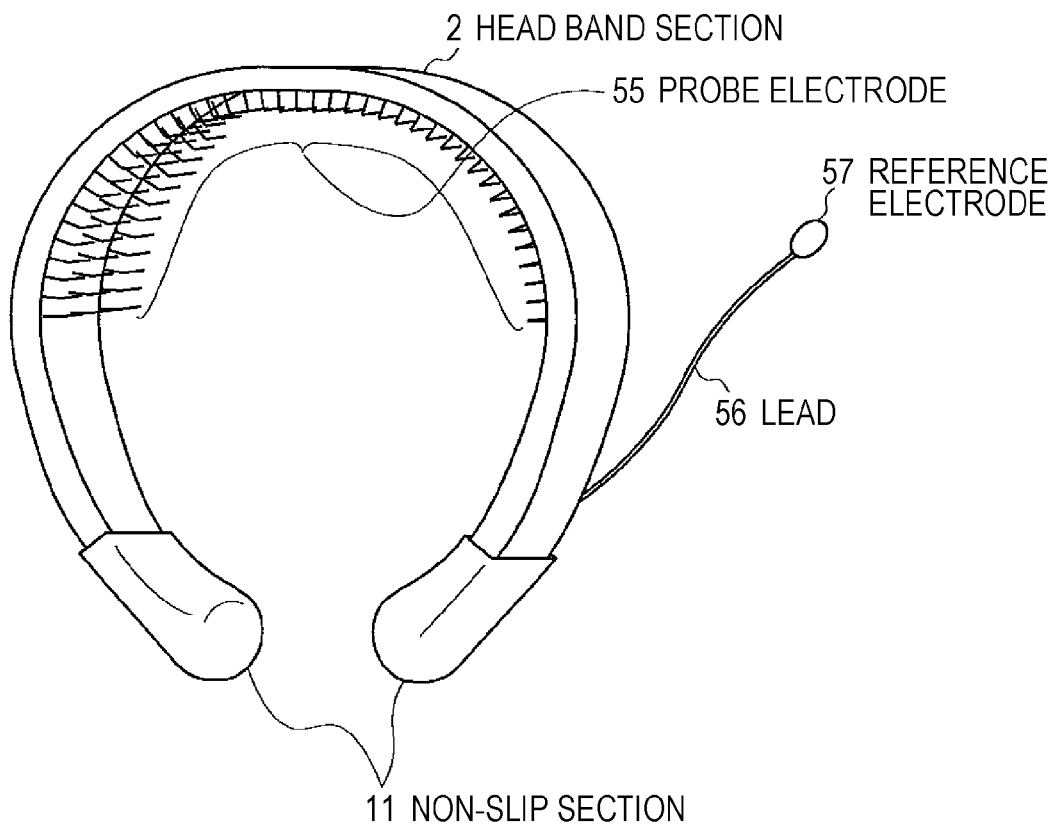
FIG. 37 is a diagram schematically showing the configuration of a biosignal measurement device according to another embodiment.

For example, it is possible to employ a biosignal measurement device 80 shown in FIG. 37 in which portions corresponding to those in FIG. 1 or FIG. 5 are denoted by the same symbols. In the biosignal measurement device 80, the reference electrode 12 provided at the other end of the hair band 2 is changed to the non-slip section 11, and the reference electrode 57 is provided at the distal end of the lead 56 extended from the interior of the hair band 2. Also, in the hair band 2, the probe electrode 55 is provided instead of the probe electrode 13.

Figure 38:
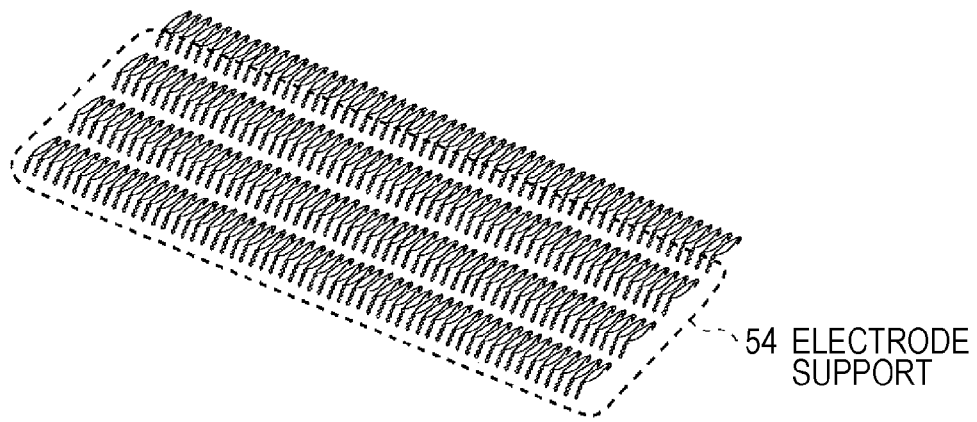
FIG. 38 is a diagram schematically showing an electrode structure according to another embodiment.

As another example, the teeth of the probe electrode 55 shown in FIG. 5 may be employed as the teeth of the probe electrode 13 shown in FIG. 1. In this case, as shown in FIG. 38, the portion of each tooth of the probe electrode 13 which is formed in a rod-like shape (twisted portion (see FIG. 2)) is fixed at its root while facing obliquely to the surface of the electrode support 54, and the portion formed in an annular shape (see FIG. 2) faces parallel to this surface. In this way, it is possible to secure a large area of contact with the scalp. Also, when the electrode support 54 is attached to the vertex, on the surface of the electrode support 54 facing the head, the force exerted as the annular portion of the probe electrode shown in FIG. 38 tries to return to the original state acts as a pressing force against the vertex, thereby further enhancing adherence to the scalp. It should be noted that as the structure for pressing the surface facing the head against the head, structures other than the one shown in FIG. 5 can be employed as well.

The biosignal measurement device 80 shown in FIG. 37 is only an illustrative example of combination, and it is also possible to employ other modes of combination.

In the third embodiment mentioned above, the probe electrodes 320A and 320B have a brush structure. However, the structure of the probe electrodes is not limited to this embodiment. For example, it is possible to employ the structure as shown in FIG. 2, FIG. 6, or FIG. 35.

In the third embodiment mentioned above, the adjuster section 330 is provided between the recess 312 and rear end of the hair band 310. However, the location of installation of the adjuster section 330 in the hair band 310 is not limited to this embodiment. For example, the adjuster section 330 can be provided between the recess 311 and the recess 312, or between the recess 311 and the fixed region 361 of the protruding casing 360. It should be noted, however, that the above-mentioned embodiment is more preferable from the viewpoint of placing its distal end position at a position directly above the point O. It should be noted that the adjuster section 330 may be omitted from the hair band 310.

In the third embodiment mentioned above, the adjuster section 330 of a slider type is provided. Alternatively, it is also possible to make the hair band 310 itself from a material having stretchability, and provide a rigid frame to the sides of the hair band 310 so that the hair band 310 itself can be adjusted in length along the longitudinal direction.

In the third embodiment mentioned above, the button 363 is provided on the upper surface of the protruding region 362, and the connectors 364 are provided on the side surface of the protruding region 362. The locations of installation of the button 363 and connectors 364 are not limited to this embodiment, and various locations can be employed.

In the third embodiment mentioned above, the button 363 adopted is of a type which turns power on or off when pressed for a several seconds. However, the power on or off type is not limited to this embodiment.

For example, a slide type may be employed. As another example, a button of a type which instantaneously turns power on or off when pressed may be provided in such a way so as to be recessed in comparison to the upper surface of the protruding region 362. As another example, a touch sensor may be provided. In short, any type may be used as long as it is possible to prevent accidental power-on/off from occurring when going to sleep or standing up.

In the third embodiment mentioned above, the length of the arm 380, 534 is fixed. However, like the hair band 310, a slide-type adjuster section may be provided, or the arm 380, 534 itself may be made adjustable in length along the longitudinal direction.

In the third embodiment mentioned above, the amplification section 631 is adopted which amplifies the difference between each of the electrodes 320, 370, and 400, and a ground point that is made common. However, it is also possible to employ an amplification section that amplifies the difference between the probe electrode 320A or 320B and the reference electrode 370A or 370B, the difference between the probe electrode 400A and the reference electrode 370A, and the difference between the probe electrode 400B and the reference electrode 370B. Also, the reference electrodes 370A and 370B at the ears may be used to serve as the reference for the entire measurement section. It has been confirmed that in this case as well, a measurement sensitivity that does not render measurement practically impossible was obtained.

Aside from the above illustrated examples, the components of the head device 300 and chin device 500 are not limited to the shapes, structures, and the like illustrated in the third embodiment mentioned above, but various modifications are possible without departing from the scope of the present invention.

While in the first to third embodiments mentioned above the electrodes are directly pressed against the surface of the human body, a coupling medium for efficiently transmitting waves, such as water, alcohol, oil, or glycerin, may be attached to the electrodes. It should be noted that it is also possible to provide a mechanism for passing the coupling medium to the electrodes.

For example, the following configuration may be employed. A container for storing the coupling medium is provided inside each of the hair band 2, the electrode support 54, and the protruding region 362, a needle-shape tube for passing the coupling medium to an electrode is coupled to a valve provided in the container, and the distal end of the tube is placed at one end portion of the electrode.

While brain waves are measured in the first to third embodiments mentioned above, the body temperature or pulse can be added as well. In this case, the biosignal measurement device 1, 50, the head device 300, or the chin device 500 is provided with, for example, an optical body temperature sensor or pulse sensor, and a signal supplied from the sensor is supplied to the analysis section 34 via the A/D conversion section 33. The analysis section 34 stores the body temperature data or pulse data into the memory 35 in association with electroencephalogram data. Such association can be used as an index for identifying a sleep disorder and a disease.

Incidentally, the support (hair band) that is supported on the head while clamping the head from front to back between the portion to be abutted against the forehead and the portion to the abutted against the occiput as ends is not limited to the hair band 2 of the biosignal measurement device 60 or the hair band 310 of the head device 300. For example, a hair band 600 shown in FIG. 39 can be employed.

At both ends of the hair band 600, stoppers made of resin such as rubber are fitted in, and formed as a forehead abutment section 610 and an occiput abutment section 620. The hair band 600 is made of a plastic material or metallic material in the form of a tubing line whose cross-section is a circle or ellipse that is hollow or solid (hereinafter, this will be also referred to as wire-like tube), and is formed in a C-shape.

Specifically, the hair band 600 is asymmetrical (front-back asymmetrical) with reference to the position to be abutted against the vertex where the radius of curvature is largest, and the length from this position to the front end is shorter than the length from this position to the rear end. Also, the positional relation between the height positions of the both ends of the hair band 600 when attached is such that the occiput abutment section 620 at the back side is positioned lower than the forehead abutment section 610 at the front side.

Therefore, the hair band 600 allows for a flexible fit irrespective of the shape of the head, and also the fitting state can be retained.

Also, the width of the hair band 600 is set to a value smaller than the distance between a straight line connecting "F3" and "P3" in the international 10-20 system, and a straight line connecting "F4" and "P4", and is preferably not larger than 25 [mm].

Thus, with the hair band 600, migraine or discomfort caused when the subject lies down is significantly mitigated, and also the amount of compression applied to the nervous system, the vascular system, the lymphatic system, and the muscular system can be minimized, thereby also significantly mitigating migraine or discomfort caused by attachment.

Figure 40:
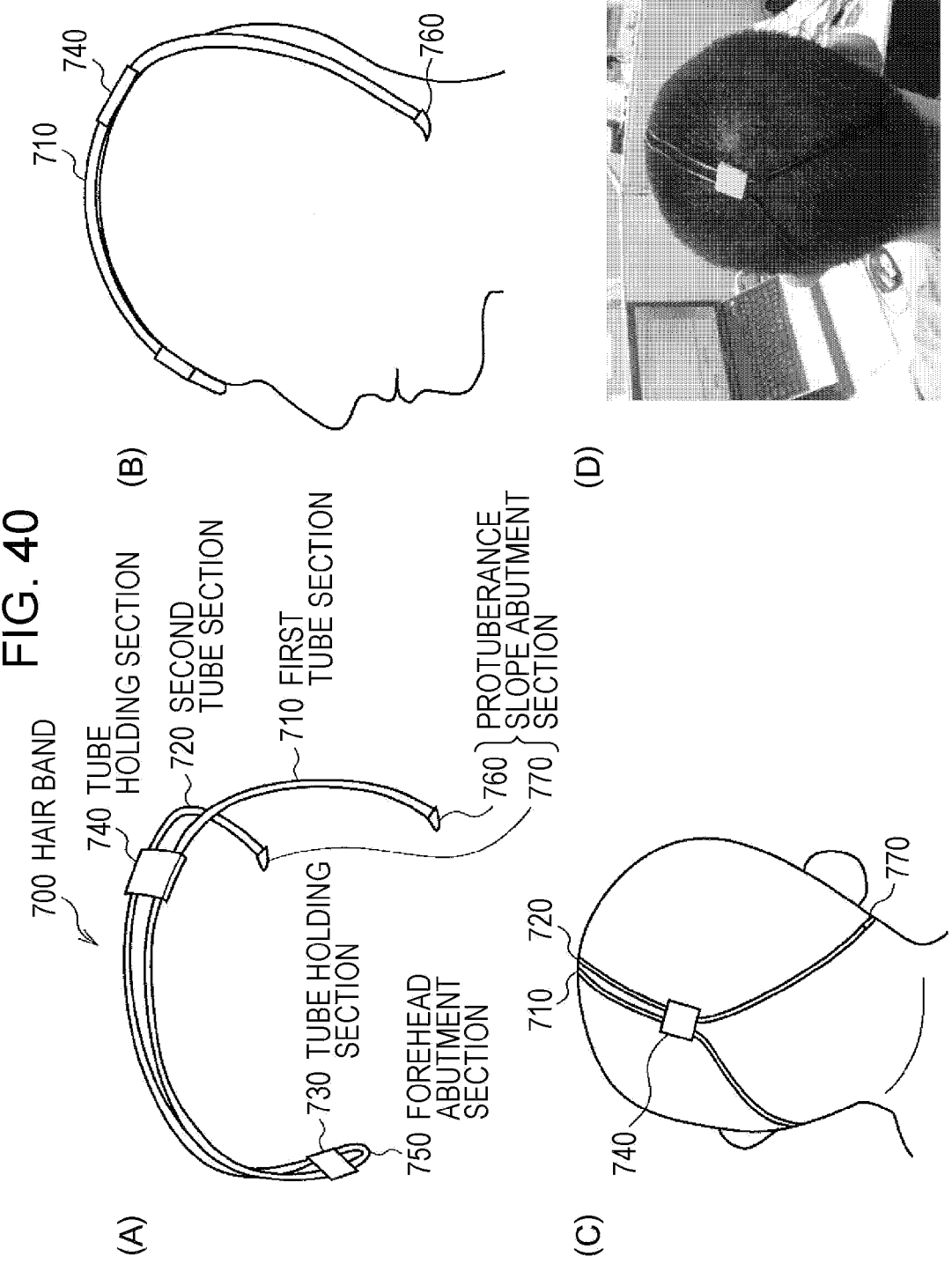
FIG. 40 is a diagram schematically showing a hair band according to another embodiment, and its attached state.

As another example, it is possible to employ a hair band 700 shown in FIG. 40. In the hair band 700, a single wire-like tube is folded over in the middle, forming a tube portion (hereinafter, this will be also referred to as first tube section) 710 extending from the folded end to one open end, and a tube portion (hereinafter, this will be also referred to as second tube section) 720 extending to the other open end.

The first tube section 710 and the second tube section 720 are formed in the same C-shape, and members (hereinafter, also referred to as tube holding sections) 730 and 740 that hold the pair of tubes in a parallel relationship are each attached in a midway position at the same distance from each open end.

By means of the tube holding section 730, the first tube section 710 and the second tube section 720 are formed in a loop that is abutted against the forehead (forehead abutment section 750), from the folded end to a first midway position near the folded end. Also, by means of the tube holding section 740, the first tube section 710 and the second tube section 720 are formed parallel to each other like rails from the first midway position to a second midway position, and are made to branch off away from each other at the second midway position as a branch position.

This branch position (second midway position) is located more toward the back (occipital side) than the position corresponding to the center of the head (the "Cz" position in the international 10-20 system), along the first tube section 710 and the second tube section 720. If the branch position is located more toward the front (forehead side) than the center position of the head, a situation arises in which, for reasons such as the difference between the radius of curvature of the frontal bone and the radius of curvature of the parietal bone, for example, the portion of each of the first tube section 710 and the second tube section 720 from the branch position to the open end lifts up from the surface of the occipital section. Therefore, by placing the branch position more toward the back (open end) than the center position of the head, the amount of fit to the occipital section from the branch position to the open end of each of the first tube section 710 and the second tube section 720 is improved as compared with when the branch position is placed more toward the front (folding end) than the center position of the head.

At the open ends of the first tube section 710 and second tube section 720, there are formed sections (hereinafter, these will be also referred to as protuberance slope abutment sections) 760 and 770 that are abutted against the neck-side sloping portion of the external occipital protuberance. The protuberance slope abutment sections 760 and 770 are tilted more inward than the first tube section 710 and the second tube section 720 located in the vicinity of the protuberance slope abutment sections 760 and 770. Therefore, upon attachment, the protuberance slope abutment sections 760 and 770 are caught on the neck-side sloping portion of the external occipital protuberance, thereby keeping the clamping state with the forehead abutment section 750. As a result, support with respect to the head is enhanced as compared with a case where the protuberance slope abutment sections 760 and 770 are not folded back more inward than the first tube section 710 and the second tube section 720 located in their vicinity.

Also, a stopper made of resin such as rubber is fitted in each of the protuberance slope abutment sections 760 and 770. Thus, support with respect to the head is further enhanced.

When the hair band 700 is employed, it is possible to support the head by clamping the head from front to back at three points, one at the forehead and two at the neck-side sloping portion of the external occipital protuberance. Thus, displacement of electrodes with respect to the scalp can be reduced in comparison to the hair band 600.

Also, the portions of the first tube section 710 and second tube section 720 from the first midway position to the second midway position which are arranged in parallel are made narrower than the distance between "C3" and "C4" in the international 10-20 system. Therefore, with the hair band 700, migraine or discomfort, caused when the subject lies down is significantly mitigated, and also the amount of compression applied to the nervous system, the vascular system, the lymphatic system, and the muscular system can be minimized, thereby significantly mitigating migraine or discomfort caused by attachment as well.

Figure 41:
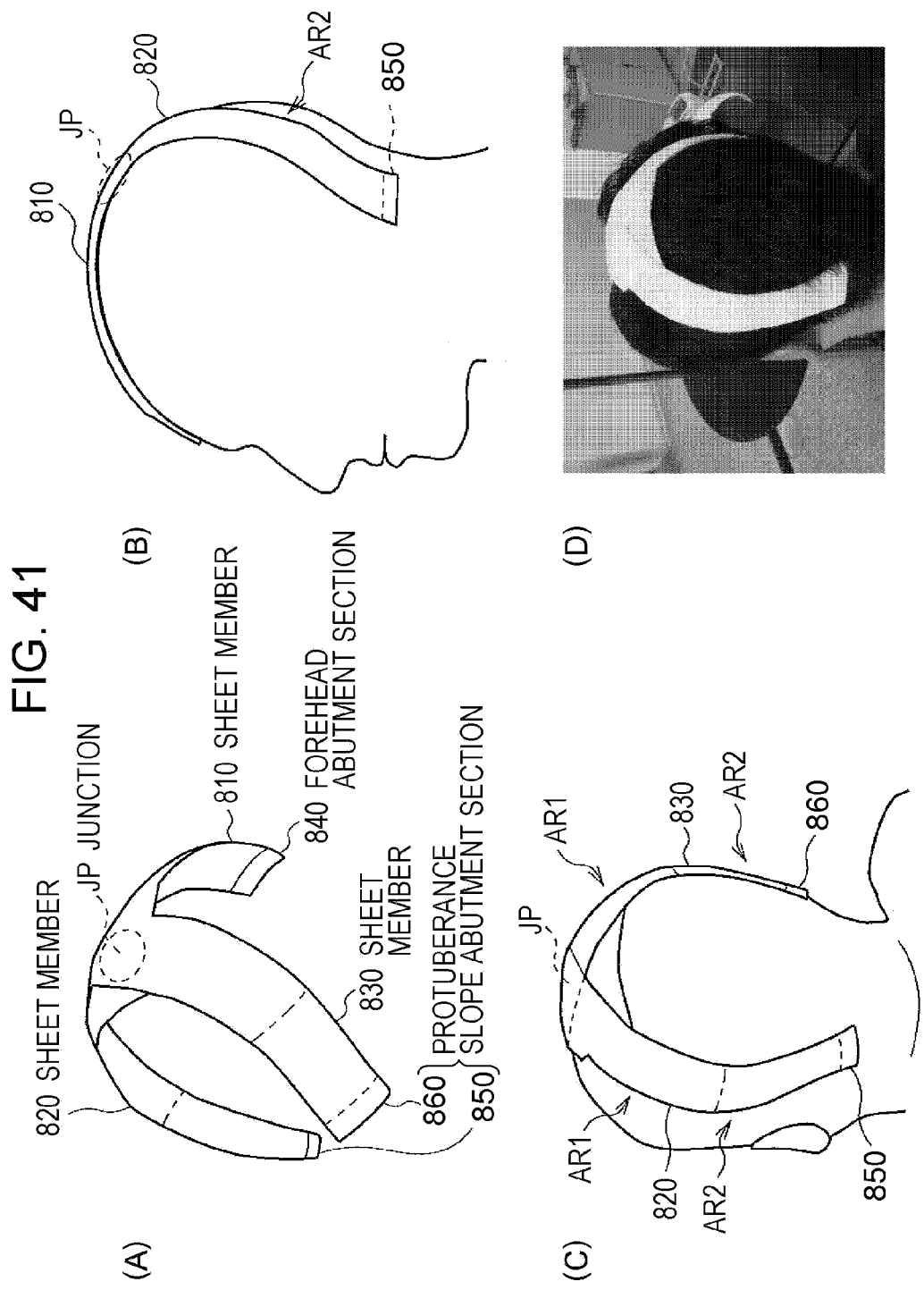
FIG. 41 is a diagram schematically showing a hair band according to another embodiment, and its attached state.

As another example, it is possible to employ a hair band 800 shown in FIG. 41. In the hair band 800, with reference to the portion to be abutted against a position located more toward the occiput than the center position of the head, three sheet members 810, 820, and 830 each made of hydraulic setting resin and having a predetermined width are coupled while assuming a curved shape. A forehead abutment section 840, a protuberance slope abutment section 850, and a protuberance slope abutment section 860 are attached to the distal ends of the sheet members 810, 820, and 830, respectively.

The junction JP of the three sheet members 810, 820, and 830 which serves as a reference in the hair band 800 is a portion that should be abutted against not a position located more toward the forehead than the center position of the head but a position located more toward the occiput. Therefore, as in the case of the hair band 800, the amount of fit to the occipital section from the junction JP to the protuberance slope abutment sections 850 and 860 is improved as compared with when the junction JP is located more toward the forehead than the center position of the head.

Also, in the sheet members 820 and 830 attached with the protuberance slope abutment sections 850 and 860, in comparison to a region AR1 from the vicinity of the center in the lengthwise direction of the sheet members 820 and 830 to the junction JP, a region AR2 from the vicinity of the center to the protuberance slope abutment sections 850 and 860 curves more inward. Therefore, upon attachment, the protuberance slope abutment sections 850 and 860 are caught on the neck-side sloping portion of the external occipital protuberance, thereby keeping the clamping state with the forehead abutment section 840. As a result, fitting is improved as compared with when the region AR2 from the vicinity of the center to the protuberance slope abutment sections 850 and 860 does not curve more inward than the region AR1 from the vicinity of the center to the junction JP, and support with respect to the head is enhanced.

When the hair band 800 is employed, as in the case of employing the hair band 700, it is possible to support the head by clamping the head from front to back at three points, one at the forehead and two at the neck-side sloping portion of the external occipital protuberance. Thus, displacement of electrodes with respect to the scalp can be reduced.

Also, the width of the sheet members is set smaller than the distance between "C3" and "C4" in the international 10-20 system. Therefore, with the hair band 800, like the hair band 700, migraine or discomfort caused when the subject lies down is significantly mitigated, and also the amount of compression applied to the nervous system, the vascular system, the lymphatic system, and the muscular system can be minimized, thereby significantly mitigating migraine or discomfort caused by attachment as well.

Further, since the hair band 800 is formed of hydraulic setting resin, the hair band 800 is disposable, which is advantageous from the viewpoints of cost reduction and ease of handling.

Figure 42:
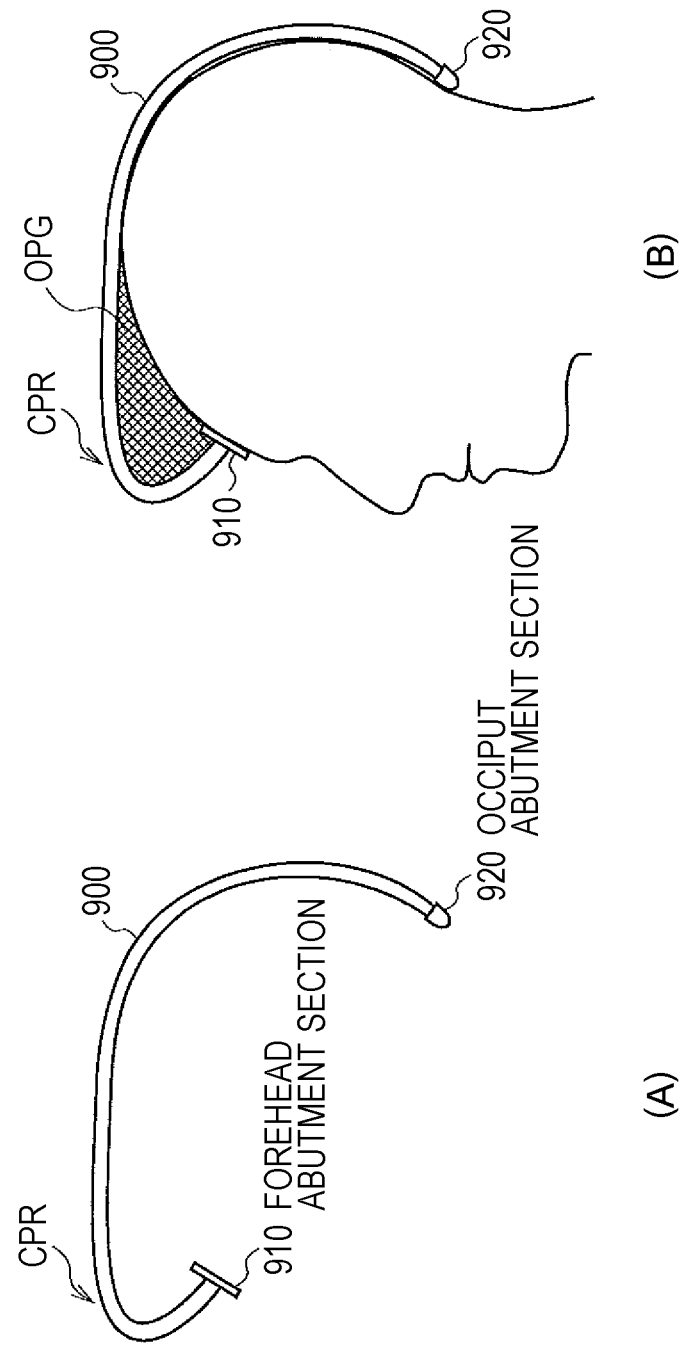
FIG. 42 is a diagram schematically showing a hair band according to another embodiment, and its attached state.

As another example, it is possible to employ a hair band 900 shown in FIG. 42. Stoppers made of resin such as rubber are fitted in both ends of the hair band 900, and formed as a forehead abutment section 910 and an occiput abutment section 920. The hair band 900 is made of a wire-like tube and formed in a chevron shape.

That is, the hair band 900 is asymmetrical (front-back asymmetrical) with reference to the position to be abutted against the vertex, and is the same as the hair band 600 shown in FIG. 39 in that upon attachment, the occiput abutment section 920 is lower in position that the forehead abutment section 910.

However, the hair band 900 extends linearly from the position to be abutted against the forehead toward the forehead abutment section 910, and sharply folds back toward the inner side (the occiput abutment section 920 side) at a portion CRP near the point of contact with the forehead abutment section 910. The hair band 900 differs in this respect from the hair band 600 that is curved along the shape of the head from the position to be abutted against the vertex toward the forehead abutment section 610.

Therefore, upon attachment, the hair band 900 contacts the head only at two points, the forehead and the occiput, and in a part of the contour passing the median plane (the portion excluding a gap OPG in front of the head as shown in FIG. 42). Thus, with the hair band 900, as compared with the hair band 2 of the biosignal measurement device 60, the hair band 600, or the like, compression on the head due to self weight is reduced. As a result, migraine or discomfort caused by attachment is further mitigated.

Also, the width of the hair band 900 is set to a value smaller than the distance between a straight line connecting "F3" and "P3" in the international 10-20 system, and a straight line connecting "F4" and "P4", and is preferably not larger than 25 [mm].

Thus, with the hair band 900, migraine or discomfort caused when the subject lies down is significantly mitigated, and also the amount of compression applied to the nervous system, the vascular system, the lymphatic system, and the muscular system can be minimized, thereby also significantly mitigating migraine or discomfort caused by attachment.

Figure 43:
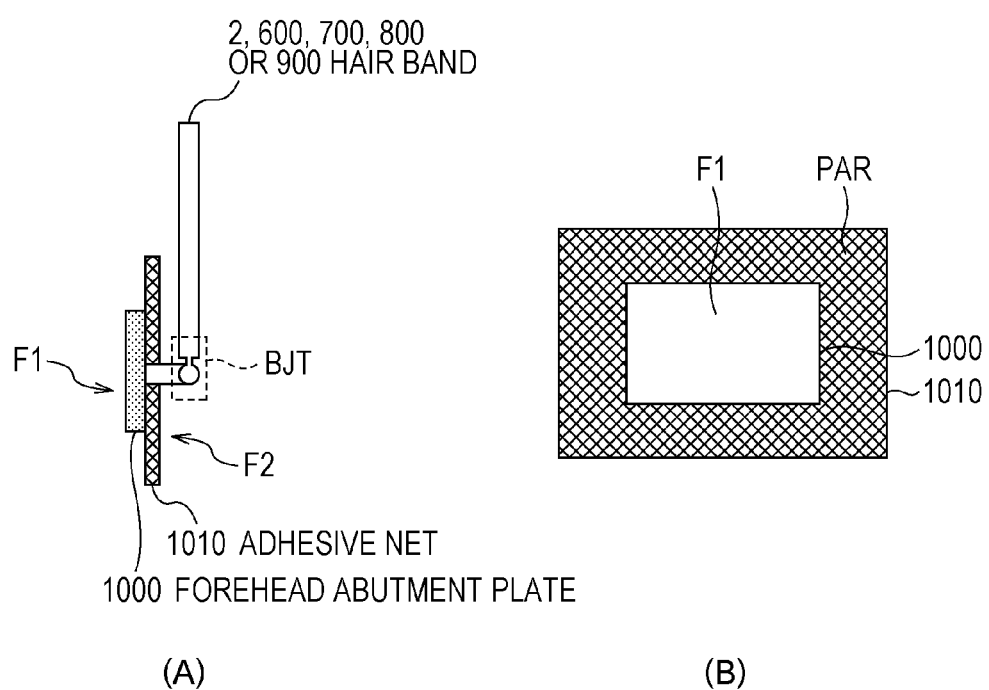
FIG. 43 is a diagram schematically showing the structure of a forehead abutment section according to another embodiment.

Incidentally, the structure shown in FIG. 43 can be employed as the structure of the portion of the hair band 2, 600, 700, 800, or 900 to be abutted against the forehead.

That is, the distal end of the hair band 2, 600, 700, 800, or 900, and a plate member (hereinafter, this will be also referred to as forehead abutment plate) 1000 to be abutted against the forehead are coupled by a ball-type joint BJT.

The ball-type joint BJT has as its components a ball-shaped convex stud, and a concave stud that is slidably fitted to the ball portion of the convex stud. These components are fixed to either the distal end of the hair band 2, 600, 700, 800, or 900 or the forehead abutment plate 1000.

A meshed member (hereinafter, this will be also referred to as adhesive net) 1010 having adhesiveness is attached to a back surface F2 of the forehead abutment plate 1000 opposite to a surface F1 to be abutted against the forehead. The adhesive net 1010 has an area larger than the surfaces F1 and F2 of the forehead abutment plate 1000, and a region (the shaded portion in FIG. 43(B)) other than the region attached to the surface F2 serves as a region (hereinafter, this will be also referred to as forehead-affixed region) PAR to be affixed to the forehead.

That is, the adhesive net 1010 is structured so that the portion to be abutted against the forehead (surface F1), and the portion to be affixed to the forehead (forehead-affixed region PAR) are separate from each other, and is affixed to the forehead in the manner of covering the surface F1 from its back side.

Therefore, as compared with a case where the surface F1 to be abutted against the forehead itself is formed as an adhesive sheet, even when a change occurs in the surface of the forehead such as wrinkles that form when one frowns, displacement of the portion (surface F1) to be abutted against the forehead is reduced.

Also, the forehead abutment plate 1000 is coupled to the hair band (2, 600, 700, 800, or 900) via a movable section (ball-type joint BJT). Therefore, the ball-type joint BJT absorbs the force that is applied to the forehead abutment plate 1000 or the adhesive net 1010 due to a change in the forehead surface. As a result, as compared with a case where the portion between the forehead abutment plate 1000 and the hair band is non-movable, displacement of the forehead abutment plate 1000 and dislodging of the adhesive net 1010 caused by a change in the forehead surface are reduced.

Furthermore, the adhesive net 1010 is meshed and formed with certain stretchability. Thus, as compared with the case of simply using a sheet-like adhesive member, displacement of the forehead abutment plate 1000 and dislodging of the adhesive net 1010 caused by a change in the forehead surface are reduced.

It should be noted that the forehead abutment plate 1000 may be formed as an electrode to determine whether or not the forehead abutment plate 1000 is in contact with the forehead, in the same manner as the electrode contact detection process in the analysis section 34 described above.

Figure 44:
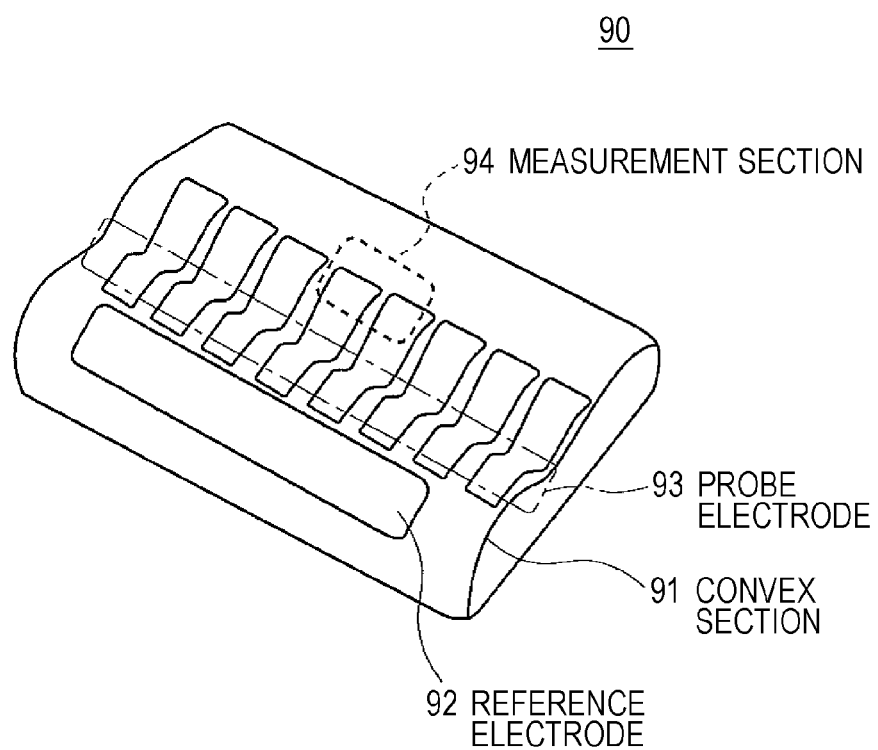
FIG. 44 is a diagram schematically showing the configuration of a biosignal measurement pillow.

Incidentally, instead of the biosignal measurement device 1, 50, 60, the head device 300, or the chin device 500 in each of the first to third embodiments mentioned above, a biosignal measurement pillow 90 shown in FIG. 44 can be employed as well.

The biosignal measurement pillow 90 is of a structure having a part (hereinafter, this will be referred to as convex section) 91 where its one end rises in a convex shape in comparison to the other end so as to fit the base of the neck. In the slope of the convex section 91, a sheet-like reference electrode 92 is provided in the surface of the slope opposite to the slope facing the other end.

On the other hand, in the surface of the biosignal measurement pillow 90, a plurality of plate-like probe electrodes 93 are arrayed at regular intervals in the region between the base of the slope facing the other end of the convex section 91, and a predetermined position between the root and the other end. Also, a measurement section 94 that measures the potential difference between each of the probe electrodes 93 and the reference electrode 92 is provided in the interior of the biosignal measurement pillow 90. As the measurement section 94, the measurement section described above in the first embodiment or third embodiment can be employed.

According to the biosignal measurement pillow 90, since the subject is not forced to attach equipment, burden on the subject can be reduced. Also, since the reference electrode 92 and the probe electrodes 93 are pressed against the surface of the neck base and the scalp by the self weight of the subject, a certain level of measurement sensitivity can be ensured as well.

It should be noted that the structure of the biosignal measurement pillow 90 is not limited to the one shown in FIG. 44. For example, it is possible to employ various structures, such as a structure that is depressed in a concave shape in the middle, and a structure that rises in a convex shape in the middle.

Also, the manner of placement of the probe electrodes 93 is not limited to the one shown in FIG. 44. For example, as shown in FIG. 45, a plurality of linear electrodes may be arrayed at regular intervals in the row or column direction (FIG. 45(A)), may be arrayed at regular intervals in the row and column directions (FIG. 45(B)), or may be arrayed radially (FIG. 45(C)).

Figure 46:
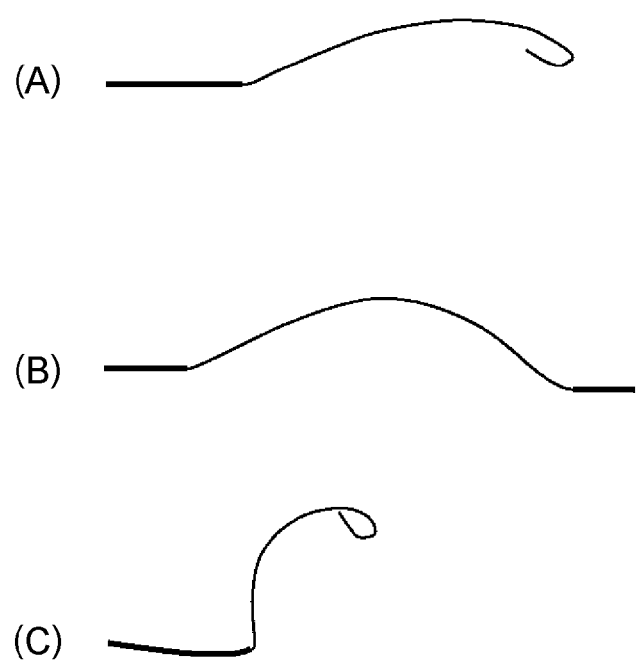
FIG. 46 is a diagram schematically showing electrode shapes according to another embodiment.

Also, the shape of the probe electrodes 93 is not limited to the one shown in FIG. 44. For example, as shown in FIG. 46, the shape may be a comb shape (FIG. 46(A)), a chevron shape (FIG. 46(B)), or a pistil shape (FIG. 46(C)). It should be noted that the thick line in FIG. 46 indicates a fixed part. Also, these electrode shapes can be employed as the shape of the teeth forming the probe electrode 13, 55, or the reference electrode 12 described above.

Figure 47:
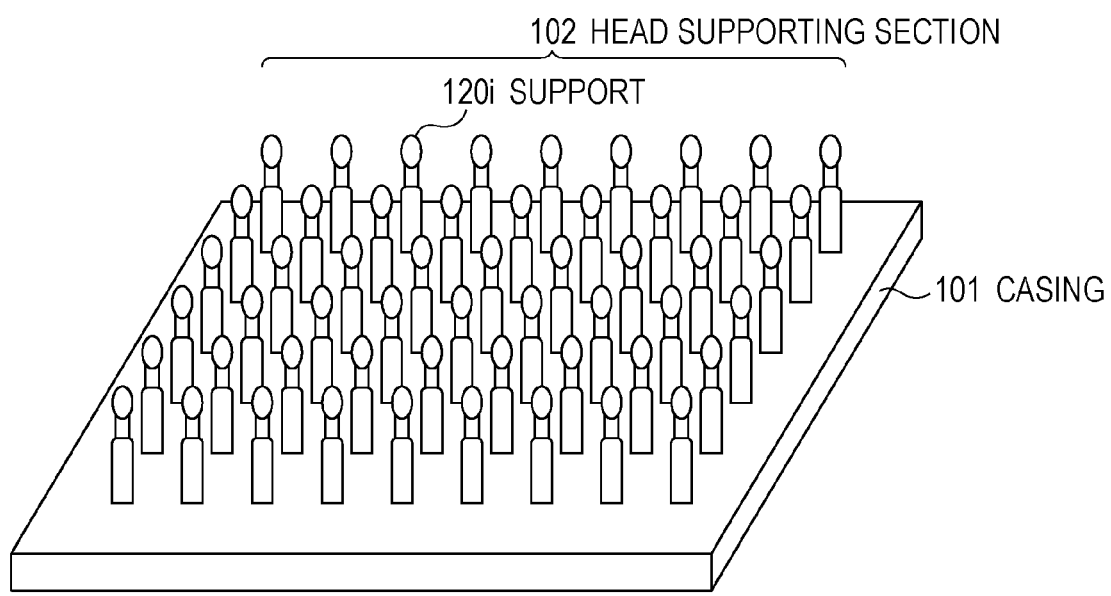
FIG. 47 is a diagram schematically showing the configuration of a biosignal measurement pillow.

Also, instead of the biosignal measurement pillow 90, a biosignal measurement pillow 100 shown in FIG. 47 can be employed as well. The biosignal measurement pillow 100 has a sheet-like casing 101, and a section (hereinafter, this will be also referred to as head support section) 102 that supports the head.

The casing 101 is non-conductive, and one surface of the casing 101 serves as the seating on which the head support section 102 is placed.

Figure 48:
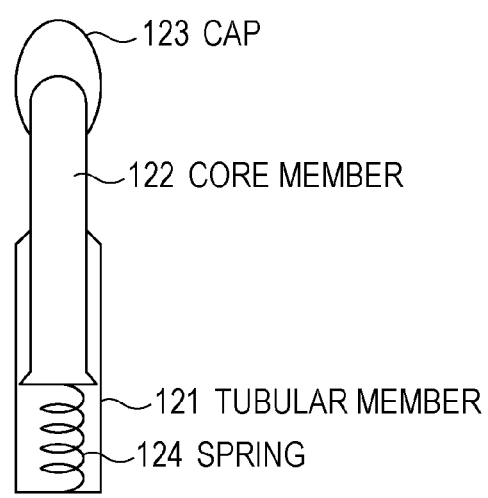
FIG. 48 is a diagram schematically showing the configuration of a support.

The head support section 102 has a structure in which a plurality of supports $120_i$ (i=2, 3, . . . , or m (m is an integer)) are arrayed at regular intervals in the row direction and the column direction. As shown in FIG. 48, the supports $120_i$ each have a conductive tubular member 121, and a conductive core member 122 that is slidably inserted into the hollow of the tubular member 121. A rounded conductive cap 123 having flexibility is attached at one end of the core member 122, and a conductive spring 124 is attached at the other end. As the cap 123, specifically, conductive rubber or the like can be employed, for example.

When the head is placed on the head support section 102 to go to sleep, the core member 122 of each support $120_i$ smoothly slides into the hollow of the tubular member 121 due to the gravity (self weight) exerted on the corresponding part of the head, and the elasticity of the head 124 attached at the other end of the core member 122.

Figure 49:
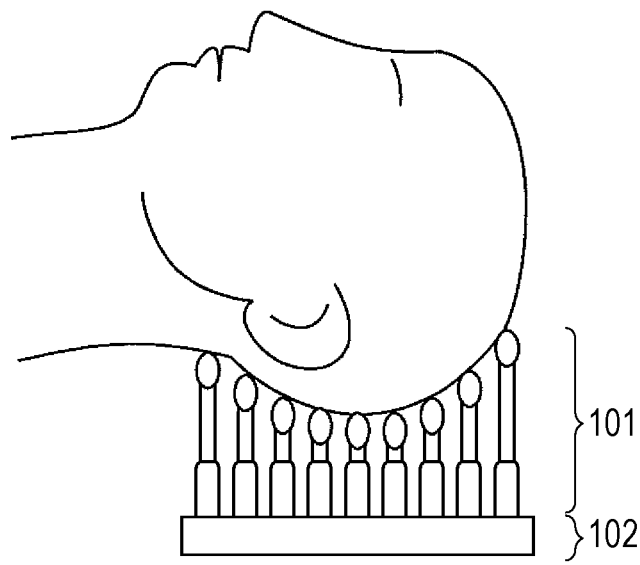
FIG. 49 is a diagram schematically showing a sleeping state.

Therefore, as shown in FIG. 49, the head support section 102 allows the supports $120_i$ to fit the shape of the head irrespective of differences among individuals, and can also mitigate the impact when placing the head on the head support section 102. In addition, as compared with the biosignal measurement pillow 90, adherence of the cap 123 to the scalp improves, thereby improving measurement sensitivity.

Also, since the cap 123 that is rounded and has flexibility is attached at one end of the core member 122, when the head is placed on the head support section 102, pain or the like caused by the portion abutting the head is mitigated.

It should be noted that the above supports $120_i$ can be employed as the teeth forming the probe electrode 13, 55, 320A, 320B, 400A, 400B, 510A, 510B, the reference electrode 57C, 77, 370A, 370B, or the reference electrode 12. Also, the supports $120_i$ can be substituted by the forms shown in FIG. 46. Further, the supports $120_1$ can be also employed for the conductive fibers 321 described above.

Figure 50:
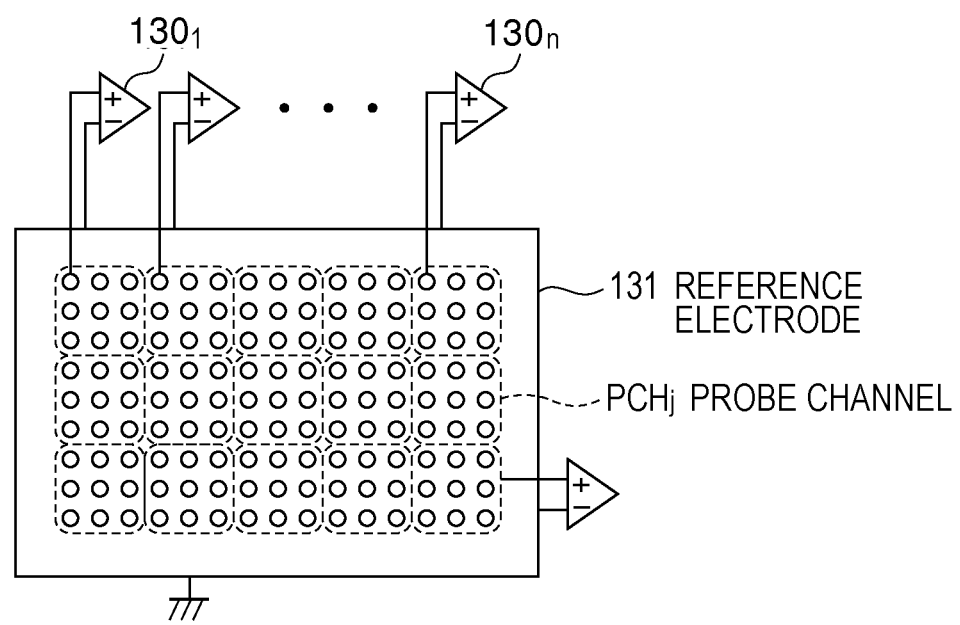
FIG. 50 is a schematic diagram used for explaining assignment of probe channels.

On the other hand, each of the supports $120_i$ can be also used as a probe electrode. In the biosignal measurement pillow 100, as shown in FIG. 50, x rows×y columns of supports are assigned as probe channels $PCH_j$ (j=2, 3, . . . , or n (n is an integer)).

Each of the supports constituting the probe channels $PCH_j$ is connected to one input terminal of the corresponding amplifier $130_j$, and a reference electrode 131 is connected to the other input terminal of the amplifier $130_j$. The amplifier $130_j$ and the reference electrode 131 are accommodated inside the casing 101.

Figure 51:
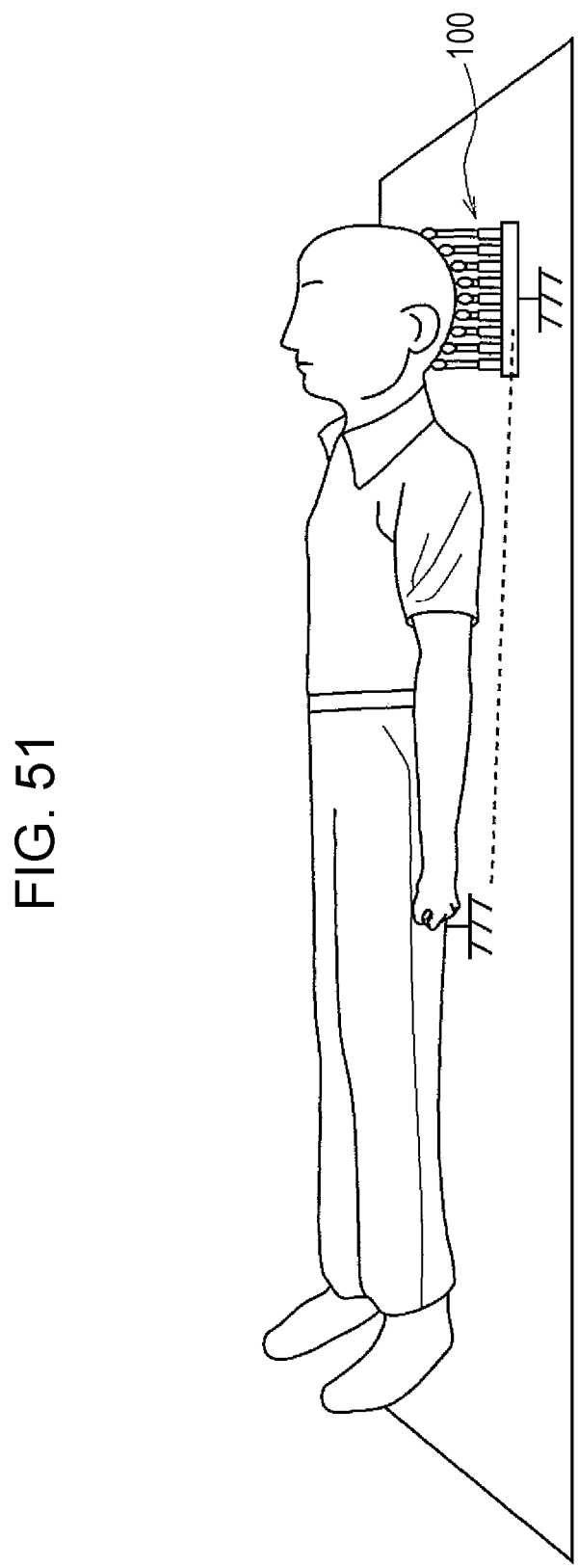
FIG. 51 is a diagram schematically showing a grounding state of a biosignal measurement pillow.

It should be noted that as shown in FIG. 51, the biosignal measurement pillow 100 is grounded via the human body or a futon put over the human body, and is physically ungrounded.

Figure 52:
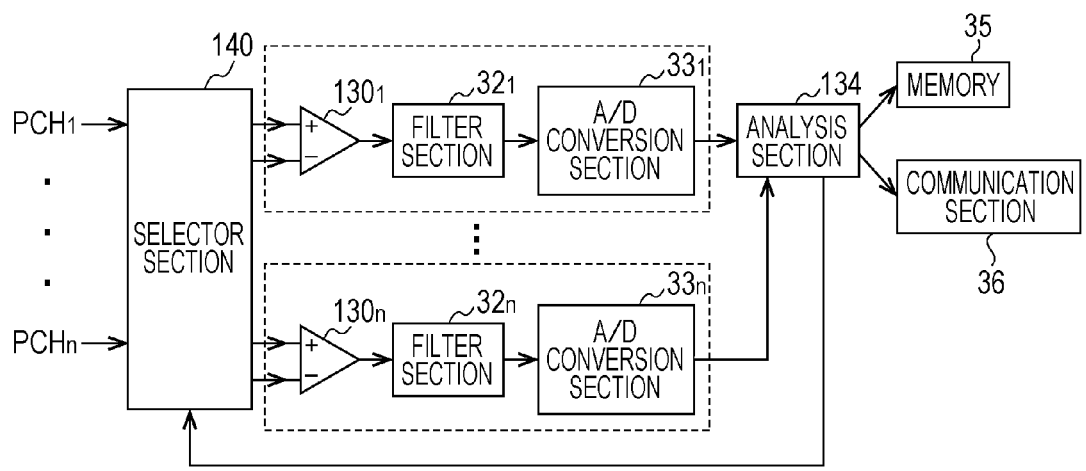
FIG. 52 is a diagram schematically showing the configuration of a measurement section according to another embodiment.

Here, the configuration of a measurement section accommodated inside the casing 101 is shown in FIG. 52 in which portions corresponding to FIG. 4 are denoted by the same symbols. This measurement section differs from the measurement section shown in FIG. 4 in that the function of selecting probe channels to be sensed from among the probe channels $PCH_j$ is added. Specifically, an analysis section 134 with new processing added to the processing in the analysis section 34 is adopted, and a selector section 140 is additionally provided.

For individual probe channels $PCH_j$, the differences of the sums of potentials obtained from the supports constituting the corresponding probe channels $PCH_j$, from the reference electrode 131 are amplified, and sequentially inputted as biosignals to the analysis section 134 via the corresponding filter sections $32_j$ and A/D conversion sections $33_j$.

Figure 53:
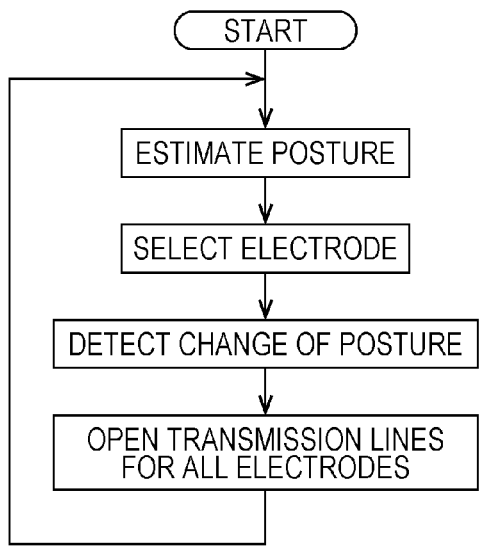
FIG. 53 is a flowchart showing an electrode selection procedure.

By using these biosignals, the analysis section 134 is configured to execute the same processing as the processing described above for the analysis section 34, and also execute an electrode (probe channel) selection process in accordance with the flowchart shown in FIG. 53, for example.

That is, as a first stage, the analysis section 134 estimates the state (posture) of an object (head) with respect to the head support section 102. Parameters (estimation elements) required for this estimation are, for example, the biosignal level in a unit time period, and positional information assigned to the corresponding probe channels $PCH_j$, among the biosignals corresponding to the individual probe channels $PCH_j$.

As a second stage, the analysis section 134 detects the probe channels $PCH_j$ to be selected, on the basis of the estimation result of the state (posture) of the object (head) with respect to the head support section 102, and supplies a select command corresponding to the detection result to the selector section 140. Specifically, for example, probe channels $PCH_j$ other than those probe channels $PCH_j$ corresponding to positions where the biosignal level becomes less than a predetermined value are detected as the probe channels $PCH_j$ to be selected. Therefore, in the selector section 140, transmission lines for the probe channels $PCH_j$ corresponding to positions where the biosignal level becomes less than a predetermined value are cut off. As a result, only transmission lines for the probe channels $PCH_j$ where the head is placed on the head support section 102 are selected.

As a third stage, the analysis section 134 detects a change in the state (posture) of the object (head) with respect to the head support section 102, on the basis of biosignals corresponding to the probe channels $PCH_j$ selected in the second stage. Parameters (detection elements) required for this detection are, for example, the rate of decrease in biosignal level per unit time, and the number of biosignals whose rates of decrease become larger than a threshold that is set for the rate of decrease. In this example, if, among the biosignals corresponding to the probe channels $PCH_j$ selected in the second stage, the number of biosignals whose rates of decrease become larger than the threshold exceeds a predetermined number, it is regarded that the posture of the head placed on the head support section 102 has changed.

If a change in the state (posture) of the object (head) with respect to the head support section 102 is detected, as a fourth stage, the analysis section 134 supplies to the selector section 140 a command indicating that the transmission lines for all probe channels $PCH_j$ be opened, and then executes the processes from the first stage to the third stage again.

The analysis section 134 is configured to execute the electrode (probe channel) selection process in this way.

Figure 56:
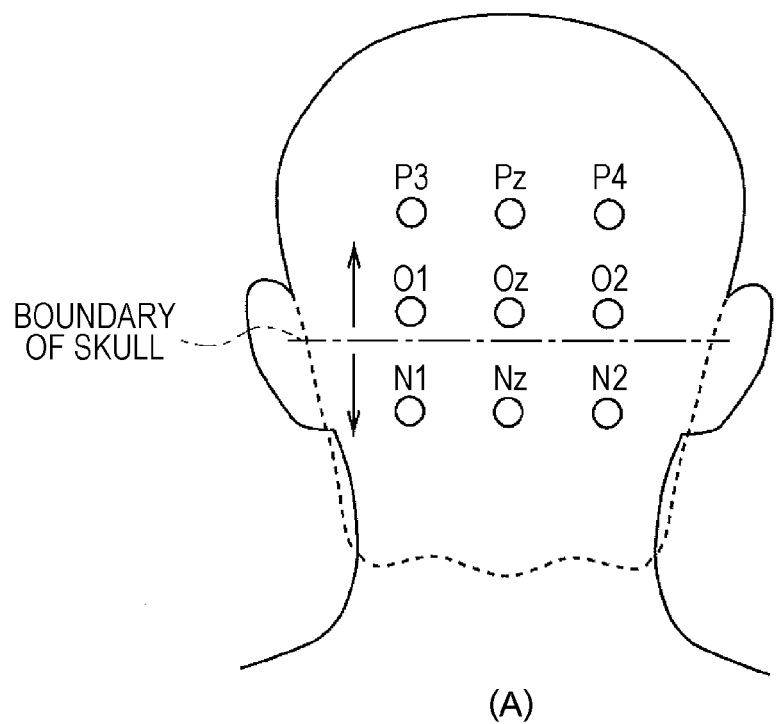
FIG. 56 is a diagram schematically showing the placement of electrodes during experiment.

It should be noted that the experimental results assuming the biosignal measurement pillow 100 are shown in FIG. 54 and FIG. 55, and the electrode placement in the experiment is shown in FIG. 56. As can be appreciated from the experimental results, biosignals were measured with a measurement sensitivity that poses no practical problem.

INDUSTRIAL APPLICABILITY

The present invention has applicability in the medical industry, the game industry, and so on.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

REFERENCE SIGNS LIST 1, 50, 60, 80 biosignal measurement device
2, 51, 61, 310, 600, 700, 800, 900 hair band
11 non-slip section
12, 57, 77, 370A, 370B reference electrode
13, 55, 320A, 320B, 400A, 400B, 510A, 510B probe electrode
12A, 13A tooth section
12B, 13B tooth support rod
31 amplification section
32 filter section
33 A/D conversion section
34 analysis section
35 memory
36 communication section
52 arm
53 snap button
54 electrode support
56 lead
57A, 57B clamping member
57C rivet
61 auxiliary support section
78 sucking disc
90, 100 biosignal measurement pillow
300 head device
330 adjuster section
340, 620, 920 occiput abutment section
350, 610, 750, 840, 910 forehead abutment section
360 protruding casing
380A to 380D arm
390A, 390B earlobe attachment section
500 chin device
501 casing
520 electronic board
530 rail
710 first tube section
720 second tube section
730, 740 tube holding section 760, 770, 850, 860 protuberance slope abutment section

The invention claimed is:

1. A biosignal measurement device for measurement of a biosignal in a head, comprising:
a support configured to attach to the head;
a plurality of depressions in a surface of the support at first intervals;
a plurality of electrodes in the plurality of depressions;
a plurality of grooves at second intervals in a lengthwise direction of the support; and
an adjuster section configured to slide in the lengthwise direction of the support,
wherein at least one of the plurality of electrodes includes a substrate and a plurality of conductive fibers,
wherein an end of conductive fiber of the plurality of conductive fibers is fixed to a surface of the substrate, wherein each conductive fiber of the plurality of conductive fibers is orthogonal to the surface of the substrate, and
wherein a portion of an inner surface of the adjuster section facing the plurality of grooves is provided with a claw configured to fit in each groove of the plurality of grooves.

2. The biosignal measurement device according to claim 1,
wherein the support is further configured to attach to the head while clamping the head between a forehead abutment section abutted against a forehead and an occiput abutment section abutted against an occiput.

3. The biosignal measurement device according to claim 2, wherein:
the substrate is fixed to one of the plurality of depressions in the surface of the support; and
the one of the plurality of depressions has a depth such that a distal end portion of each of the plurality of conductive fibers projects from the surface of the support and the one of the plurality of depressions has a first surface area larger than a second surface area in which the plurality of conductive fibers are fixed to the substrate.

4. The biosignal measurement device according to claim 3, wherein the plurality of conductive fibers comprise a material selected from a group consisting of: carbon, amorphous carbon, stainless steel, and copper sulfide chemically bonded to acrylic fibers and nylon fibers.

5. The biosignal measurement device according to claim 2, wherein an inner surface of the forehead abutment section includes a recessed groove.

6. The biosignal measurement device according to claim 1, wherein an outer surface of the support is provided with a casing that protrudes from the outer surface.

7. The biosignal measurement device according to claim 6, wherein the casing includes a fixed region and a protruding region, and wherein the protruding region is separated from the support and protruded upward at a distance from the outer surface of the support.

8. A biosignal measurement device for measurement of a biosignal in a head, comprising:
a support configured to attach to the head;
a plurality of depressions in a surface of the support at first intervals;
a plurality of electrodes in the plurality of depressions,
wherein at least one of the plurality of electrodes includes a substrate and a plurality of conductive fibers,
wherein an end of each conductive fiber of the plurality of conductive fibers is fixed to a surface of the substrate, wherein each conductive fiber of the plurality of conductive fibers is orthogonal to the surface of the substrate,
wherein the support is attached to a forehead abutment section at a front end of the support and attached to an occiput abutment section at a rear end of the support,
wherein the occiput abutment section includes a first region and a second region,
wherein the first region is a center region of the occiput abutment section,
wherein the second region is a region of the occiput abutment section other than the center region of the occiput abutment section such that the second region surrounds the first region, and
wherein the first region and the second region of the occiput abutment section comprise different materials;
a plurality of grooves at second intervals in a lengthwise direction of the support; and
an adjuster section configured to slide in the lengthwise direction of the support,
wherein a portion of an inner surface of the adjuster section facing the plurality of grooves is provided with a claw configured to fit in each groove of the plurality of grooves.

9. The biosignal measurement device according to claim 8,
wherein the occiput abutment section has one of an acuminate fin shape or a spade shape.

10. The biosignal measurement device according to claim 8,
wherein an area of the occiput abutment section is wider than an area of the forehead abutment section.

11. The biosignal measurement device according to claim 8,
wherein the forehead abutment section has a teardrop shape.

12. The biosignal measurement device according to claim 8,
wherein the forehead abutment section and the first region of the occiput abutment section comprise different materials.

13. The biosignal measurement device according to claim 8,
wherein the forehead abutment section and the second region of the occiput abutment section comprise a same material.

* * * * *